United States Patent
Bhatia et al.

(10) Patent No.: US 10,527,619 B2
(45) Date of Patent: Jan. 7, 2020

(54) AFFINITY-BASED DETECTION OF LIGAND-ENCODED SYNTHETIC BIOMARKERS

(71) Applicant: Massachusetts Institute of Technology, Cambridge, MA (US)

(72) Inventors: Sangeeta N. Bhatia, Lexington, MA (US); David K. Wood, Minneapolis, MN (US); Gabriel A. Kwong, Boston, MA (US); Andrew D. Warren, Cambridge, MA (US); Kevin Y. Lin, Richland, MI (US)

(73) Assignee: Massachusetts Institute of Technology, Cambridge, MA (US)

( * ) Notice: Subject to any disclaimer, the term of this patent is extended or adjusted under 35 U.S.C. 154(b) by 751 days.

(21) Appl. No.: 14/298,662

(22) Filed: Jun. 6, 2014

(65) Prior Publication Data

US 2014/0363833 A1 Dec. 11, 2014

Related U.S. Application Data

(60) Provisional application No. 61/832,766, filed on Jun. 7, 2013.

(51) Int. Cl.
*G01N 31/00* (2006.01)
*G01N 33/53* (2006.01)
*G01N 33/573* (2006.01)
*G01N 33/543* (2006.01)

(52) U.S. Cl.
CPC ..... *G01N 33/573* (2013.01); *G01N 33/54306* (2013.01); *G01N 2333/974* (2013.01); *G01N 2800/226* (2013.01)

(58) Field of Classification Search
None
See application file for complete search history.

(56) References Cited

U.S. PATENT DOCUMENTS

| | | | |
|---|---|---|---|
| 5,500,161 A | 3/1996 | Andrianov et al. | |
| 5,811,252 A | 9/1998 | Verheijen | |
| 5,885,775 A | 3/1999 | Haff et al. | |
| 6,592,847 B1 | 7/2003 | Weissleder et al. | |
| 6,597,996 B1 | 7/2003 | Venkataraman et al. | |
| 6,629,040 B1 | 9/2003 | Goodlett et al. | |
| 6,824,981 B2 | 11/2004 | Chait et al. | |
| 7,041,453 B2 | 5/2006 | Yang | |
| 7,179,655 B2 | 2/2007 | Patricelli | |
| 7,329,506 B2 | 2/2008 | William | |
| 7,412,332 B1 | 8/2008 | Venkataraman et al. | |
| 7,456,269 B2 | 11/2008 | Gurney et al. | |
| 7,468,258 B2 | 12/2008 | Owen | |
| 7,544,518 B2 | 6/2009 | Aebersold et al. | |
| 7,595,155 B2 | 9/2009 | Murakami | |
| 8,673,267 B2 * | 3/2014 | Bhatia ............... | C07K 7/06 424/9.1 |
| 9,006,415 B2 | 4/2015 | Ren et al. | |
| 9,970,941 B2 * | 5/2018 | Bhatia ............... | G01N 33/6848 |
| 10,006,916 B2 | 6/2018 | Kwong et al. | |
| 2002/0119490 A1 | 8/2002 | Aebersold et al. | |
| 2005/0260695 A1 | 11/2005 | Fleming et al. | |
| 2006/0008856 A1 | 1/2006 | Singh et al. | |
| 2006/0292631 A1 | 12/2006 | Broberg et al. | |
| 2007/0010433 A1 | 1/2007 | Albrechtsen et al. | |
| 2007/0048752 A1 | 3/2007 | Yan et al. | |
| 2007/0207555 A1 | 9/2007 | Guerra et al. | |
| 2008/0026480 A1 | 1/2008 | Guerra | |
| 2008/0064607 A1 | 3/2008 | Yang | |
| 2008/0095758 A1 | 4/2008 | Lee et al. | |
| 2008/0113875 A1 | 5/2008 | Chaurand et al. | |
| 2008/0213377 A1 | 9/2008 | Bhatia et al. | |
| 2008/0241955 A1 | 10/2008 | Purkayastha et al. | |
| 2009/0016988 A1 | 1/2009 | Buckley | |
| 2009/0088332 A1 | 4/2009 | Ju et al. | |
| 2009/0156424 A1 | 6/2009 | Thompson | |
| 2009/0246142 A1 | 10/2009 | Bhatia et al. | |
| 2010/0022408 A1 | 1/2010 | Singh et al. | |
| 2010/0124757 A1 | 5/2010 | Kwon et al. | |
| 2010/0190193 A1 | 7/2010 | Calatzis et al. | |
| 2010/0240050 A1 | 9/2010 | Bhatia et al. | |
| 2010/0317542 A1 | 12/2010 | Lim et al. | |
| 2013/0295129 A1 | 11/2013 | Irvine et al. | |
| 2014/0234431 A1 | 8/2014 | Bhatia et al. | |

(Continued)

FOREIGN PATENT DOCUMENTS

| | | |
|---|---|---|
| CN | 102558362 A | 7/2012 |
| CN | 103012595 A | 4/2013 |
| JP | 2004-506900 | 3/2004 |
| JP | 2004-129651 | 4/2004 |
| JP | 2007-24631 A2 | 2/2007 |
| JP | 2009-524688 | 7/2009 |
| JP | 2009-538430 A | 11/2009 |
| WO | WO 2002/014867 A2 | 2/2002 |
| WO | WO 2008/072676 A1 | 6/2008 |
| WO | WO 2008/127019 A1 | 10/2008 |
| WO | WO 2010/101628 A2 | 9/2010 |
| WO | WO 2012/125808 A1 | 9/2012 |
| WO | WO 2014/197816 | 12/2014 |

OTHER PUBLICATIONS

Omar O. Abudayyeh, "Nanoparticle-Chaperoned Urinary "Synthetic Biomarkers" for Profiling Proteases in Cancer", Thesis, Department of Mechanical Engineering, Jun. 2012.*

(Continued)

*Primary Examiner* — Lisa V Cook
(74) *Attorney, Agent, or Firm* — Wolf, Greenfield & Sacks, P.C.

(57) ABSTRACT

The invention relates to methods and products associated with in vivo enzyme profiling. In particular, biomarker nanoparticles capable of quantitatively detecting enzymatic activity in vivo are described. These nanoparticles can be used to detect in vivo enzyme activity. The invention also relates to products, kits, and databases for use in the methods of the invention.

22 Claims, 15 Drawing Sheets
Specification includes a Sequence Listing.

(56) References Cited

U.S. PATENT DOCUMENTS

| | | | |
|---|---|---|---|
| 2014/0303014 A1 | 10/2014 | Kwong et al. | |
| 2015/0165062 A1 | 6/2015 | Liao et al. | |
| 2018/0196058 A1 | 7/2018 | Kwong et al. | |
| 2018/0328941 A1 | 11/2018 | Bhatia et al. | |
| 2018/0335429 A1 | 11/2018 | Bhatia et al. | |

OTHER PUBLICATIONS

Tascilar et al. (Annals of Oncology 10,Suppl. 4:S107-S110, 1999).*
Tockman et al. (Cancer Research 52:2711s-2718s, 1992).*
EP 12757730.2, Dec. 17, 2014, Partial Supplementary European Search Report.
EP 10 74 9044, Jul. 4, 2012, Extended European Search Report.
PCT/US2010/000633, Sep. 15, 2011, International Preliminary Report on Patentability.
PCT/US2010/000633, Jun. 28, 2010, International Search Report and Written Opinion.
PCT/US2012/029200, Jul. 13, 2012, International Search Report and Written Opinion.
PCT/US2014/041370, Sep. 26, 2014, International Search Report and Written Opinion.
EP 14808260.5, Nov. 7, 216, Extended European Search Report.
Deng et al., Gold nanoparticles based molecular beacons for in vitro and in vivo detection of the matriptase expression on tumor. Biosens Bioelectron. Nov. 15, 2013;49:216-21. doi: 10.1016/j.bios.2013.05.018. Epub May 25, 2013.
Nahrendorf et al., Hybrid in vivo FMT-CT imaging of protease activity in atherosclerosis with customized nanosensors. Arterioscler Thromb Vasc Biol. Oct. 2009;29(10):1444-51. doi: 10.1161/ATVBAHA.109.193086. Epub Jul. 16, 2009.
Warren et al., Point-of-care diagnostics for noncommunicable diseases using synthetic urinary biomarkers and paper microfluidics. Proc Natl Acad Sci U S A. Mar. 11, 2014;111(10):3671-6. doi: 10.1073/pnas.1314651111. Epub Feb. 24, 2014.
Abrahamson et al., Isolation of six cysteine proteinase inhibitors from human urine. Their physicochemical and enzyme kinetic properties and concentrations in biological fluids. J Biol Chem. Aug. 25, 1986;261(24):11282-9.
Anderson et al., Mass spectrometric quantitation of peptides and proteins using Stable Isotope Standards and Capture by Anti-Peptide Antibodies (SISCAPA). J Proteome Res. Mar.-Apr. 2004;3(2):235-44.
Asai et al., A colorimetric assay for plasma antithrombin III using a new synthetic peptide substrate (PS-915). Clin Chim Acta. Dec. 29, 1984;144(2-3):163-71.
Baruch et al., Enzyme activity—it's all about image. Trends Cell Biol. Jan. 2004;14(1):29-35.
Becker et al., Thrombin: Structure, Biochemistry, Measurement, and Status in Clinical Medicine. J Thromb Thrombolysis. Jul. 1998;5(3):215-229.
Blum et al., Noninvasive optical imaging of cysteine protease activity using fluorescently quenched activity-based probes. Nat Chem Biol. Oct. 2007;3(10):668-77. Epub Sep. 9, 2007.
Bounameaux et al., Plasma measurement of D-dimer as diagnostic aid in suspected venous thromboembolism: an overview. Thromb Haemost. Jan. 1994;71(1):1-6.
Daniel et al., Implantable diagnostic device for cancer monitoring. Biosens Bioelectron. Jul. 15, 2009;24(11):3252-7. Epub Apr. 16, 2009.
De La Rica et al., Enzyme-responsive nanoparticles for drug release and diagnostics. Adv Drug Rev. Aug. 2012;64(11):967-78. doi: 10.1016/j.addr.2012.01.002. Epub Jan. 14, 2012.
Dranoff, Cytokines in cancer pathogenesis and cancer therapy. Nat Rev Cancer. Jan. 2004;4(1):11-22.
D'Souza et al., A strategy for blood biomarker amplification and localization using ultrasound. Proc Natl Acad Sci U S A. Oct. 6, 2009;106(40):17152-7. doi: 10.1073/pnas.0903437106. Epub Sep. 23, 2009.

Fowlkes et al., Proteolysis of insulin-like growth factor binding protein-3 during rat pregnancy: a role for matrix metalloproteinases. Endocrinology. Dec. 1994;135(6):2810-3.
Fusaro et al., Prediction of high-responding peptides for targeted protein assays by mass spectrometry. Nat Biotechnol. Feb. 2009;27(2):190-8. doi: 10.1038/nbt.1524. Epub Jan. 25, 2009.
Genbank Submission; NIH/NCBI, Accession No. 2WV1_A; Kovalevskiy et al.; Mar. 24, 2010.
Genbank Submission; NIH/NCBI, Accession No. CAG01641; Mar. 17, 2004.
Genbank Submission; NIH/NCBI, Accession No. NP_731669; Hoskins et al.; Dec. 18, 2009.
Genbank Submission; NIH/NCBI, Accession No. NP_938673; Cerdeno-Tanaga et al.; Jun. 3, 2010.
Genbank Submission; NIH/NCBI, Accession No. XP_001385378; Jeffries et al.; Apr. 11, 2008.
Genbank Submission; NIH/NCBI, Accession No. XP_002097000; Clark et al.; Aug. 12, 2009.
Genbank Submission; NIH/NCBI, Accession No. XP_00234527.; Jul. 7, 2006.
Genbank Submission; NIH/NCBI, Accession No. ZP_03507634; Gonzalez et al.; Dec. 19, 2008.
Genbank Submission; NIH/NCBI, Accession No. ZP_06431346; Small et al.; Jun. 9, 2010.
Ghadiali et al., Enzyme-Responsive Nanoparticle Systems. Advanced Materials. 2008;20(22):4359-4363.
Giljohann, et al., Drivers of biodiagnostic development. Nature. Nov. 26, 2009;462(7272):461-4. doi: 10.1038/nature08605.
Ginsberg et al., Sensitivity and specificity of a rapid whole-blood assay for D-dimer in the diagnosis of pulmonary embolism. Ann Intern Med. Dec. 15, 1998;129(12):1006-11.
Grayson et al., Multi-pulse drug delivery from a resorbable polymeric microchip device. Nat Mater. Nov. 2003;2(11):767-72.
Gross, Mass Spectrometry: A Textbook. Springer. $2^{nd}$ ed. Mar. 1, 2011. Chapter 9. 415-452.
Haro et al., Matrix metalloproteinase-7-dependent release of tumor necrosis factor-alpha in a model of herniated disc resorption. J Clin Invest. Jan. 2000;105(2):143-50.
Haun et al., Micro-NMR for rapid molecular analysis of human tumor samples. Sci Transl Med. Feb. 23, 2011;3(71):71ra16. doi: 10.1126/scitranslmed.3002048.
Imai et al., Degradation of decorin by matrix metalloproteinases: identification of the cleavage sites, kinetic analyses and transforming growth factor-beta1 release. Biochem J. Mar. 15, 1997;322.(Pt 3):809-14.
Ito et al., Degradation of interleukin 1beta by matrix metalloproteinases. J Biol Chem. Jun. 21, 1996;271(25):14657-60.
Jaffer et al., In vivo imaging of thrombin activity in experimental thrombi with thrombin-sensitive near infrared molecular probe. Arterioscler Thromb Vasc Biol. Nov. 1, 2002;22(11):1929-35.
Johnson et al., Computer program (SEQPEP) to aid in the interpretation of high-energy collision tandem mass spectra of peptides. Biomed Environ Mass Spectrom. Nov. 1989;18(11):945-57.
Kastelic et al., Stefin B, the major low molecular weight inhibitor in ovarian carcinoma. Cancer Lett. Jul. 15, 1994;82(1):81-8.
Kircher et al., A dual fluorochrome probe for imaging proteases. Bioconjug Chem. Mar.-Apr. 2004;15(2):242-8.
Kuhn et al., Developing multiplexed assays for troponin I and interleukin-33 in plasma by peptide immunoaffinity enrichment and targeted mass spectrometry. Clin Chem. Jun. 2009;55(6):1108-17. doi: 10.1373/clinchem.2009.123935. Epub Apr. 16, 2009.
Kwong et al., Mass-encoded synthetic biomarkers for multiplexed urinary monitoring of disease. Nat Biotechnol. Jan. 2013; 31(1):63-70. doi: 10.1038/nbt.2464.
Lange et al., Selected reaction monitoring for quantitative proteomics: a tutorial. Mol Syst Biol. 2008;4:222. doi: 10.1038/msb.2008.61. Epub Oct. 14, 2008.
Larsen et al., Assay of plasma heparin using thrombin and the chromogenic substrate H-D-Phe-Pip-Arg-pNA (S-2238). Thromb Res. Aug. 1978;13(2):285-8.
Levi et al., Matrix metalloproteinase 2 releases active soluble ectodomain of fibroblast growth factor receptor 1. Proc Natl Acad Sci U S A. 1996;93(14):7069-74.

(56) References Cited

OTHER PUBLICATIONS

Lin et al., Nanoparticles that sense thrombin activity as synthetic urinary biomarkers of thrombosis. ACS Nano. Oct. 22, 2013;7(10):9001-9. doi: 10.1021/nn403550c. Epub Sep. 12, 2013.
Mallick et al., Computational prediction of proteotypic peptides for quantitative proteomics. Nat Biotechnol. Jan. 2007;25(1):125-31. Epub Dec. 31, 2006.
Mañes et al., The matrix metalloproteinase-9 regulates the insulin-like growth factor-triggered autocrine response in DU-145 carcinoma cells. J Biol Chem. Mar. 12, 1999;274(11):6935-45.
Martinez et al., Diagnostics for the developing world: microfluidic paper-based analytical devices. Anal Chem. Jan. 1, 2010;82(1):3-10. doi: 10.1021/ac9013989.
Mira et al., Insulin-like growth factor I-triggered cell migration and invasion are mediated by matrix metalloproteinase-9. Endocrinology. Apr. 1999;140(4):1657-64.
Mirtti et al., Expression of cystatins, high molecular weight cytokeratin, and proliferation markers in prostatic adenocarcinoma and hyperplasia. Prostate. Mar. 1, 2003;54(4):290-8.
Mitchell et al., Assay for plasma heparin using a synthetic peptide substrate for thrombin: introduction of the fluorophore aminoisophthalic acid, dimethyl ester. Thromb Res. Jul. 1978;13(1):47-52.
Morris et al., Urine and plasma levels of fibrinopeptide B in patients with deep vein thrombosis and pulmonary embolism. Thromb Res. May 1, 2003;110(2-3):159-65.
Nagase et al., Matrix metalloproteinases. J Biol Chem. Jul. 30, 1999;274(31):21491-4.
Nomura et al., Activity-based protein profiling for biochemical pathway discovery in cancer. Nat Rev Cancer. Sep. 2010;10(9):630-8. doi: 10.1038/nrc2901. Epub Aug. 12, 2010.
Olson et al., In vivo fluorescence imaging of atherosclerotic plaques with activatable cell-penetrating peptides targeting thrombin activity. Integr Biol (Camb). Jun. 2012;4(6):595-605. doi: 10.1039/c2ib00161f. Epub Apr. 26, 2012.
Park et al., Magnetic Iron Oxide Nanoworms for Tumor Targeting and Imaging. Adv Mater. May 5, 2008;20(9):1630-1635.
Park et al., Systematic surface engineering of magnetic nanoworms for in vivo tumor targeting. Small. Mar. 2009;5(6):694-700. doi: 10.1002/smll.200801789.
Peer et al., Nanocarriers as an emerging platform for cancer therapy. Nat Nanotechnol. Dec. 2007;2(12):751-60.
Pomerantz et al., Determination of oligonucleotide composition from mass spectrometrically measured molecular weight. J Am Soc Mass Spectrom. Mar. 1993;4(3):204-9. doi: 10.1016/1044-0305(93)85082-9.
Posthuma-Trumpie et al., Lateral flow (immuno)assay: its strengths, weaknesses, opportunities and threats. A literature survey. Anal Bioanal Chem. Jan. 2009;393(2):569-82. doi: 10.1007/s00216-008-2287-2. Epub Aug. 13, 2008.
Powell et al., The metalloproteinase matrilysin proteolytically generates active soluble Fas ligand and potentiates epithelial cell apoptosis. Curr Biol. Dec. 16-30, 1999;9(24):1441-7.
Rajah et al., Elevated levels of the IGF-binding protein protease MMP-1 in asthmatic airway smooth muscle. Am J Respir Cell Mol Biol. Feb. 1999;20(2):199-208.
Rennke, How does glomerular epithelial cell injury contribute to progressive glomerular damage? Kidney Int Suppl. Feb. 1994;45:S58-63.
Rijkers et al., Design and synthesis of thrombin substrates with modified kinetic parameters. Thromb Res. Sep. 15, 1995 ;79(5-6):491-9.
Roepstorff et al., Proposal for a common nomenclature for sequence ions in mass spectra of peptides. Biomed Mass Spectrom. Nov. 1984;11(11):601
Ross et al., Multiplexed protein quantitation in *Saccharomyces cerevisiae* using amine-reactive isobaric tagging reagents. Mol Cell Proteomics. Dec. 2004;3(12):1154-69. Epub Sep. 22, 2004.
Ruoslahti et al., Targeting of drugs and nanoparticles to tumors. J Cell Biol. Mar. 22, 2010;188(6):759-68. doi: 10.1083/jcb.200910104. Epub Mar. 15, 2010.
Santini et al., A controlled-release microchip. Nature. Jan. 28, 1999;397(6717):335-8.
Schönbeck et al., Generation of biologically active IL-1 beta by matrix metalloproteinases: a novel caspase-1-independent pathway of IL-1 beta processing. J Immunol. Oct. 1, 1998;161(7):3340-6.
Shariat et al., Urine detection of survivin is a sensitive marker for the noninvasive diagnosis of bladder cancer. J Urol. Feb. 2004;171(2 Pt 1):626-30.
Smith et al., Rapid identification of highly active and selective substrates for stromelysin and matrilysin using bacteriophage peptide display libraries. J Biol Chem. Mar. 24, 1995;270(12):6440-9.
Suzuki et al., Matrix metalloproteinase-3 releases active heparin-binding EGF-like growth factor by cleavage at a specific juxtamembrane site. J Biol Chem. Dec. 12, 1997;272(50):31730-7.
Thompson et al., Tandem mass tags: a novel quantification strategy for comparative analysis of complex protein mixtures by MS/MS. Anal Chem. Apr. 15, 2003;75(8):1895-904. Erratum in: Anal Chem. Sep. 15, 2003;75(18):4942. Johnstone, R [added]. Anal Chem. Jun. 15, 2006;78(12):4235. Mohammed, A Karim A [added].
Truong et al., Isotope-coded chemical reporter and acid-cleavable affinity reagents for monitoring protein sulfenic acids. Bioorg Med Chem Lett. Sep. 1, 2011;21(17):5015-20. doi: 10.1016/j.bmcl.2011.04.115. Epub May 3, 2011.
Tung et al., A novel near-infrared fluorescence sensor for detection of thrombin activation in blood. Chembiochem. Mar. 1, 2002;3(2-3):207-11.
Weissleder et al., In vivo imaging of tumors with protease-activated near-infrared fluorescent probes. Nat Biotechnol. Apr. 1999;17(4):375-8.
Welser et al., Protease responsive nanoprobes with tethered fluorogenic peptidyl 3-arylcoumarin substrates. Chem Commun (Camb). Feb. 14, 2009;(6):671-3. Epub Dec. 8, 2008.
Welser et al., Protease sensing with nanoparticle based platforms. Analyst. Jan. 7, 2011;136(1):29-41. doi: 10.1039/c0an00429d. Epub Sep. 28, 2010.
Whiteaker et al., An automated and multiplexed method for high throughput peptide immunoaffinity enrichment and multiple reaction monitoring mass spectrometry-based quantification of protein biomarkers. Mol Cell Proteomics. Jan. 2010;9(1):184-96. doi: 10.1074/mcp.M900254-MCP200. Epub Oct. 20, 2009.
Whiteaker et al., Antibody-based enrichment of peptides on magnetic beads for mass-spectrometry-based quantification of serum biomarkers. Anal Biochem. Mar. 1, 2007;362(1):44-54. Epub Dec. 20, 2006.
Whitney et al., Ratiometric activatable cell-penetrating peptides provide rapid in vivo readout of thrombin activation. Angew Chem Int Ed Engl. Jan. 2, 2013;52(1):325-30. doi: 10.1002/anie.201205721. Epub Oct. 18, 2012.
Wollscheid et al., Mass-spectrometric identification and relative quantification of N-linked cell surface glycoproteins. Nat Biotechnol. Apr. 2009;27(4):378-86. doi: 10.1038/nbt.1532. Epub Apr. 6, 2009. Erratum in: Nat Biotechnol. Sep. 2009;27(9):864.
Yager et al., Point-of-care diagnostics for global health. Annu Rev Biomed Eng. 2008;10:107-44. doi: 10.1146/annurev.bioeng.10.061807.160524.
Yu et al., Cell surface-localized matrix metalloproteinase-9 proteolytically activates TGF-beta and promotes tumor invasion and angiogenesis. Genes Dev. Jan. 15, 2000;14(2):163-76.
Zhang et al., Identification and quantification of N-linked glycoproteins using hydrazide chemistry, stable isotope labeling and mass spectrometry. Nat Biotechnol. Jun. 2003;21(6):660-6. Epub May 18, 2003.
Zieske, A perspective on the use of iTRAQ reagent technology for protein complex and profiling studies. J Exp Bot. 2006;57(7):1501-8. Epub Mar. 30, 2006.
International Preliminary Report on Patentability for Application No. PCT/US2012/029200 dated Sep. 26, 2013.
Chen et al., A unique substrate recognition profile for matrix metalloproteinase-2. J Biol Chem. Feb. 8, 2002;277(6):4485-91.
Farrell et al., Non-motor parkinsonian pathology in aging A53T α-synuclein mice is associated with progressive synucleinopathy and altered enzymatic function. J Neurochem. Feb. 2014;128(4):536-46. doi: 10.1111/jnc.12481. Epub Nov. 20, 2013.

(56) References Cited

OTHER PUBLICATIONS

PCT/US2012/029200, Sep. 26, 2013, International Preliminary Report on Patentability.

Lin et al., Drug-induced amplification of nanoparticle targeting to tumors. Nano Today. Oct. 2014;9(5):550-559. doi:10.1016/j.nantod.2014.09.001. Epub Sep. 23, 2014.

Schuerle et al., Magnetically Actuated Protease Sensors for in Vivo Tumor Profiling. Nano Lett. Oct. 12, 2016;16(10):6303-6310. Epub Sep. 13, 2016.

U.S. Appl. No. 16/099,147, filed Nov. 5, 2018, Bhatia et al.

U.S. Appl. No. 16/091,145, filed Oct. 4, 2018, Bhatia et al.

U.S. Appl. No. 16/159,340, filed Oct. 12, 2018, Dudani et al.

Invitation to Pay Additional Fees dated Jan. 4, 2019 for Application No. PCT/US2018/055557.

International Search Report and Written Opinion dated Feb. 25, 2019 for Application No. PCT/US2018/055557.

Böhm et al., uPA/PAI-1 ratios distinguish benign prostatic hyperplasia and prostate cancer. J Cancer Res Clin Oncol. Jul. 2013;139(7):1221-8. doi: 10.1007/s00432-013-1428-y. Epub Apr. 18, 2013.

Dennis et al., Albumin binding as a general strategy for improving the pharmacokinetics of proteins. J Biol Chem. Sep. 20, 2002;277(38):35035-43. Epub Jul. 15, 2002.

Deshpande et al., Current trends in the use of liposomes for tumor targeting. Nanomedicine (Lond). Sep. 2013;8(9):1509-28. doi:10.2217/nnm.13.118.

Dudani et al., Classification of prostate cancer using a protease activity nanosensor library. Proc Natl Acad Sci U S A. Sep. 4, 2018;115(36):8954-8959. doi: 10.1073/pnas.1805337115. Epub Aug. 20, 2018.

Dudani et al., Harnessing Protease Activity to Improve Cancer Care. Ann Rev Cancer Biol. Mar. 2018;2:353-376.

Dudani et al., Photoactivated Spatiotemporally-Responsive Nanosensors of in Vivo Protease Activity. ACS Nano. Dec. 22, 2015;9(12):11708-17. doi: 10.1021/acsnano.5b05946. Epub Nov. 13, 2015.

Dudani et al., Sustained-release synthetic biomarkers for monitoring thrombosis and inflammation using point-of-care compatible readouts. Adv Funct Mater. May 3, 2016;26(17):2919-2928. doi: 10.1002/adfm.201505142. Epub Mar. 22, 2016.

Gartrell et al., Managing bone metastases and reducing skeletal related events in prostate cancer. Nat Rev Clin Oncol. Jun. 2014;11(6):335-45. doi: 10.1038/nrclinonc.2014.70. Epub May 13, 2014. Review. Erratum in: Nat Rev Clin Oncol. Jan. 2015;12(1). doi:10.1038/nrclinonc.2014.70.

Kaminskas et al., Methotrexate-conjugated PEGylated dendrimers show differential patterns of deposition and activity in tumor-burdened lymph nodes after intravenous and subcutaneous administration in rats. Mol Pharm. Feb. 2, 2015;12(2):432-43. doi: 10.1021/mp500531e. Epub Jan. 20, 2015.

Klotz et al., Management of low risk prostate cancer-active surveillance and focal therapy. Nat Rev Clin Oncol. Jun. 2014;11(6):324-34. doi: 10.1038/nrclinonc.2014.73. Epub May 13, 2014.

Ku et al., In vivo sensing of proteolytic activity with an NSET-based NIR fluorogenic nanosensor. Biosens Bioelectron. Mar. 15, 2016;77:471-7. doi: 10.1016/j.bios.2015.09.067. Epub Sep. 30, 2015.

Kwon et al., Ultrasensitive tumour-penetrating nanosensors of protease activity. Nat Biomed Eng. 2017;1. pii: 0054. doi:10.1038/s41551-017-0054. Epub Apr. 10, 2017.

Lebeau et al., Imaging active urokinase plasminogen activator in prostate cancer. Cancer Res. Apr. 1, 2015;75(7):1225-35. doi:10.1158/0008-5472.CAN-14-2185. Epub Feb. 11, 2015.

McLennan et al., Subcutaneous drug delivery and the role of the lymphatics. Drug Discov Today Technol. 2005 Spring;2(1):89-96. doi:10.1016/j.ddtec.2005.05.006.

Morgia et al., Matrix metalloproteinases as diagnostic (MMP-13) and prognostic (MMP-2, MMP-9) markers of prostate cancer. Urol Res. Feb. 2005;33(1):44-50. Epub Oct. 22, 2004.

Prensner et al., Beyond PSA: the next generation of prostate cancer biomarkers. Sci Transl Med. Mar. 28, 2012;4(127):127rv3. doi:10.1126/scitranslmed.3003180.

Sawyers, The cancer biomarker problem. Nature. Apr. 3, 2008;452(7187):548-52. doi: 10.1038/nature06913.

Stein et al., Ultrasensitive Scaffold-Dependent Protease Sensors with Large Dynamic Range. ACS Synth Biol. Jul. 21, 2017;6(7):1337-1342. doi: 10.1021/acssynbio.6b00370. Epub Mar. 28, 2017.

Sugahara et al., Coadministration of a tumor-penetrating peptide enhances the efficacy of cancer drugs. Science. May 21, 2010;328(5981):1031-5. doi:10.1126/science.1183057. Epub Apr. 8, 2010.

Sutherland et al., RGD-Binding Integrins in Prostate Cancer: Expression Patterns and Therapeutic Prospects against Bone Metastasis. Cancers (Basel). Oct. 26, 2012;4(4):1106-45. doi:10.3390/cancers4041106.

Taylor et al., Integrative genomic profiling of human prostate cancer. Cancer Cell. Jul. 13, 2010;18(1):11-22. doi:10.1016/j.ccr.2010.05.026. Epub Jun. 24, 2010.

Thorek et al., Internalization of secreted antigen-targeted antibodies by the neonatal Fc receptor for precision imaging of the androgen receptor axis. Sci Transl Med. Nov. 30, 2016;8(367):367ra167.

Traxlmayr et al., Strong Enrichment of Aromatic Residues in Binding Sites from a Charge-neutralized Hyperthermostable Sso7d Scaffold Library. J Biol Chem. Oct. 21, 2016;291(43):22496-22508. Epub Aug. 30, 2016.

Withana et al., Labeling of active proteases in fresh-frozen tissues by topical application of quenched activity-based probes. Nat Protoc. Jan. 2016;11(1):184-91. doi: 10.1038/nprot.2016.004. Epub Dec. 30, 2015.

Xia et al., Multiplex detection of protease activity with quantum dot nanosensors prepared by Intein-Mediated specific bioconjugation. Analytical Chemistry. Nov. 15, 2008; 22(80) 8649-8655.

* cited by examiner

AFFINITY-BASED DETECTION OF LIGAND-ENCODED SYNTHETIC BIOMARKERS

RELATED APPLICATIONS

This application claims priority under 35 U.S.C. § 119(e) to U.S. Provisional Application Ser. No. 61/832,766, entitled "AFFINITY-BASED DETECTION OF LIGAND-ENCODED SYNTHETIC BIOMARKERS" filed on Jun. 7, 2013, which is herein incorporated by reference in its entirety.

FIELD OF THE INVENTION

The present invention relates to methods and products associated with detecting and monitoring the activity of proteases in vivo using affinity assays. These methods and products form the basis of and may be used as an ultrasensitive diagnostic platform. The invention also relates to products, kits, and databases for use in the methods of the invention.

BACKGROUND OF THE INVENTION

Urine has a rich and longstanding clinical history as a source for monitoring developing conditions and remains an integral component of a health examination.[1] Well over one hundred tests can be performed to indicate conditions as diverse as pregnancy,[2] diabetes,[3] kidney diseases,[4] metabolic disorders and others. Inspired by the elegant physiology of the renal system—which has evolved the capacity to selectively filter liters of blood within minutes to remove byproducts of biological processes—we recently developed a class of protease-sensitive nanoparticles, called 'synthetic biomarkers', that in response to dysregulated protease activity at the sites of disease, release reporters into the circulation that are then concentrated into the host urine for noninvasive monitoring, using multiplexing techniques such as mass spectrometry for detection.[6] Dysregulation of proteases in cancer has important consequences in cell signaling and helps drive cancer cell proliferation, invasion, angiogenesis, avoidance of apoptosis, and metastasis. In murine models of liver fibrosis and cancer, synthetic urinary biomarkers removed the need for invasive monitoring of solid organs by core biopsies, and significantly improved early stage detection of cancer compared to a tumor-secreted blood biomarker.

SUMMARY OF THE INVENTION

The invention in some aspects is a method involving administering to a subject a biomarker nanoparticle, wherein the biomarker nanoparticle comprises a modular structure having a carrier domain linked to an enzyme susceptible detectable marker, wherein the enzyme susceptible detectable marker is comprised of an enzyme susceptible domain linked to a detectable marker whereby the detectable marker is capable of being released from the biomarker nanoparticle when exposed to an enzyme and wherein the detectable marker comprises a capture ligand and a detection ligand connected by a linker; identifying a biological sample for detection of the marker, wherein the biological sample is at a body site that is remote from a body site where the detectable marker is released from the biomarker nanoparticle; and, analyzing the biological sample using a capture assay in order to detect the presence of the detectable marker, wherein the presence of the detectable marker in the biological sample is indicative of the enzyme being present in an active form within the subject.

In some embodiments the capture ligand is linked to the enzyme susceptible domain. In other embodiments the detection ligand is linked to the enzyme susceptible domain. The linker may be, for instance, a polymer such as PEG, a protein, a peptide, a polysaccharide, a nucleic acid, or a small molecule. In some embodiments the linker is a protein of 10-100 amino acids in length. In other embodiments the linker is GluFib (SEQ ID NO. 1).

The capture assay in some embodiments involves a detection step selected from the group consisting of an ELISA, including fluorescent, colorimetric, bioluminescent and chemiluminescent ELISAs, a paper test strip, bead-based fluorescent assay, and label-free detection, such as surface plasmon resonance (SPR). The capture assay may involve, for instance, binding of the capture ligand to an affinity agent. The capture ligand in some embodiments is a protein, peptide, a polysaccharide, a nucleic acid, a fluorescent molecule, or a small molecule. For instance the capture ligand may be biotin and the affinity agent may be streptavidin or the capture ligand may be streptavidin and the affinity agent may be biotin. The analysis method in some embodiments is a multiplex analysis method.

In some embodiments the detection ligand is a protein, peptide, a polysaccharide, a nucleic acid, a fluorescent molecule, or a small molecule. In other embodiments the detection ligand or the capture ligand is selected form the group consisting of Alexa488, TAMRA, DNP, fluorescein, OREGON GREEN® (4-(2,7-difluoro-6-hydroxy-3-oxo-3H-xanthen-9-YL)isophthalic acid), TEXAS RED® (sulforhodamine 101 acid chloride), Dansyl, BODIPY® (borondipyrromethene), Alexa405, CASCADE BLUE® (Acetic acid, [(3,6,8-trisulfo-1-pyrenyl)oxy]-, 1-hydrazide, trisodium salt), Lucifer Yellow, Nitrotyrosine, HA-tag, FLAG-tag, His-tag, Myc-tag, V5-tag, S-tag, biotin.

The affinity agent may be selected from the group consisting of antibodies, antibody fragments, aptamers, magnetic beads conjugated with Abs, protein or peptides on an affinity column. In some embodiments the affinity agent is immobilized on a surface, such as, for instance, a bead. In other embodiments the affinity agent is in a solution.

The biomarker nanoparticle may be administered to the subject by any route. For instance it may be administered intravenously, orally, transdermally or through an implant.

The carrier in some embodiments is a particle such as a nanoparticle, protein, peptide or a polysaccharide or a synthetic polymer.

In some embodiments the enzyme is a cancer related enzyme. In other embodiments the enzyme is a protease or a glycosidase.

The method may also include the step of collecting the biological sample from the subject, wherein the biological sample is urine, blood, saliva, or mucous secretion.

A plurality of biomarker nanoparticles having a plurality of enzyme susceptible detectable markers are administered to the subject in some embodiments. In other embodiments the biomarker nanoparticle has a plurality of enzyme susceptible detectable markers. For instance, the plurality of enzyme susceptible detectable markers comprise a plurality of capture ligands and a single type of detection ligand in some embodiments. The plurality of capture ligands include 2-1,000, 2-100 or 2-10 different capture ligands. In other embodiments the plurality of enzyme susceptible detectable markers comprise a single type of capture ligand and a plurality of detection ligands.

The enzyme susceptible detectable marker is susceptible to modification by an enzyme, cleavage by a protease, or addition of a detectable component by the enzyme associated with a disease or condition in some embodiments. In other embodiments the enzyme susceptible detectable marker is susceptible to modification by an enzyme, cleavage by a protease, or addition of a detectable component by the enzyme not associated with a disease or condition, but associated with a normal condition.

In some embodiments the disease or condition is cancer, cardiovascular disease, arthritis, viral, bacterial, parasitic or fungal infection, Alzheimer's disease emphysema, thrombosis, hemophilia, stroke, organ dysfunction, any inflammatory condition, vascular disease, parenchymal disease, or a pharmacologically-induced state.

In some embodiments the method involves a purification step, wherein the detectable marker is isolated from other components in the biological sample.

In other embodiments the method is a method for diagnosing a disease in the subject and the presence of the detectable marker in the subject is indicative of the subject having the disease and the absence of the detectable marker in the subject is indicative of the subject not having the disease.

In other embodiments the method involves administering to the subject a free reporter in order to normalize the detection signal.

A method involving collecting a urine sample from a subject suspected of having a disorder or condition, wherein the subject has been administered a biomarker nanoparticle, wherein the biomarker nanoparticle comprises a modular structure having a carrier domain linked to an enzyme susceptible detectable marker, wherein the enzyme susceptible detectable marker is comprised of an enzyme susceptible domain linked to a detectable marker whereby the detectable marker is capable of being released from the biomarker nanoparticle when exposed to an enzyme and wherein the detectable marker comprises a capture ligand and a detection ligand connected by a linker; and, subjecting the urine sample to analysis method by a capture assay, wherein the capture assay involves an affinity step where an affinity agent binds to the capture ligand and a detection step, wherein the detection ligand is detected in order to detect the presence of the ligand marker, and wherein the presence or absence of the ligand marker in the biological sample is indicative of the disorder or condition within the subject is provided according to aspects of the invention.

The detection step in some embodiments is selected from the group consisting of an ELISA assay, including chemiluminescent ELISA and bioluminescent ELISA, a paper test strip, bead-based fluorescent assay, and label-free detection, such as surface plasmon resonance (SPR). In other embodiments the affinity agent is selected from the group consisting of antibodies, antibody fragments, aptamers, magnetic beads conjugated with Abs, protein or peptides on an affinity column. In other embodiments the method involves administering a therapeutic agent to the subject to treat the disorder or condition.

According to other aspects of the invention a composition comprising a transdermal patch having a drug delivery compartment, wherein the drug delivery compartment includes a biomarker nanoparticle, wherein the biomarker nanoparticle comprises a modular structure having a carrier domain linked to an enzyme susceptible detectable marker that is capable of being released from the biomarker nanoparticle when exposed to an enzyme is provided. The enzyme susceptible detectable marker may be comprised of an enzyme susceptible domain linked to a detectable marker and wherein the detectable marker comprises a capture ligand and a detection ligand connected by a linker.

A reagent is provided according to other aspects of the invention. The reagent includes a biomarker nanoparticle, wherein the biomarker nanoparticle comprises a modular structure having a carrier domain linked to an enzyme susceptible detectable marker, wherein the enzyme susceptible detectable marker is comprised of an enzyme susceptible domain linked to a detectable marker whereby the detectable marker is capable of being released from the biomarker nanoparticle when exposed to an enzyme and wherein the detectable marker comprises a capture ligand and a detection ligand connected by a linker.

In some embodiments the capture ligand is linked to the enzyme susceptible domain and in other embodiments the detection ligand is linked to the enzyme susceptible domain. The capture assay may involve binding of the capture ligand to an affinity agent.

A composition is provided according to other aspects of the invention. The composition includes a biomarker nanoparticle, wherein the biomarker nanoparticle comprises a modular structure having a carrier domain linked to an enzyme susceptible detectable marker that is capable of being released from the biomarker nanoparticle when exposed to an enzyme and a free reporter. The enzyme susceptible detectable marker may be comprised of an enzyme susceptible domain linked to a detectable marker and wherein the detectable marker comprises a capture ligand and a detection ligand connected by a linker. In some embodiments the free reporter is a protein, peptide or polysaccharide.

In yet other aspects the invention is a kit having a container housing a biomarker nanoparticle, wherein the biomarker nanoparticle comprises a modular structure having a carrier domain linked to an enzyme susceptible detectable marker, wherein the enzyme susceptible detectable marker is comprised of an enzyme susceptible domain linked to a detectable marker whereby the detectable marker is capable of being released from the biomarker nanoparticle when exposed to an enzyme and wherein the detectable marker comprises a capture ligand and a detection ligand connected by a linker; and, instructions for administering the nanoparticle to a subject and for analyzing a biological sample of the subject to detect the presence or absence of the ligand marker generated by administration of the nanoparticle by a capture assay.

In some embodiments the kit further includes one or more containers housing a free reporter, an affinity agent, such as antibodies, antibody fragments, aptamers, magnetic beads conjugated with Abs, proteins or peptides on an affinity column, and a detection reagent such as a reagent for an assay selected from the group consisting of an ELISA assay, including chemiluminescent ELISA and bioluminescent ELISA, a paper test strip, bead-based fluorescent assay, and label-free detection, such as surface plasmon resonance (SPR).

In another aspect the invention is a method involving administering to a subject a microdose of a biomarker nanoparticle, wherein a detectable marker is released from the biomarker nanoparticle when exposed to an enzyme; and analyzing a biological sample using a capture assay in order to detect the presence of the detectable marker, wherein the presence of the detectable marker in the biological sample is indicative of the enzyme being present in an active form within the subject. In some embodiments the microdose is less than 100 micrograms. In other embodiments the biological sample is at a body site that is remote from a body site where the detectable marker is released from the biomarker nanoparticle, such as urine. In yet other embodiments the biomarker nanoparticle comprises a modular structure having a carrier domain linked to an enzyme susceptible detectable marker, wherein the enzyme susceptible detectable marker is comprised of an enzyme susceptible domain linked to the detectable marker. Optionally, the detectable marker comprises a capture ligand and a detection ligand connected by a linker.

Each of the embodiments of the invention can encompass various recitations made herein. It is, therefore, anticipated that each of the recitations of the invention involving any one element or combinations of elements can, optionally, be included in each aspect of the invention.

DETAILED DESCRIPTION OF THE INVENTION

Figure 1:
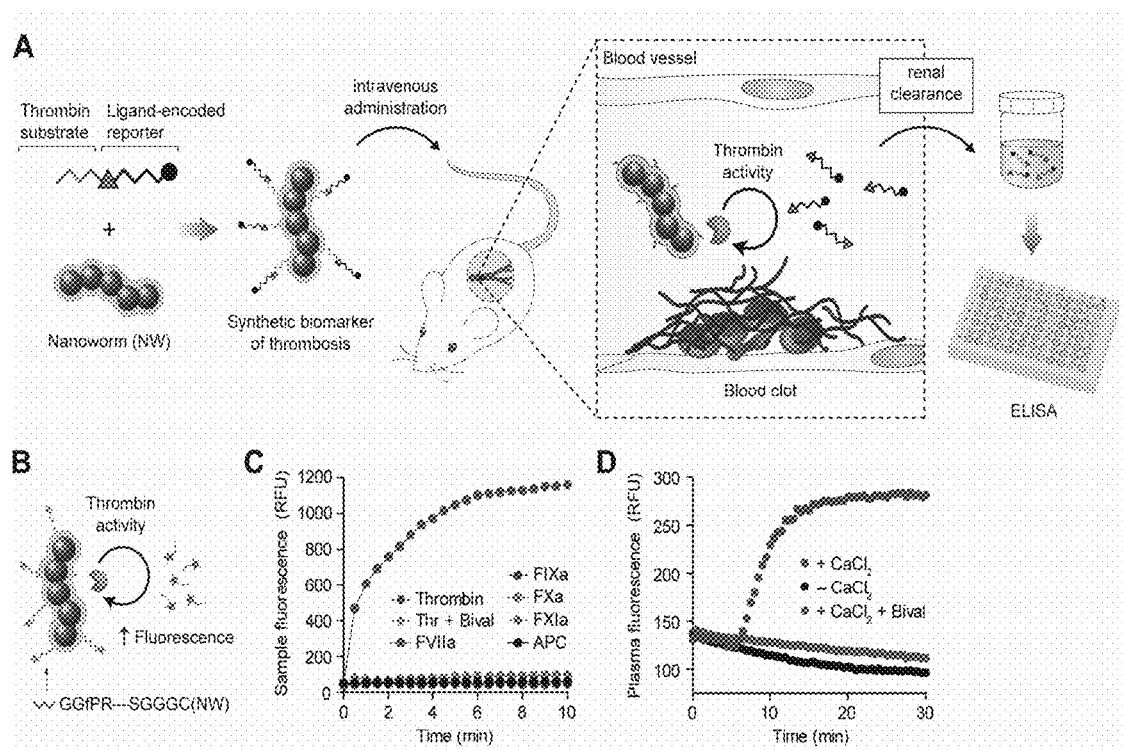
FIGS. 1A-D shows the (A) schematic of approach. Synthetic biomarkers composed of NWs conjugated with a thrombin-sensitive substrate in tandem with a ligand-encoded reporter. These agents survey the vasculature for the formation of blood clots where thrombin activity cleaves and releases the reporters into urine for analysis by ELISA. (B) Schematic of fluorogenic NW assay for detecting protease activity. (C) Kinetics of fluorogenic activity in response to coagulation proteases (n=3 per condition). Thr, thrombin; Bival, bivalirudin. (D) Kinetics of fluorogenic activity in plasma after the addition of $CaCl_2$ to activate clotting (n=3 per condition).

Rapid, simple and reliable assays for assessing information on a biological process or system are provided according to the invention. The status of physiological conditions of a subject can be assessed using the methods of the invention by identifying molecular properties associated with enzymatic activity. This may now be accomplished using the methods of the invention in the context of widely available assays that are not as restrictive as mass spectrometry. The detection of enzymatic activity is useful for diagnosing diseases such as cancer, thrombosis, fibrosis, infectious disease, rheumatoid arthritis and arteriosclerosis, as well as for prognostic indicators. Uses also include monitoring enzymatic activities such as kinases, phosphatases, nucleases, and others. The response of most cancers to medical intervention is currently monitored by physical exams and various clinical imaging modalities. A few cancers such as prostate and ovarian cancer are monitored by use of single biomarkers in the blood. Such diagnostic techniques are achieved, for instance using fluorescence detection of molecular markers which are activated in a particular disease state. More complex assays typically involve the use of elaborate technology and equipment such as in mass spectrometry. Thus, the invention has a wide range of commercial applications in molecular diagnostics (e.g. early cancer detection) as well as applications in basic science research (e.g. profiling protease activities). For example, an ELISA test for cancer may have immediate clinical applications for early stage screening or for monitoring recurrence. Similarly, a paper based test would have a number of commercial applications for in-home monitoring (similar to home pregnancy tests) as well as to provide low-cost diagnostics for global health. In summary, this invention enables commercial applications precluded by current technologies and methods.

By harnessing the capacity of the biomarker nanoparticles to circulate and sense the local microenvironment, we have engineered synthetic biomarkers that can detect enzymatic activity in vivo and noninvasively quantify the physiological processes. For instance, as shown in the Examples herein thrombin activity can be assessed in order to determine the aggregate amount of active clots. Unlike other nanoparticle sensors that function by producing a localized signal,[9-10,23] the compositions of the invention sense protease activity by releasing reporters locally at the sites of interest, i.e., where thrombi are formed but then are filtered and detected remotely from the urine. By using distinct ligands and their cognate binding molecules, a panel of heterobifunctionalized reporters were also developed that can be detected using assays such as standardized 96-well plate assays, removing the need for mass spectrometry as described in our previous study.[6] This system is readily extensible by incorporating additional ligand-capture agent pairs and is amenable for detection by other methods including paper-based test strips (lateral flow assays) at the point of care, assays including bead-based assays (e.g., immunoprecipitation), surface plasmon resonance, nanoelectronics (e.g., nanowires) etc.

The methods of the invention have a number of advantages over the prior art methods. For instance, using the methods of the invention it is now possible to detect enzymatic activity in a livening subject with ultrasensitive detection platforms which allow for microdosing in a subject. Currently, microdosing studies are carried out in which trace doses of drug (usually one hundredth of pharmacological dose to a maximum of 100 ug) are administered to human subjects to obtain basic parameters such as clearance, organ distribution, plasma half-time and others that are unobtainable with preclinical animal models. Most drugs administered to a subject or patient in microdoses are safe. Consequently 'phase 0' studies can be conducted with fewer regulations compared to traditional FDA-guided clinical trials. In order for microdosing studies to be feasible, however, ultrasensitive analytical methods are required to detect the target analyses. The methods of the invention provide a platform of ligand-encoded reporters that can be readily detected by established and emerging ultrasensitive analytical platforms. Even the prior work of the inventors involving mass spectrometry based methods for detecting enzymatic activity in vivo are not sensitive enough for microdosing. For example, the mass spectrometry based methods require a baseline of 1 mg/kg dosing for accurate detection. The methods of the invention enable dosing at levels below $1/100^{th}$ of this baseline levels as well as well below 100 micrograms, with extremely accurate results. These results are quite unexpected.

The sensitivity of the assays of the invention, in some aspects, derive from a combination of the unique structure of the biomarker nanoparticle and the capture-detection techniques. The structure of the biomarker nanoparticle is composed of a core or carrier component that is decorated with a marker that has a structure having dual ligands connected to one another by a linker and connected to the carrier through an enzyme susceptible component. The marker is cleaved and separated from the carrier by exposure to a functional enzyme in vivo. It then travels to peripheral body sites such as urine, where it can be captured and detected using the techniques of the invention. The capture step involves a binding interaction between a capture reagent and one of the ligands. The other ligand can then be detected by a variety of methods. The ability to promote release of, and then capture and detect the marker using simple easily accessible assays results in the ultrasensitive techniques described herein.

Currently, detecting protease activities in living organisms is typically performed with 'activity-based' probes that are designed to emit fluorescent signals following peptide cleavage (Baruch et al. Trends Cell Biol 2004, Blum et al. Nat Chem Biol 2007, Nomura et al. Nat Rev Cancer 2010). The ability of these agents to monitor distinct cleavage events simultaneously, or multiplexing, is in part limited by the challenges of designing their emission spectra to be distinct and within the near infrared window (600-900 nm) to minimize signal attenuation from tissue scattering. Surprisingly, the ability to engineer hundreds of uniquely encoded agents—and therefore, many new diagnostic tests has been accomplished with the methods of the invention.

The inventors previously developed a method utilitzing mass 'barcodes' to label nanoparticles and allow multiplexed monitoring of protease activities by mass spectrometry. Although modem mass spectrometers can readily detect the presence of hundreds of unique peptides within a complex sample (i.e. multiplexing is not a fundamental limitation), these instruments are expensive, require specific technical expertise, and not readily available in most clinical settings. It was discovered according to the invention that a nanoparticle based system for highly sensitive and rapid detection of in vivo enzyme status could be achieved using affinity based assays such as ELISA and Lateral flow assays (LFA).

Lateral flow assays (LFA), also referred to herein as paper test strip assays, have been used for nearly 40 years as the standard test for pregnancy. An additional advantage of LFAs is that they do not require laboratory infrastructure. The assay is automated on the test strip, only requiring the user to apply sample to the sample pad, and the results can be read with the naked eye by inspection of a distinct colored stripe. For these reasons LFAs can be used in almost any setting. In the developed world, one potential implementation includes an injection of the biomarker nanoparticles at the clinic and then measurement by the patient at home later. LFAs, or rapid diagnostic tests RDT, have been developed for a number of diseases, including malaria and AIDS. For much of the developing world, however, the burden of infectious diseases is falling, while non-communicable diseases, such as cancer, are increasing. Unfortunately, LFAs for many diseases remain elusive due to the low level of endogenous biomarkers. The methods of the invention, using an LFA to measure protease-sensitive synthetic probes, provides a unique opportunity to diagnose cancer significantly earlier in places, like rural India and China, where a lack of medical infrastructure would otherwise make early diagnosis intractable.

The invention relates to a platform for functional characterization of disease or condition specific enzymatic repertoire as a method to monitor both disease progression and regression as well as response to therapeutics. The methods provide orders of magnitude more in vivo enzyme-substrate information than current technologies or in view of the mass spectrometry techniques provide simpler more efficient methods. The platform provides a unique opportunity to functionally monitor cancer and other disease progression and response to therapy. It is particularly useful for prolonged therapeutic regimens, where the discovery of prognostic functional signatures would greatly assist intervention and where enzymatic signatures directly correlate to therapeutic efficacy.

By administering a biomarker nanoparticle, such as an exogenous detectable substrate library into animal models of disease it is possible to gain information into substrate specific enzymatic activities associated with diseases, such as cancer, cardiovascular disease, arthritis, and others. The technology allows for the potential simultaneous profiling of hundreds of enzyme-substrate activities in vivo using, for instance, -chaperoned, enzyme sensitive detectable compounds, an example of a compound referred to as biomarker nanoparticles. The method leverages the distinct pharmacokinetics of modular structures and small, optionally hydrophilic, marker peptides (RES and renal clearance, respectively). The biomarker nanoparticles have long circulation times and thus remain in circulation or permeate into tumors via porous angiogenic vascular networks, where upon local molecules, such as enzymes (MMPs, kallikreins, cathepsins, plasminogen activators, ADAMs) gain access to the enzyme susceptible regions of the biomarker nanoparticles or substrates gain access to the enzymes of the biomarker nanoparticles.

When the biomarker nanoparticles, for example, the reagents including an enzyme susceptible domain are exposed to enzymes, for instance, proteases, the reagent is cleaved, such that a marker, referred to herein as an enzyme susceptible detectable marker, is released. The marker is renally-cleared and thus functions as a "messenger" of enzyme activity. Urine analysis can generate data that is organized into a barcode of, for instance, cancer enzyme activity. In the absence of enzyme activity the biomarker nanoparticles remain uncleaved and the whole reagent including the detectable marker is cleared through RES organs (liver, spleen, and lymph nodes) without producing urine markers. The use of the capture assays of the invention to identify substrates allows unprecedented multiplexing capability combined with accessibility and ease of use, with the potential to assay greater than 1,000 substrates rapidly and at extremely low doses.

Thus, the invention in some aspects involves administering to a subject a biomarker nanoparticle, identifying a biological sample from the subject in which to detect the detectable marker and optionally collecting the sample; and, subjecting the biological sample to an analysis method in order to detect the presence of one or more detectable markers. The presence of the detectable marker in the biological sample is indicative of an active enzyme or a substrate within the subject. Although the invention is described herein with respect to an enzyme susceptible domain included in the carrier for detecting the presence of an enzyme in vivo, each of the methods of the invention is also useful when it is desirable to detect a substrate in vivo. In that instance the enzyme susceptible domain would contain an enzyme that is capable of acting on a substrate in vivo, provided the enzyme substrate reaction results in the release of the detectable marker. For instance if upon reaction with an in vivo substrate an enzyme underwent a conformation change that resulted in the release of the detectable marker, the marker could be detected as a signal of the presence of the substrate.

For example the invention in some aspects involves methods for administering to a subject a biomarker nanoparticle, wherein the biomarker nanoparticle comprises a modular structure having a carrier domain linked to an enzyme susceptible detectable marker, wherein the enzyme susceptible detectable marker is comprised of an enzyme susceptible domain linked to a detectable marker whereby the detectable marker is capable of being released from the biomarker nanoparticle when exposed to an enzyme and wherein the detectable marker comprises a capture ligand and a detection ligand connected by a linker; identifying a biological sample for detection of the marker, wherein the biological sample is at a body site that is remote from a body site where the detectable marker is released from the biomarker nanoparticle; and, analyzing the biological sample using a capture assay in order to detect the presence of the detectable marker, wherein the presence of the detectable marker in the biological sample is indicative of the enzyme being present in an active form within the subject.

The biomarker nanoparticle comprises a modular structure having a carrier domain linked to an enzyme susceptible detectable marker. A modular structure, as used herein, refers to a molecule having multiple domains.

The enzyme susceptible detectable marker is a portion of the modular structure that is connected to the carrier. It is composed of an enzyme susceptible domain linked to a detectable marker.

The detectable marker is capable of being released from the biomarker nanoparticle when exposed to an enzyme in vivo. The detectable marker once released is free to travel to a remote site for detection. A remote site is used herein to refer to a site in the body that is distinct from the bodily tissue housing the enzyme where the enzymatic reaction occurs. The detectable marker is composed of a capture ligand and a detection ligand connected by a linker.

The capture ligand is a molecule that is capable of being captured by a binding partner. The detection ligand is a molecule that is capable of being detected by any of a variety of methods. While the capture ligand and the detection ligand will be distinct from one another in a particular detectable marker, the class of molecules that make us capture and detection ligands overlap significantly. For instance, many molecules are capable of being captured and detected. In some instances these molecules may be detected by being captured or capturing a probe. The capture and detection ligand each independently may be one or more of the following: a protein, a peptide, a polysaccharide, a nucleic acid, a fluorescent molecule, or a small molecule, for example. In some embodiments the detection ligand or the capture ligand may be, but is not limited to, one of the following: Alexa488, TAMRA, DNP, fluorescein, OREGON GREEN® (4-(2,7-difluoro-6-hydroxy-3-oxo-3H-xanthen-9-YL)isophthalic acid), TEXAS RED® (sulforhodamine 101 acid chloride), Dansyl, BODIPY® (boron-dipyrromethene), Alexa405, CASCADE BLUE® (Acetic acid, [(3,6,8-trisulfo-1-pyrenyl)oxy]-, 1-hydrazide, trisodium salt), Lucifer Yellow, Nitrotyrosine, HA-tag, FLAG-tag, His-tag, Myc-tag, V5-tag, S-tag, biotin or streptavidin.

The capture ligand and a detection ligand are connected by a linker. The purpose of the linker is prevent steric hinderance between the two ligands. Thus, the linker may be any type of molecule that achieves this. The linker may be, for instance, a polymer such as PEG, a protein, a peptide, a polysaccharide, a nucleic acid, or a small molecule. In some embodiments the linker is a protein of 10-100 amino acids in length. In other embodiments the linker is GluFib (SEQ ID NO. 1). Optionally, the linker may be 8 nm-100 nm, 6 nm-100 nm, 8 nm-80 nm, 10 nm-100 nm, 13 nm-100 nm, 15 nm-50 nm, or 10 nm-50 nm in length. The carrier domain may include a single type of enzyme susceptible detectable marker, such as, a single type of enzyme susceptible domain and or detectable marker or it may include multiple type of enzyme susceptible detectable markers, such as, different enzyme susceptible domains and detectable markers. For instance each carrier may include 1 type of enzyme susceptible detectable marker or it may include 2-1,000 different enzyme susceptible detectable markers or any integer therebetween. Alternatively each carrier may include greater than 1,000 enzyme susceptible detectable markers. Multiple copies of the biomarker nanoparticle are administered to the subject. Some mixtures of biomarker nanoparticles may include enzyme susceptible detectable markers that are enzymes, others may be enzymatic susceptible domains, and other may be mixtures of the two. Additionally a plurality of different biomarker nanoparticles may be administered to the subject to determine whether multiple enzymes and/or substrates are present. In that instance, the plurality of different biomarker nanoparticles includes a plurality of detectable markers, such that each enzyme susceptible domain is associated with a particular detectable marker or molecules.

The carrier domain may serve as the core of the nanoparticle. A purpose of the carrier domain is to serve as a platform for the enzyme susceptible detectable marker. As such, the carrier can be any material or size as long as it can serve as a carrier or platform. Preferably the material is non-immunogenic, i.e. does not provoke an immune response in the body of the subject to which it will be administered. Another purpose is that it may function as a targeting means to target the modular structure to a tissue, cell or molecule. In some embodiments the carrier domain is a particle. A particle, for example, a nanoparticle, may, for instance, result in passive targeting to tumors by circulation. Other types of carriers, include, for instance, compounds that cause active targeting to tissue, cells or molecules. Examples of carriers include, but are not limited to, microparticles, nanoparticles, aptamers, peptides (RGD, iRGD, LyP-1, CREKA, etc.), proteins, nucleic acids, polysaccharides, polymers, antibodies or antibody fragments (e.g. herceptin, cetuximab, panitumumab, etc.) and small molecules (e.g. erlotinib, gefitinib, sorafenib, etc.).

As used herein the term "particle" includes nanoparticles as well as microparticles. Nanoparticles are defined as particles of less than 1.0 µm in diameter. A preparation of nanoparticles includes particles having an average particle size of less than 1.0 µm in diameter. Microparticles are particles of greater than 1.0 µm in diameter but less than 1 mm. A preparation of microparticles includes particles having an average particle size of greater than 1.0 µm in diameter. The microparticles may therefore have a diameter of at least 5, at least 10, at least 25, at least 50, or at least 75 microns, including sizes in ranges of 5-10 microns, 5-15 microns, 5-20 microns, 5-30 microns, 5-40 microns, or 5-50 microns. A composition of particles may have heterogeneous size distributions ranging from 10 nm to mm sizes. In some embodiments the diameter is about 5 nm to about 500 nm. In other embodiments, the diameter is about 100 nm to about 200 nm. In other embodiment, the diameter is about 10 nm to about 100 nm.

The particles may be composed of a variety of materials including iron, ceramic, metallic, natural polymer materials (including lipids, sugars, chitosan, hyaluronic acid etc), synthetic polymer materials (including poly-lactide-coglycolide, poly-glycerol sebacate, etc), and non-polymer materials, or combinations thereof.

The particles may be composed in whole or in part of polymers or non-polymer materials. Non-polymer materials, for example, may be employed in the preparation of the particles. Exemplary materials include alumina, calcium carbonate, calcium sulfate, calcium phosphosilicate, sodium phosphate, calcium aluminate, calcium phosphate, hydroxyapatite, tricalcium phosphate, dicalcium phosphate, tricalcium phosphate, tetracalcium phosphate, amorphous calcium phosphate, octacalcium phosphate, and silicates. In certain embodiments the particles may comprise a calcium salt such as calcium carbonate, a zirconium salt such as zirconium dioxide, a zinc salt such as zinc oxide, a magnesium salt such as magnesium silicate, a silicon salt such as silicon dioxide or a titanium salt such as titanium oxide or titanium dioxide.

A number of biodegradable and non-biodegradable biocompatible polymers are known in the field of polymeric biomaterials, controlled drug release and tissue engineering (see, for example, U.S. Pat. Nos. 6,123,727; 5,804,178; 5,770,417; 5,736,372; 5,716,404 to Vacanti; U.S. Pat. Nos. 6,095,148; 5,837,752 to Shastri; U.S. Pat. No. 5,902,599 to Anseth; U.S. Pat. Nos. 5,696,175; 5,514,378; 5,512,600 to Mikos; U.S. Pat. No. 5,399,665 to Barrera; U.S. Pat. No. 5,019,379 to Domb; U.S. Pat. No. 5,010,167 to Ron; U.S. Pat. No. 4,946,929 to d'Amore; and U.S. Pat. Nos. 4,806,621; 4,638,045 to Kohn; see also Langer, Acc. Chem. Res. 33:94, 2000; Langer, J. Control Release 62:7, 1999; and Uhrich et al., Chem. Rev. 99:3181, 1999; all of which are incorporated herein by reference).

Polymers include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene poly(ethylene glycol), poly (ethylene oxide), poly(ethylene terephthalate), poly(vinyl alcohols), poly(vinyl acetate, poly vinyl chloride and polystyrene.

Examples of non-biodegradable polymers include ethylene vinyl acetate, poly(meth) acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), poly(caprolactone), poly(hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. In some embodiments the polymers are polyesters, polyanhydrides, polystyrenes, polylactic acid, polyglycolic acid, and copolymers of lactic and glycoloic acid and blends thereof.

PVP is a non-ionogenic, hydrophilic polymer having a mean molecular weight ranging from approximately 10,000 to 700,000 and the chemical formula $(C_6H_9NO)[n]$. PVP is also known as poly[1-(2-oxo-1-pyrrolidinyl)ethylene], Povidone™, Polyvidone™, RP 143™, Kollidon™, Peregal ST™, Periston™, Plasdone™, Plasmosan™, Protagent™ Subtosan™, and Vinisil™. PVP is non-toxic, highly hygroscopic and readily dissolves in water or organic solvents.

Polyethylene glycol (PEG), also known as poly(oxyethylene) glycol, is a condensation polymer of ethylene oxide and water having the general chemical formula $HO(CH_2CH_2O)[n]H$.

Polyvinyl alcohol (PVA) is a polymer prepared from polyvinyl acetates by replacement of the acetate groups with hydroxyl groups and has the formula $(CH_2CHOH)[n]$. Most polyvinyl alcohols are soluble in water.

PEG, PVA and PVP are commercially available from chemical suppliers such as the Sigma Chemical Company (St. Louis, Mo.).

In certain embodiments the particles may comprise poly (lactic-co-glycolic acid) (PLGA).

The carrier may be composed of inorganic materials. Inorganic materials include, for instance, magnetic materials, conductive materials, and semiconductor materials.

In addition to particles the carrier may be composed of any organic carrier, including biological and living carriers such as cells, viruses, bacteria, as well as any non-living organic carriers, or any composition enabling exposure of enzyme substrates to enzymes in disease (including extracellular, membrane-bound, and intracellular enzymes).

In some embodiments, the particles are porous. A porous particle can be a particle having one or more channels that extend from its outer surface into the core of the particle. In some embodiments, the channel may extend through the particle such that its ends are both located at the surface of the particle. These channels are typically formed during synthesis of the particle by inclusion followed by removal of a channel forming reagent in the particle.

The size of the pores may depend upon the size of the particle. In certain embodiments, the pores have a diameter of less than 15 microns, less than 10 microns, less than 7.5 microns, less than 5 microns, less than 2.5 microns, less than 1 micron, less than 0.5 microns, or less than 0.1 microns. The degree of porosity in porous particles may range from greater than 0 to less than 100% of the particle volume. The degree of porosity may be less than 1%, less than 5%, less than 10%, less than 15%, less than 20%, less than 25%, less than 30%, less than 35%, less than 40%, less than 45%, or less than 50%. The degree of porosity can be determined in a number of ways. For example, the degree of porosity can be determined based on the synthesis protocol of the carriers (e.g., based on the volume of the aqueous solution or other channel-forming reagent) or by microscopic inspection of the carriers post-synthesis.

The plurality of particles may be homogeneous for one or more parameters or characteristics. A plurality that is homogeneous for a given parameter, in some instances, means that particles within the plurality deviate from each other no more than about +/−10%, preferably no more than about +/−5%, and most preferably no more than about +/−1% of a given quantitative measure of the parameter. As an example, the particles may be homogeneously porous. This means that the degree of porosity within the particles of the plurality differs by not more than +/−10% of the average porosity. In other instances, a plurality that is homogeneous means that all the particles in the plurality were treated or processed in the same manner, including for example exposure to the same agent regardless of whether every particle ultimately has all the same properties. In still other embodiments, a plurality that is homogeneous means that at least 80%, preferably at least 90%, and more preferably at least 95% of particles are identical for a given parameter.

The plurality of particles may be heterogeneous for one or more parameters or characteristics. A plurality that is heterogeneous for a given parameter, in some instances, means that particles within the plurality deviate from the average by more than about +/−10%, including more than about +/−20%. Heterogeneous particles may differ with respect to a number of parameters including their size or diameter, their shape, their composition, their surface charge, their degradation profile, whether and what type of agent is comprised by the particle, the location of such agent (e.g., on the surface or internally), the number of agents comprised by the particle, etc. The invention contemplates separate synthesis of various types of particles which are then combined in any one of a number of pre-determined ratios prior to contact with the sample. As an example, in one embodiment, the particles may be homogeneous with respect to shape (e.g., at least 95% are spherical in shape) but may be heterogeneous with respect to size, degradation profile and/or agent comprised therein. Particle size, shape and release kinetics can also be controlled by adjusting the particle formation conditions. For example, particle formation conditions can be optimized to produce smaller or larger particles, or the overall incubation time or incubation temperature can be increased, resulting in particles which have prolonged release kinetics.

The particles may also be coated with one or more stabilizing substances, which may be particularly useful for long term depoting with parenteral administration or for oral delivery by allowing passage of the particles through the stomach or gut without dissolution. For example, particles intended for oral delivery may be stabilized with a coating of a substance such as mucin, a secretion containing mucopolysaccharides produced by the goblet cells of the intestine, the submaxillary glands, and other mucous glandular cells.

To enhance delivery the particles may be incorporated, for instance, into liposomes, virosomes, cationic lipids or other lipid based structures. The term "cationic lipid" refers to lipids which carry a net positive charge at physiological pH. Such lipids include, but are not limited to, DODAC, DOTMA, DDAB, DOTAP, DC-Chol and DMRIE. Additionally, a number of commercial preparations of cationic lipids are available. These include, for example, LIPOFECTIN® (commercially available cationic liposomes comprising DOTMA and DOPE, from GIBCO/BRL, Grand Island, N.Y., USA); LIPOFECTAMINE® (commercially available cationic liposomes comprising DOSPA and DOPE, from GIBCO/BRL); and TRANSFECTAM® (commercially available cationic lipids comprising DOGS in ethanol from Promega™ Corp., Madison, Wis., USA). A variety of methods are available for preparing liposomes e.g., U.S. Pat. Nos. 4,186,183, 4,217,344, 4,235,871, 4,261,975, 4,485,054, 4,501,728, 4,774,085, 4,837,028, 4,946,787; and PCT Publication No. WO 91/17424. The particles may also be composed in whole or in part of GRAS components. i.e., ingredients are those that are Generally Regarded As Safe (GRAS) by the US FDA. GRAS components useful as particle material include non-degradeable food based particles such as cellulose.

The carrier domain can serve several functions. As discussed above, it may be useful for targeting the product to a specific region, such as a tissue. In that instance it could include a targeting agent such as a glycoprotein, an antibody, or a binding protein.

Further, the size of the carrier domain may be adjusted based on the particular use of the biomarker nanoparticle. For instance, the carrier domain may be designed to have a size greater than 5 nm. Particles, for instance, of greater than 5 nm are not capable of entering the urine, but rather, are cleared through the reticuloendothelial system (RES; liver, spleen, and lymph nodes). By being excluded from the removal through the kidneys any uncleaved biomarker nanoparticle will not be detected in the urine during the analysis step. Additionally, larger particles can be useful for maintaining the particle in the blood or in a tumor site where large particles are more easily shuttled through the vasculature. In some embodiments the carrier domain is 500 microns-5 nm, 250 microns-5 nm, 100 microns-5 nm, 10 microns-5 nm, 1 micron-5 nm, 100 nm-5 nm, 100 nm-10 nm, 50 nm-10 nm or any integer size range therebetween. In other instances the carrier domain is smaller than 5 nm in size. In such instance the biomarker nanoparticle will be cleared into the urine. However, the presence of free detectable marker can still be detected for instance using mass spectrometry. In some embodiments the carrier domain is 1-5 nm, 2-5 nm, 3-5 nm, or 4-5 nm.

Optionally the carrier domain may include a biological agent. In one embodiment a biological agent could be incorporated in the carrier domain or it may make up the carrier domain. For instance, it may form the scaffold or platform that the proteolytic domain is attached to. Thus the compositions of the invention can achieve two purposes at the same time, the diagnostic methods and delivery of a therapeutic agent. In some embodiments the biological agent may be a enzyme inhibitor. In that instance the biological agent can inhibit proteolytic activity at a local site and the detectable marker can be used to test the activity of that particular therapeutic at the site of action. HIV is an example of the disease in which active proteases can be monitored. In this embodiment the composition may include a microparticle or other delivery device carrying a protease inhibitor. The protease susceptible site may be sensitive to the HIV proteases such that feedback can be provided regarding the activity of the particular protease inhibitor.

Biological agents include diagnostic, cosmetic, and therapeutic agents, such as releasable drugs. Thus, any biological agent can be incorporated within the particles, which can locally or systemically deliver or maintain the incorporated agents following administration or application to a subject. Any biocompatible or pharmacologically acceptable material can be incorporated into the particles or trapped in the pores of the particles using technology known to those skilled in the art. Biological agents include but are not limited to synthetic inorganic and organic compounds, proteins and peptides, polysaccharides and other sugars, lipids, and DNA and RNA nucleic acid sequences having therapeutic, prophylactic, cosmetic or diagnostic activities. Nucleic acid sequences include genes, plasmids, vectors, antisense molecules that bind to complementary DNA to inhibit transcription, siRNA, shRNA, and ribozymes.

In certain instances, the biological agent is an anti-microbial agent. An anti-microbial agent, as used herein, refers to a naturally-occurring or synthetic compound which is capable of killing or inhibiting infectious microorganisms. The type of anti-microbial agent useful according to the invention will depend upon the type of microorganism with which the subject is infected or at risk of becoming infected. Anti-microbial agents include but are not limited to anti-bacterial agents, anti-viral agents, anti-fungal agents and anti-parasitic agents. Phrases such as "anti-infective agent", "anti-bacterial agent", "anti-viral agent", "anti-fungal agent", "anti-parasitic agent" and "parasiticide" have well-established meanings to those of ordinary skill in the art and are defined in standard medical texts.

Growth factors may also be incorporated into the carrier. As used herein, the term growth factor refers to any agent that stimulates cellular proliferation and/or differentiation. Growth factors include but are not limited to fibroblast growth factor (FGF), platelet-derived growth factor (PDGF), insulin-like growth factors (IGF) I and II, TGF-$\beta$, TGF-$\alpha$, bone morphogenetic protein (BMP) (e.g., BMP-2, BMP-3, BMP-4, BMP-6, or BMP-7), hedgehog proteins, growth differentiation factors, hematopoietic colony-stimulating factors (CSF), vascular endothelium growth factor (VEGF), osteoid-inducing factor (OIF), angiogenins, endothelins, hepatocyte growth factor, keratinocyte growth factor, ADMP-1, interleukins (IL) (e.g., IL-3 and IL-6), epithelial growth factors, dexamethasone, leptin, sortilin, transglutaminase, prostaglandin E, 1,25-dihydroxyvitamin D3, ascorbic acid, pro-collagen, glycerol phosphate, TAK- 778, statins, growth hormone, steel factor (SF), activin A (ACT), retinoic acid (RA), epidermal growth factor (EGF), hematopoietic growth factors, peptide growth factors, erythropoietin, tumor necrosis factors (TNF), interferons (IFN), heparin binding growth factor (HBGF), nerve growth factor (NGF) and muscle morphogenic factor (MMP).

The biological agent may also be an anti-cancer therapy. Anti-cancer therapies include for instance, radiotherapy, chemotherapy, adjuvant therapy, or any combination of the aforementioned.

The carrier domain may also be configured such that it can be detected in the body during the analysis. For instance, iron oxide can be incorporated into the particles so that the biomarker nanoparticle can be tracked using MRI to provide non-invasive imaging data.

The carrier is linked to the enzyme susceptible detectable marker. An enzyme susceptible detectable marker, as used herein, is the portion of the modular structure that promotes the enzymatic reaction in the subject, causing the release of a detectable marker. The enzyme susceptible detectable marker is an enzyme susceptible domain linked to a detectable marker.

The enzyme susceptible site is dependent on enzymes that are active in a specific disease state. For instance, tumors are associated with a specific set of enzymes. If the disease state being analyzed is a tumor then the product is designed with an enzyme susceptible site that matches that of the enzyme expressed by the tumor or other diseased tissue. Alternatively, the enzyme specific site may be associated with enzymes that are ordinarily present but are absent in a particular disease state. In this example, a disease state would be associated with a lack or signal associated with the enzyme, or reduced levels of signal compared to a normal reference.

An enzyme, as used herein refers to any of numerous proteins produced in living cells that accelerate or catalyze the metabolic processes of an organism. Enzymes act on substrates. The substrate binds to the enzyme at a location called the active site just before the reaction catalyzed by the enzyme takes place. Enzymes include but are not limited to proteases, glycosidases, lipases, heparinases, phosphatases.

The enzyme susceptible site may be optimized to provide both high catalytic activity (or other enzymatic activity) for specified target enzymes but to also release optimized detectable markers for detection. Patient outcome depends on the phenotype of individual diseases at the molecular level, and this is often reflected in expression of enzymes. The recent explosion of bioinformatics has facilitated exploration of complex patterns of gene expression in human tissues (Fodor, S. A. Massively parallel genomics. Science 277, 393-395 (1997)). Sophisticated computer algorithms have been recently developed capable of molecular diagnosis of tumors using the immense data sets generated by expression profiling (Khan J, Wei J S, Ringner M, Saal L H, Ladanyi M, Westermann F, et al. Classification and diagnostic prediction of cancers using gene expression profiling and artificial neural networks. Nat Med 2001; 7:673-679.). This information can be accessed in order to identify enzymes and substrates associated with specific diseases. Based on this information the skilled artisan can identify appropriate enzyme or substrates to incorporate into the biomarker nanoparticle. Table 1 provides a non-limiting list of enzymes associated with (either increased or decreased with respect to normal) disease and in some instances, the specific substrate. Table 2 provides a non-limiting list of substrates associated with disease or other conditions. Numerous other enzyme/substrate combinations associated with specific diseases or conditions are known to the skilled artisan and are useful according to the invention.

TABLE 1

| DISEASE | ENZYME | SUBSTRATE |
| --- | --- | --- |
| Cancer | MMP | collagens, gelatin, various ECM proteins |
| Cancer | MMP-2 | type IV collagen and gelatin |
| Cancer | MMP-9 | type IV and V collagens and gelatin |
| Cancer | kallikreins | kininogens, plasminogen |
| Cancer | cathepsins | broad spectrum of substrates |
| Cancer | plasminogen activator, tPA | Plasminogen |
| Cancer | ADAM (A Diseintegrin And Metalloprotease, also MDC, Adamalysin) | various extracellular domains of transmembrane proteins |
| Pancreatic carcinoma | MMP-7 | various, e.g. collagen 18, FasL, HLE, DCN, IGFBP-3, MAG, plasminogen, other MMPs |
| Pancreatic Cancer | ADAM9, ADAM15 | various extracellular domains of transmembrane proteins |
| Prostate adenocarcinoma | Matriptase, a type II transmembrane serine protease | unspecific, cleaves after Lys or Arg residues |
| Prostate cancer | Kallikrein 3 | kininogens, plasminogen |
| Prostate cancer | ADAM15 | various extracellular domains of transmembrane proteins |
| Ovarian carcinoma | Kallikrein 6 | kininogens, plasminogen |
| Epithelial-derived tumors (breast, prostate, ovarian, colon, oral) | Matriptase, a type II transmembrane serine protease | unspecific, cleaves after Lys or Arg residues |
| Ovarian Cancer | MMP-2, MMP-9, kallikrein-10 (hk-10) | type IV and V collagens and gelatin, kininogens, plasminogen |
| Breast, gastric, prostate cancer | cathepsins B, L and D | broad spectrum of substrates |
| Endometrial cancer | cathepsin B | unspecific cleavage of a broad spectrum of substrates without clear sequence specificity |
| esophageal adenocarcinoma | cathepsin B | unspecific cleavage of a broad spectrum of substrates without clear sequence specificity |

TABLE 1-continued

| DISEASE | ENZYME | SUBSTRATE |
|---|---|---|
| Invasive cancers, metastases | type II integral serine proteases (dipeptidyl peptidase IV (DPP4/CD26), seprase/fibroblast activation protein alpha (FAPalpha) and related type II transmembrane prolyl serine peptidases)) | |
| Invasive cancers, metastases viral infections | Seprase | various ECM proteins |
| All Retroviruses | viral protease | precursor GagPol fusion |
| HIV | HIV protease (HIV PR, an aspartic protease) | precursor Gag and GagPol proteins |
| Hepatitis C | NS3 serine protease | viral precursor polyprotein |
| Dengue | Dengue protease | auocleavage (NS2B/NS3), NS3/NS4A and NS4B/NS5 cleavage |
| West Nile | NS2B/NS3pro | viral precursor polyprotein |
| bacterial infections | | |
| *Legionella* spp. | zinc metalloprotease | Me-Arg-Pro-Tyr |
| Meninogencephalitis | histolytic cysteine protease | |
| *Streptococcus pyogenes* (Group A *Streptococcus*) | streptococcal pyrogenic exotoxin B (SpeB) | extracellular matrix, immunoglobulins, complement components |
| *Chlostridium difficile* | Cwp84 | fibronectin, laminin, vitronectin and other ECM proteins |
| Alzheimer's disease | BACE-1,2 (Alzheimer secretase) | β-amyloid precursor protein |
| Stroke and recovery | MMP, tPA | |
| cardiovascular disease | Angiotensin Converting Enzyme (ACE) | angiotensin I, bradykinin |
| Atherosclerosis | cathepsin K, L, S | broad spectrum of substrates |
| arthritis | MMP-1 | triple-helical fibrillar collagens |
| rheumatoid arthritis | thrombin | Osteopontin |
| osteoarthritis | thrombin | Osteopontin |
| osteoporosis/ostearthritis | cathepsin K, S | broad spectrum of substrates |
| Arthritis, inflammatory joint disease | Aggrecanase (ADAMTS4, ADAMTS11) | aggrecans (proteoglycans) |
| thrombosis | factor Xa (thrombokinase) | Prothrombin |
| thrombosis | ADAMTS13 | von Willebrand factor (vWF) |
| thrombosis | plasminogen activator, tPA | Plasminogen |
| Stress-induced Renal pressure natriuresis | Prostasin | epithelial Na channel subunits |

TABLE 2

| DISEASE | TARGET SUBSTRATE | ENZYME |
|---|---|---|
| Inflammation | Interleukin 1 beta | MMP-2, MMP-3, MMP-9, Trypsin, chymotrypsin, pepsin, Lys-C, Glu-C, Asp-N, Arg-C |
| Pituitary gland dysfunction, abnormal bone density, growth disorders | IGFBP-3 | MMP-1, MMP-3, MMP-9, Trypsin, chymotrypsin, pepsin, Lys-C, Glu-C, Asp-N, Arg-C |
| Cancer | TGF-beta | MMP-9, Trypsin, chymotrypsin, pepsin, Lys-C, Glu-C, Asp-N, Arg-C |
| Cancer, autoimmune disease | TNF | MMP-7, Trypsin, chymotrypsin, pepsin, Lys-C, Glu-C, Asp-N, Arg-C |
| Cancer, autoimmune disease | FASL | MMP-7, Trypsin, chymotrypsin, pepsin, Lys-C, Glu-C, Asp-N, Arg-C |
| Wound healing, cardiac disease | HB-EGF | MMP-3, Trypsin, chymotrypsin, pepsin, Lys-C, Glu-C, Asp-N, Arg-C |
| Pfeiffer syndrome | FGFR1 | MMP-2, Trypsin, chymotrypsin, pepsin, Lys-C, Glu-C, Asp-N, Arg-C |
| Cancer | Decorin | MMP-2, MMP-3, MMP-7, Trypsin, chymotrypsin, pepsin, Lys-C, Glu-C, Asp-N, Arg-C |

TABLE 2-continued

| DISEASE | TARGET SUBSTRATE | ENZYME |
|---|---|---|
| Cancer | Tumor associated carbohydrate antigens | Endoglycosidases |
| Cancer | Sialyl Lewis$^a$ | O-glycanase |
| Cancer | Sialyl Lewis$^x$ | O-glycanase |
| Cancer/Rheumatoid Arthritis, pulmonary hypertension | VEGF | Trypsin, chymotrypsin, pepsin, Lys-C, Glu-C, Asp-N, Arg-C |
| Cancer | EGF | Trypsin, chymotrypsin, pepsin, Lys-C, Glu-C, Asp-N, Arg-C |
| Cancer | IL2 | Trypsin, chymotrypsin, pepsin, Lys-C, Glu-C, Asp-N, Arg-C |
| Cancer inflammation/angiogenesis | IL6 | Trypsin, chymotrypsin, pepsin, Lys-C, Glu-C, Asp-N, Arg-C |
| Cancer | IFN-γ | Trypsin, chymotrypsin, pepsin, Lys-C, Glu-C, Asp-N, Arg-C |
| Cancer inflammation/angiogenesis, Rheumatoid Arthritis | TNF-α | Trypsin, chymotrypsin, pepsin, Lys-C, Glu-C, Asp-N, Arg-C |
| Cancer, Pulmonary fibrosis, Asthma | TGF-β | Trypsin, chymotrypsin, pepsin, Lys-C, Glu-C, Asp-N, Arg-C |
| Cancer, Pulmonary hypertension | PDGF | Trypsin, chymotrypsin, pepsin, Lys-C, Glu-C, Asp-N, Arg-C |
| Cancer, pulmonary cystadenoma | Fibroblast growth factor (FGF) | Trypsin, chymotrypsin, pepsin, Lys-C, Glu-C, Asp-N, Arg-C |
| Cancer | Brain-derived neurotrophic factor (BDNF) | Trypsin, chymotrypsin, pepsin, Lys-C, Glu-C, Asp-N, Arg-C |
| Cancer | Interferon regulatory factors (IRF-1, IRF-2) | Trypsin, chymotrypsin, pepsin, Lys-C, Glu-C, Asp-N, Arg-C |
| Inhibitor of tumor suppressors | MIF | Trypsin, chymotrypsin, pepsin, Lys-C, Glu-C, Asp-N, Arg-C |
| Lymphomas/carcinomas, alveolar proteinosis | GM-CSF | Trypsin, chymotrypsin, pepsin, Lys-C, Glu-C, Asp-N, Arg-C |
| Cancer invasion | M-CSF | Trypsin, chymotrypsin, pepsin, Lys-C, Glu-C, Asp-N, Arg-C |
| Chemical carcinogenesis, multiple schlerosis, rheumatoid arthritis, Crohn's disease | IL-12 | Trypsin, chymotrypsin, pepsin, Lys-C, Glu-C, Asp-N, Arg-C |
| Natural Killer T cell leukemias, inflammatory bowel disease, rheumatoid arthritis | IL-15 | Trypsin, chymotrypsin, pepsin, Lys-C, Glu-C, Asp-N, Arg-C |
| Cirrhosis | Tissue inhibitor of MMPs (TIMPs) | Trypsin, chymotrypsin, pepsin, Lys-C, Glu-C, Asp-N, Arg-C |
| Cirrhosis | Collagen I, III | MMP-1, MMP-8, Trypsin, chymotrypsin, pepsin, Lys-C, Glu-C, Asp-N, Arg-C |
| Cirrhosis | Collagen IV, V | MMP-2, Trypsin, chymotrypsin, pepsin, Lys-C, Glu-C, Asp-N, Arg-C |

Several of the enzyme/substrates described above are described in the following publications, all of which are incorporated herein in their entirety by reference: Parks, W. C. and R. P. Mecham (Eds): Matrix metalloproteinases. San Diego: Academic Press; 1998; Nagase, H. and J. F. Woessner, Jr. (1999) J. Biol. Chem. 274:21491; Ito, A. et al. (1996) J. Biol. Chem. 271:14657; Schonbeck, U. et al. (1998) J. Immunol. 161: 3340; Rajah, R. et al. (1999) Am. J. Cell Mol. Biol. 20:199; Fowlkes, J. L. et al. (1994) Endocrinology 135:2810; Manes, S. et al. (1999) J. Biol. Chem. 274:6935; Mira, E. et al. (1999) Endocrinology 140:1657; Yu, Q. and I. Stamenkovic (2000) Genes Dev. 14:163; Haro, H. et al. (2000) J. Clin. Invest. 105:143; Powell, C. P. et al. (1999) Curr. Biol. 9:1441; Suzuki, M. et al. (1997) J. Biol. Chem. 272:31730; Levi, E. et al. (1996) Proc. Natl. Acad. Sci. USA 93:7069; Imai, K. et al. (1997) Biochem. J. 322:809; Smith, M. M. et al. (1995) J. Biol. Chem. 270:6440; and Dranoff, G. (2004) Nat. Rev. Cancer 4: 11-22.

The enzyme susceptible detectable marker may be attached directly to the carrier. For instance it may be coated directly on the surface of microparticles using known techniques. Alternatively if the carrier is a protein material it may be directly connected through a peptide bond. Additionally, the enzyme susceptible detectable marker may be connected to the carrier domain through the use of a linker. As used herein "linked" or "linkage" means two entities are bound to one another by any physicochemical means. Any linkage known to those of ordinary skill in the art, covalent or non-covalent, is embraced. Thus, in some embodiments the carrier has a linker attached to an external surface, which can be used to link the enzyme susceptible detectable marker. Another molecule can also be attached to the linker.

The enzyme susceptible detectable marker is preferably a polymer made up of a plurality of chemical units. A "chemical unit" as used herein is a building block or monomer which may be linked directly or indirectly to other building blocks or monomers to form a polymer. In some embodiments the enzyme susceptible detectable marker is a peptide that is susceptible to cleavage by an enzyme or causes cleavage of a substrate associated with a disease or condition. A number of examples of when the proteolytic cleavage site is a peptide are presented in the table above.

The enzyme susceptible domain may also be a polysaccharide. Some polysaccharide specific degrading enzymes are associated with tumors, angiogenesis and other conditions. A "polysaccharide" is a biopolymer comprised of linked saccharide or sugar units. The polysaccharides used as proteolytic susceptible domains may be isolated or synthesized de novo. For example, the polysaccharides may be isolated from natural sources e.g. purified, as by cleavage and gel separation or may be synthesized e.g., by chemical synthesis and incorporated into the biomarker nanoparticle.

For instance, HSGAG degrading enzymes are enzymes that can be analyzed according to the methods of the invention. HSGAG degrading enzymes include heparinase-I, heparinase-II, heparinase-III, D-glucuronidase and L-iduronidase. The heparinases cleave at the glycosidic linkage before a uronic acid. Heparinase I clips at a glycosidic linkage before a 2-O sulfated iduronic acid. Heparinase-III cleaves at a glycosidic linkage before an unsulfated glucuronic acid. Heparinase-II cleaves at both Hep-I and Hep-III cleavable sites. Glucuronidase and iduronidase, as their name suggests cleave at the glycosidic linkage after a glucuronic acid and iduronic acid respectively. Nitrous acid clips randomly at glycosidic linkages after a N-sulfated hexosamine and converts the six membered hexosamine ring to a membered anhydromannitol ring. Appropriate enzyme susceptible domains may be designed based on the known substrates and cleavage sites of these enzymes.

The biomarker nanoparticle may also include an implantable microdelivery device that houses the modular structure. An implantable microdelivery device is any type of device, that is sized for implantation into a body and can retain the modular structure. For instance the device may be an implantable capsule that contains the modular structure housed there in. The capsule may have a semi-permeable membrane, such that the modular structure cannot pass though the membrane, but which is permeable to endogenous molecules such as enzymes and substrates as well as detectable markers. Alternatively the implantable microdelivery device may be a chip having the modular structure attached thereto. Examples of implantable microdelivery devices include but are not limited to implantable capsules, chips, sustained-release formulations, multi-pulse drug delivery resorbable polymeric microchip device (Grayson et al. Nature Materials, VOL 2, November 2003, p. 767), and controlled release microchips (Santini et al Nature, vol 397, 1999, p. 335). These devices may be made from many materials include many of the polymeric materials described herein. Preferably the implantable devices are biocompatible and non-toxic.

Modification of the enzyme susceptible domain by an enzyme in vivo, results in the production of a detectable marker. Alternatively, when the enzyme susceptible detectable marker is an enzyme the enzyme cleaves an endogenous substrate producing a detectable marker from the endogenous substrate. The detectable marker is a detectable molecule. It can be part of the enzyme susceptible domain, e.g. the piece that is released or added upon cleavage or it can be a separate entity. Preferably the detectable marker is composed of two ligands joined by a linker, as described above. The detectable marker may be comprised of, for instance one or more of a peptide, nucleic acid, small molecule, fluorophore/quencher, carbohydrate, particle, radiolabel, MRI-active compound, inorganic material, organic material, with encoded characteristics to facilitate optimal detection.

The detectable marker may be detected by any known detection methods to achieve the capture/detection step. A variety of methods may be used, depending on the nature of the detectable marker. Detectable markers may be directly detected, following capture, through optical density, radioactive emissions, nonradiative energy transfers, or detectable markers may be indirectly detected with antibody conjugates, affinity columns, strepavidin-biotin conjugates, PCR analysis, DNA microarray, and fluorescence analysis.

The capture assay in some embodiments involves a detection step selected from the group consisting of an ELISA, including fluorescent, colorimetric, bioluminescent and chemiluminescent ELISAs, a paper test strip or LFA, bead-based fluorescent assay, and label-free detection, such as surface plasmon resonance (SPR). The capture assay may involve, for instance, binding of the capture ligand to an affinity agent.

The analysis step may be performed directly on the biological sample or the signature component may be purified to some degree first. For instance, a purification step may involve isolating the detectable marker from other components in the biological sample. Purification steps include methods such as affinity chromatography. As used herein an "isolated molecule" or "purified molecule" is a detectable marker that is isolated to some extent from its natural environment. The isolated or purified molecule need not be 100% pure or even substantially pure prior to analysis.

The methods for analysing detectable markers by identifying the presence of a detectable marker may be used to provide a qualitative assessment of the molecule (e.g., whether the detectable marker is present or absent) or a quantitative assessment (e.g., the amount of detectable marker present to indicate a comparative activity level of the enzymes. The quantitative value may be calculated by any means, such as, by determining the percent relative amount of each fraction present in the sample. Methods for making these types of calculations are known in the art.

When the detectable marker is a nucleic acid, it can also be analyzed using PCR and microarrays. PCR methods are well-known in the art. For instance, U.S. Pat. No. 5,333,675, issued to Mullis et al. describes an apparatus and method for performing automated PCR. In general, performance of a PCR method results in amplification of a selected region of DNA by providing two DNA primers, each of which is complementary to a portion of one strand within the selected region of DNA. The primer is hybridized to a template strand of nucleic acid in the presence of deoxyribonucleotide triphosphates (dATP, dCTP, dGTP, and dTTP) and a chain extender enzyme, such as DNA polymerase. The primers are hybridized with the separated strands, forming DNA molecules that are single stranded except for the region hybridized with the primer, where they are double stranded. The double stranded regions are extended by the action of the chain extender enzyme (e.g. DNA polymerase) to form an extended double stranded molecule between the original two primers. The double stranded DNA molecules are separated to produce single strands which can then be re-hybridized with the primers. The process is repeated for a number of cycles to generate a series of DNA strands having the same nucleotide sequence between and including the primers.

Chain extender enzymes are well known in the art and include, for example, E. coli DNA polymerase I, klenow fragment of E. coli DNA polymerase I, T4 DNA polymerase, T7 DNA polymerase, recombinant modified T7 DNA polymerase, reverse transcriptase, and other enzymes. Heat stable enzymes are particularly preferred as they are useful in automated thermal cycle equipment. Heat stable polymerases include, for example, DNA polymerases isolated from *Bacillus stearothermophilus* (BIO-RAD®), *thermus thermophilous* (finzyme, ATCC number 27634), *thermus species* (ATCC number 31674), *Thermus aquaticus* strain TV11518 (ATCC number 25105), *Sulfolobus acidocaldarius*, described by Bukhrashuili et al., *Biochem. Biophys. Acta.*, 1008:102-07 (1909), *thermus filiformus* (ATCC number 43280), Taq DNA polymerase, commercially available from Perkin-Elmer-Cetus (Norwalk, Conn.), PROMEGA® (Madison, Wis.) and Stratagene (La Jolla, Calif.), and AmpliTaq™ DNA polymerase, a recombinant *thermus equitus* Taq DNA polymerase, available from Perkin-Elmer-Cetus and described in U.S. Pat. No. 4,889,818.

Preferably, the PCR-based methods performed according to the invention are automated and performed using thermal cyclers. Many types of thermal cyclers are well-known in the art. For instance, M.J. Research (Watertown, Mass.) provides a thermal cycler having a peltier heat pump to provide precise uniform temperature control in the thermal cyclers; DeltaCycler thermal cyclers from Ericomp (San Diego, Calif.) also are peltier-based and include automatic ramping control, time/temperature extension programming and a choice of tube or microplate configurations. The RoboCycler™ by Stratagene (La Jolla, Calif.) incorporates robotics to produce rapid temperature transitions during cycling and well-to-well uniformity between samples; and a particularly preferred cycler, is the Perkin-Elmer Applied Biosystems (Foster City, Calif.) ABI Prism™ 877 Integrated Thermal cycler, which is operated through a programmable interface that automates liquid handling and thermocycling processes for fluorescent DNA sequencing and PCR reactions.

The presence or absence of enzymes in the subject may also be determined using hybridization techniques. Standard hybridization techniques of microarray technology are utilized to assess the presence of nucleic acids in the biological sample. Microarray technology, which is also known by other names including: DNA chip technology, gene chip technology, and solid-phase nucleic acid array technology, is well known to those of ordinary skill in the art and is based on, but not limited to, obtaining an array of identified nucleic acid probes on a fixed substrate, labeling target molecules with reporter molecules (e.g., radioactive, chemiluminescent, or fluorescent tags such as fluorescein, Cye3-dUTP, or Cye5-dUTP), hybridizing target nucleic acids to the probes, and evaluating target-probe hybridization. A probe with a nucleic acid sequence that perfectly matches the target sequence will, in general, result in detection of a stronger reporter-molecule signal than will probes with less perfect matches. Many components and techniques utilized in nucleic acid microarray technology are presented in *The Chipping Forecast*, Nature Genetics, Vol. 21, January 1999, the entire contents of which is incorporated by reference herein.

According to the present invention, microarray substrates may include but are not limited to glass, silica, aluminosilicates, borosilicates, metal oxides such as alumina and nickel oxide, various clays, nitrocellulose, or nylon. In all embodiments a glass substrate is preferred. An "array" as used herein is a set of molecules arranged in a specific order with respect to a surface. Preferably the array is composed of polynucleotides attached to the surface. Oligonucleotide arrays can be used to screen nucleic acid samples for a target nucleic acid, which can be labeled with a detectable marker. A fluorescent signal resulting from hybridization between a target nucleic acid and a substrate-bound oligonucleotide provides information relating to the identity of the target nucleic acid by reference to the location of the oligonucleotide in the array on the substrate. Such a hybridization assay can generate thousands of signals which exhibit different signal strengths. These signals correspond to particular oligonucleotides of the array. Different signal strengths will arise based on the amount of labeled target nucleic acid hybridized with an oligonucleotide of the array.

Conditions for optimal hybridization are known. The hybridization conditions in general are those used commonly in the art, such as those described in Sambrook et al., "Molecular Cloning: A Laboratory Manual", (1989), 2nd Ed., Cold Spring Harbor, N.Y.; Berger and Kimmel, "Guide to Molecular Cloning Techniques", *Methods in Enzymology*, (1987), Volume 152, Academic Press, Inc., San Diego, Calif.; and Young and Davis, (1983), *PNAS* (USA) 80:1194. In general, incubation temperatures for hybridization of nucleic acids range from about 20° C. to 75° C. For probes 17 nucleotides residues and longer, a preferred temperature range for hybridization is from about 50° C. to 54° C. The hybridization temperature for longer probes is preferably from about 55° C. to 65° C. and for shorter probes is less than 52° C. Rehybridization may be performed in a variety of time frames. Preferably, hybridization of SNP and RCGs performed for at least 30 minutes.

The detectable marker may be labeled. For example, a label may be added directly to a nucleic acid when the isolated detectable marker is subjected to PCR. For instance, a PCR reaction performed using labeled primers or labeled nucleotides will produce a labeled product. Labeled nucleotides (e.g., fluorescein-labeled CTP) are commercially available. Methods for attaching labels to nucleic acids are well known to those of ordinary skill in the art and, in addition to the PCR method, include, for example, nick translation and end-labeling.

Labels suitable for use in the methods of the present invention include any type of label detectable by standard means, including spectroscopic, photochemical, biochemical, electrical, optical, or chemical methods. Preferred types of labels include fluorescent labels such as fluorescein. A fluorescent label is a compound comprising at least one fluorophore. Commercially available fluorescent labels include, for example, fluorescein phosphoramidides such as fluoreprime (Pharmacia, Piscataway, N.J.), fluoredite (Millipore, Bedford, Mass.), FAM (ABI, Foster City, Calif.), rhodamine, polymethadine dye derivative, phosphores, TEXAS RED® (sulforhodamine 101 acid chloride), green fluorescent protein, CY3, and CY5. Polynucleotides can be labeled with one or more spectrally distinct fluorescent labels. "Spectrally distinct" fluorescent labels are labels which can be distinguished from one another based on one or more of their characteristic absorption spectra, emission spectra, fluorescent lifetimes, or the like. Spectrally distinct fluorescent labels have the advantage that they may be used in combination ("multiplexed"). Radionuclides such as $^3$H, $^{125}$I, $^{35}$S, $^{14}$C, or $^{32}$P are also useful labels according to the methods of the invention. A plurality of radioactively distinguishable radionuclides can be used. Such radionuclides can be distinguished, for example, based on the type of radiation (e.g. α, β, or δ radiation) emitted by the radionuclides. The $^{32}$P signal can be detected using a phosphoimager, which currently has a resolution of approximately 50 microns. Other known techniques, such as chemiluminescence or colormetric (enzymatic color reaction), can also be used.

Quencher compositions in which a "donor" fluorophore is joined to an "acceptor" chromophore by a short bridge that is the binding site for the enzyme may also be used. The signal of the donor fluorophore is quenched by the acceptor chromophore through a process believed to involve resonance energy transfer (RET). Cleavage of the peptide results in separation of the chromophore and fluorophore, removal of the quench, and generation of a subsequent signal measured from the donor fluorophore.

Once the data is obtained, e.g. as a two-dimensional image, a computer can be used to transform the data into a displayed image which varies in color depending on the intensity of light emission at a particular location. Any type of commercial software which can perform this type of data analysis can be used. In general, the data analysis involves the steps of determining the intensity of the fluorescence emitted as a function of the position on the substrate, removing the outliers, and calculating the relative binding affinity. One or more of the presence, absence, and intensity of signal corresponding to a label is used to assess the presence or absence of an detectable marker. The presence and absence of one or more detectable markers can be used to determine the disease status of an individual based on the presence or absence of an enzyme.

The data may also be observed and analyzed manually. For instance, the presence or absence of a fluorescent label may be observed in order to provide the diagnostic or prognostic information from the data.

The disease or condition assessed according to the methods of the invention is any disease or condition that is associated with an enzyme. For instance, cancer, cardiovascular disease, arthritis, viral, bacterial, parasitic or fungal infection, Alzheimer's disease emphysema, thrombosis, hemophilia, stroke, organ disfunction, any inflammatory condition, vascular disease, parenchymal disease, or a pharmacologically-induced state are all known to be associated with enzymes. A pharmacologically induced state is a condition in which enzyme inhibitors and other agents directly or indirectly affect enzyme activities. Thus each of the these can be assessed or monitored or studied according to methods of the invention.

It is useful to be able to differentiate non-metastatic primary tumors from metastatic tumors, because metastasis is a major cause of treatment failure in cancer patients. If metastasis can be detected early, it can be treated aggressively in order to slow the progression of the disease. Metastasis is a complex process involving detachment of cells from a primary tumor, movement of the cells through the circulation, and eventual colonization of tumor cells at local or distant tissue sites. Additionally, it is desirable to be able to detect a predisposition for development of a particular cancer such that monitoring and early treatment may be initiated. For instance, an extensive cytogenetic analysis of hematologic malignancies such as lymphomas and leukemias have been described, see e.g., Solomon et al., Science 254, 1153-1160, 1991. Early detection or monitoring using the non-invasive methods of the invention may be useful.

Solid tumors progress from tumorigenesis through a metastatic stage and into a stage at which several different active proteases can be involved. Some protease are believed to alter the tumor such that it can progress to the next stage, i.e., by conferring proliferative advantages, the ability to develop drug resistance or enhanced angiogenesis, proteolysis, or metastatic capacity.

Alzheimer's disease causes progressive dementia with consequent formation of amyloid plaques, neurofibrillary tangles, gliosis and neuronal loss. The disease occurs in both genetic and sporadic forms whose clinical course and pathological features are quite similar. Three genes have been discovered to date which, when mutated, cause an autosomal dominant form of Alzheimer's disease. These encode the amyloid protein precursor (APP) and two related proteins, presenilin-1 (PS1) and presenilin-2 (PS2). Mutations in any of the three proteins have been observed to enhance proteolytic processing of APP via an intracellular pathway that produces amyloid beta peptide (Aβ peptide), a 40-42 amino acid long peptide that is the primary component of amyloid plaque in Alzheimer's disease. Pathological processing of APP at the β- and γ-secretase sites, which are located N-terminal and C-terminal to the α-secretase site, respectively, produces a very different result than processing at the α site. Sequential processing at the β- and γ-secretase sites releases the Aβ peptide, a peptide possibly very important in Alzheimer's disease pathogenesis. The β secretase enzyme, termed Aspartyl Protease 2 (Asp2) is thought to mediate this processing. The presence of Asp2 activity is important for the diagnosis and prognosis of Alzheimer's disease. This enzyme and it's substrate can also be used in the methods of the invention to monitor the ability of a therapeutic to function in slowing the progression of Alzheimer's disease.

The methods may also be useful for detecting the presence of clots in a subject by analyzing thrombin activity. Whereas MRI or ultrasound can accurately resolve the relative burden and anatomical location of clots, they currently cannot discriminate biologically active clots from stable ones. For example, patients who present with DVT are prescribed anticoagulants if there is evidence that their clots are extending—a diagnosis that requires continuous monitoring of their clot burden over the course of weeks—which could potentially be predicted by elevated thrombin activity at an earlier stage when thrombi are most responsive to fibrinolytic therapies.[27] Related studies in imaging atherosclerotic plaques showed that measuring thrombin activity can be sufficiently predictive to stage and differentiate severe from stable plaques that could not be discriminated based on anatomical features alone. [9c]

As used herein, a subject is a human, non-human primate, cow, horse, pig, sheep, goat, dog, cat, or rodent. In all embodiments human subjects are preferred. In aspects of the invention pertaining to cancer diagnosis in general the subject preferably is a human suspected of having cancer, or a human having been previously diagnosed as having cancer. Methods for identifying subjects suspected of having cancer may include physical examination, subject's family medical history, subject's medical history, biopsy, or a number of imaging technologies such as ultrasonography, computed tomography, magnetic resonance imaging, magnetic resonance spectroscopy, or positron emission tomography.

As used herein, a biological sample is a tissue sample. The biological sample may be examined in the body, for instance, by detecting a label at the site of the tissue, i.e. urine. Alternatively the biological sample may be collected from the subject and examined in vitro. Biological samples include but are not limited to urine, blood, saliva, or mucous secretion. In preferred embodiments the tissue sample is obtained non-invasively, such as the urine.

A "plurality" of elements, as used throughout the application refers to 2 or more of the elements.

The biomarker nanoparticles of the invention are administered to the subject in an effective amount for detecting enzyme activity. An "effective amount", for instance, is an amount necessary or sufficient to cause release of a detectable level of detectable marker in the presence of an enzyme. The effective amount of a compound of the invention described herein may vary depending upon the specific compound used, the mode of delivery of the compound, and whether it is used alone or in combination. The effective amount for any particular application can also vary depending on such factors as the disease being assessed or treated, the particular compound being administered, the size of the subject, or the severity of the disease or condition as well as the detection method. One of ordinary skill in the art can empirically determine the effective amount of a particular molecule of the invention without necessitating undue experimentation. Combined with the teachings provided herein, by choosing among the various active compounds and weighing factors such as potency, relative bioavailability, patient body weight, severity of adverse side-effects and preferred mode of administration, an effective regimen can be planned.

Pharmaceutical compositions of the present invention comprise an effective amount of one or more agents, dissolved or dispersed in a pharmaceutically acceptable carrier. The phrases "pharmaceutical or pharmacologically acceptable" refers to molecular entities and compositions that do not produce an adverse, allergic or other untoward reaction when administered to an animal, such as, for example, a human, as appropriate. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences (1990), incorporated herein by reference). Except insofar as any conventional carrier is incompatible with the active ingredient, its use in the therapeutic or pharmaceutical compositions is contemplated. The agent may comprise different types of carriers depending on whether it is to be administered in solid, liquid or aerosol form, and whether it need to be sterile for such routes of administration as injection.

Preferably the material is injected into the body but could also be administered by other routes. For instance, the compounds of the present invention can be administered intravenously, intradermally, intraarterially, intralesionally, intratumorally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences (1990), incorporated herein by reference).

In certain embodiments, pharmaceutical compositions may comprise, for example, at least about 0.1% of an active compound. In other embodiments, the an active compound may comprise between about 2% to about 75% of the weight of the unit, or between about 25% to about 60%, for example, and any range derivable therein.

The agent may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups also can be derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

According to the methods of the invention, the compound may be administered in a pharmaceutical composition. In general, a pharmaceutical composition comprises the compound of the invention and a pharmaceutically-acceptable carrier. Pharmaceutically-acceptable carriers for peptides, monoclonal antibodies, and antibody fragments are well-known to those of ordinary skill in the art. As used herein, a pharmaceutically-acceptable carrier means a non-toxic material that does not interfere with the effectiveness of the biological activity of the active ingredients.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The compounds of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

The compounds of the invention may be administered directly to a tissue. Direct tissue administration may be achieved by direct injection. The compounds may be administered once, or alternatively they may be administered in a plurality of administrations. If administered multiple times, the compounds may be administered via different routes. For example, the first (or the first few) administrations may be made directly into the affected tissue while later administrations may be systemic.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. Techniques for preparing aerosol delivery systems are well known to those of skill in the art. Generally, such systems should utilize components which will not significantly impair the biological properties of the active agent (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing aerosols without resort to undue experimentation.

The compounds, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

The data generated according to the invention may optionally be converted into a bar code or other human- or machine-readable form. For example, each line of a bar code may indicate the presence or absence of a specific enzyme or groups of specific enzymes for a particular subject. The bar code data can be compared with a database of information on other subjects or information on the disease to aid in the diagnosis, prognosis or other analysis of the test subject.

In one embodiment of the invention, the data generated herein is used to select clinical treatment paradigms for cancers. Treatment options, as described herein, may include but are not limited to: radiotherapy, chemotherapy, adjuvant therapy, or any combination of the aforementioned methods. Aspects of treatment that may vary include, but are not limited to: dosages, timing of administration, or duration or therapy; and may or may not be combined with other treatments, which may also vary in dosage, timing, or duration. Another treatment for cancer is surgery, which can be utilized either alone or in combination with any of the aforementioned treatment methods. One of ordinary skill in the medical arts may determine an appropriate treatment paradigm based on evaluation of data generated by the methods described herein.

In certain embodiments, software for calculating and processing the data as described herein can be provided on a computer connected by data link to a data generating device, such as a mass spectrometer, microarray reader or PCR machine. Any standard data link can be used, including serial or parallel cables, radio frequency or infrared telemetry links, LAN connections, WAN connections, etc. Alternatively, data can be transferred by computer-readable medium (e.g., magnetic or optical medium) and read by the software. The data also can be entered directly by the user via user interface, such as a keyboard, monitor, mouse, graphical user interface such as touch screen, etc. The computer may be contained within the data generating device, providing an integrated system for generating raw data, calculating ratios, and displaying such ratios. One or more computers also may be linked to one or more data generating devices and one or more display devices, such as in a local area network or wide area network.

In one embodiment of the invention, a visual display is used to display the data for the classification, diagnosis, prediction of prognosis and/or therapeutic monitoring. The visual display can be a graphical user interface, such as a monitor, or a printer.

The data can be processed individually or by a computer. For instance, a computer-implemented method for generating a data structure, tangibly embodied in a computer-readable medium, representing a quantitative value of a set of detectable markers may be performed according to the invention. The quantitative values may be compared with a reference database. Alternatively a qualitative pattern may be compared with a reference database.

A computer system that may implement the above as a computer program typically may include a main unit connected to both an output device which displays information to a user and an input device which receives input from a user. The main unit generally includes a processor connected to a memory system via an interconnection mechanism. The input device and output device also may be connected to the processor and memory system via the interconnection mechanism.

One or more output devices may be connected to the computer system. Example output devices include a cathode ray tube (CRT) display, liquid crystal displays (LCD), printers, communication devices such as a modem, and audio output. One or more input devices also may be connected to the computer system. Example input devices include a keyboard, keypad, track ball, mouse, pen and tablet, communication device, and data input devices such as sensors. The subject matter disclosed herein is not limited to the particular input or output devices used in combination with the computer system or to those described herein.

The computer system may be a general purpose computer system which is programmable using a computer programming language, such as C++, Java, or other language, such as a scripting language or assembly language. The computer system also may include specially-programmed, special purpose hardware such as, for example, an Application-Specific Integrated Circuit (ASIC). In a general purpose computer system, the processor typically is a commercially-available processor, of which the series x86, CELERON®, and Pentium processors, available from Intel, and similar devices from AMD and Cyrix, the 680X0 series microprocessors available from Motorola, the PowerPC microprocessor from IBM and the Alpha-series processors from Digital Equipment Corporation, are examples. Many other processors are available. Such a microprocessor executes a program called an operating system, of which Windows NT, LINUX®, UNIX®, DOS, VMS® and OS8 are examples, which controls the execution of other computer programs and provides scheduling, debugging, input/output control, accounting, compilation, storage assignment, data management and memory management, and communication control and related services. The processor and operating system define a computer platform for which application programs in high-level programming languages may be written.

A memory system typically includes a computer readable and writeable nonvolatile recording medium, of which a magnetic disk, a flash memory and tape are examples. The disk may be removable, such as a "floppy disk," or permanent, known as a hard drive. A disk has a number of tracks in which signals are stored, typically in binary form, i.e., a form interpreted as a sequence of one and zeros. Such signals may define an application program to be executed by the microprocessor, or information stored on the disk to be processed by the application program. Typically, in operation, the processor causes data to be read from the nonvolatile recording medium into an integrated circuit memory element, which is typically a volatile, random access memory such as a dynamic random access memory (DRAM) or static memory (SRAM). The integrated circuit memory element typically allows for faster access to the information by the processor than does the disk. The processor generally manipulates the data within the integrated circuit memory and then copies the data to the disk after processing is completed. A variety of mechanisms are known for managing data movement between the disk and the integrated circuit memory element, and the subject matter disclosed herein is not limited to such mechanisms. Further, the subject matter disclosed herein is not limited to a particular memory system.

The subject matter disclosed herein is not limited to a particular computer platform, particular processor, or particular high-level programming language. Additionally, the computer system may be a multiprocessor computer system or may include multiple computers connected over a computer network. It should be understood that each module may be separate modules of a computer program, or may be separate computer programs. Such modules may be operable on separate computers. Data may be stored in a memory system or transmitted between computer systems. The subject matter disclosed herein is not limited to any particular implementation using software or hardware or firmware, or any combination thereof. The various elements of the system, either individually or in combination, may be implemented as a computer program product tangibly embodied in a machine-readable storage device for execution by a computer processor. Various steps of the process may be performed by a computer processor executing a program tangibly embodied on a computer-readable medium to perform functions by operating on input and generating output. Computer programming languages suitable for implementing such a system include procedural programming languages, object-oriented programming languages, and combinations of the two.

The invention further provides efficient methods of identifying pharmacological agents or lead compounds for agents active in vivo. Generally, the screening methods involve assaying for compounds that beneficially alter enzyme activity in vivo. Such methods according to the invention are adaptable to automated, high-throughput screening of compounds.

The methods may be used in any subject. For instance animal models of disease may be used to screen multiple putative therapeutic agents in order to assess the activity level of the putative therapeutic agents on particular enzymes associated with disease. For instance, a library of biomarker nanoparticles having different putative therapeutic agents associated with the carrier can be administered to the animal model. If each therapeutic agent is associated with a unique detectable marker, then the activity of the putative therapeutic agent could be assessed by analyzing the level of detectable marker in the urine as described herein.

Additionally, the methods may be used for the advancement of personalized medicine. For instance, a set of biomarker nanoparticles having multiple therapeutic agents, each therapeutic agent associated with a discreet detectable marker could be administered to a subject having a disease to assess which therapeutic agent is most effective in that individual subject. Based on the data, an appropriate therapeutic strategy could be designed. An example of this may be seen in HIV. Protease inhibitors are used therapeutically to inhibit the activity of critical proteases associated with HIV survival and activity. A set of biomarker nanoparticles could be generated having different enzyme inhibitors as the carrier or part of the carrier. Each enzyme inhibitor is associated with a particular detectable marker, such that the activity of the particular inhibitor on the enzyme can be assessed by monitoring the level of signature in the urine. For instance a particularly active inhibitor would cause a reduced level of detectable marker being transported to the urine.

Typically, a known active therapeutic agent may serves as a negative control, i.e., the known therapeutic agent is incorporated into a biomarker nanoparticle. Putative therapeutic agents, also referred to herein as candidate agents encompass numerous chemical classes, although typically they are organic compounds. Preferably, the candidate pharmacological agents are small organic compounds, i.e., those having a molecular weight of more than 50 yet less than about 2500, preferably less than about 1000 and, more preferably, less than about 500. Candidate agents comprise functional chemical groups necessary for structural interactions with polypeptides and/or nucleic acids, and typically include at least an amine, carbonyl, hydroxyl, or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid, the agent typically is a DNA or RNA molecule, although modified nucleic acids as defined herein are also contemplated.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant, and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

The invention also includes kits having a container housing a biomarker nanoparticle, wherein the biomarker nanoparticle comprises a carrier domain linked to an enzyme susceptible detectable marker. The kit may also include a second container housing an analytical reagent.

The kits, also referred to as articles, include pharmaceutical or diagnostic grade compounds of the invention in one or more containers. The article may include instructions or labels promoting or describing the use of the compounds of the invention. For instance, the kit may include instructions for administering the biomarker nanoparticle to a subject and for analyzing the detectable marker of the biomarker nanoparticle in a biological sample of the subject.

As used herein, "promoted" includes all methods of doing business including methods of education, hospital and other clinical instruction, pharmaceutical industry activity including pharmaceutical sales, and any advertising or other promotional activity including written, oral and electronic communication of any form, associated with compositions of the invention.

"Instructions" can define a component of promotion, and typically involve written instructions on or associated with packaging of compositions of the invention. Instructions also can include any oral or electronic instructions provided in any manner.

Thus the agents described herein may, in some embodiments, be assembled into pharmaceutical or diagnostic or research kits to facilitate their use in therapeutic, diagnostic or research applications. A kit may include one or more containers housing the components of the invention and instructions for use. Specifically, such kits may include one or more agents described herein, along with instructions describing the intended therapeutic application and the proper administration of these agents. In certain embodiments agents in a kit may be in a pharmaceutical formulation and dosage suitable for a particular application and for a method of administration of the agents.

The kit may be designed to facilitate use of the methods described herein by physicians and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water or a cell culture medium), which may or may not be provided with the kit. As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for human administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container.

The kit may have a variety of forms, such as a blister pouch, a shrink wrapped pouch, a vacuum sealable pouch, a sealable thermoformed tray, or a similar pouch or tray form, with the accessories loosely packed within the pouch, one or more tubes, containers, a box or a bag. The kit may be sterilized after the accessories are added, thereby allowing the individual accessories in the container to be otherwise unwrapped. The kits can be sterilized using any appropriate sterilization techniques, such as radiation sterilization, heat sterilization, or other sterilization methods known in the art. The kit may also include other components, depending on the specific application, for example, containers, cell media, salts, buffers, reagents, syringes, needles, a fabric, such as gauze, for applying or removing a disinfecting agent, disposable gloves, a support for the agents prior to administration etc.

The compositions of the kit may be provided as any suitable form, for example, as liquid solutions or as dried powders. When the composition provided is a dry powder, the powder may be reconstituted by the addition of a suitable solvent, which may also be provided. In embodiments where liquid forms of the composition are sued, the liquid form may be concentrated or ready to use. The solvent will depend on the compound and the mode of use or administration. Suitable solvents for drug compositions are well known and are available in the literature. The solvent will depend on the compound and the mode of use or administration.

The kits, in one set of embodiments, may comprise a carrier means being compartmentalized to receive in close confinement one or more container means such as vials, tubes, and the like, each of the container means comprising one of the separate elements to be used in the method. For example, one of the containers may comprise a positive control for an assay. Additionally, the kit may include containers for other components, for example, buffers useful in the assay.

The present invention also encompasses a finished packaged and labeled pharmaceutical product. This article of manufacture includes the appropriate unit dosage form in an appropriate vessel or container such as a glass vial or other container that is hermetically sealed. In the case of dosage forms suitable for parenteral administration the active ingredient is sterile and suitable for administration as a particulate free solution. In other words, the invention encompasses both parenteral solutions and lyophilized powders, each being sterile, and the latter being suitable for reconstitution prior to injection. Alternatively, the unit dosage form may be a solid suitable for oral, transdermal, topical or mucosal delivery.

In a preferred embodiment, the unit dosage form is suitable for intravenous, intramuscular or subcutaneous delivery. Thus, the invention encompasses solutions, preferably sterile, suitable for each delivery route.

In another preferred embodiment, compositions of the invention are stored in containers with biocompatible detergents, including but not limited to, lecithin, taurocholic acid, and cholesterol; or with other proteins, including but not limited to, gamma globulins and serum albumins.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures.

More specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material. The invention further provides an article of manufacture comprising a needle or syringe, preferably packaged in sterile form, for injection of the formulation, and/or a packaged alcohol pad.

EXAMPLES

Example 1: Methods

Syntheses of Biomarker Nanoparticle:

Iron oxide nanoworms (NWs) were synthesized according to previously published protocols.[12] Thrombin-sensitive substrate-reporter peptides (biotin-eGvndneeGffsar(K-Flsc)GGfPRSGGGC, SEQ ID NO: 2, lower case=D-isomer) were synthesized by the Tufts University Core Facility peptide synthesis service. Amine-terminated NWs were first reacted with succinimidyl iodoacetate (Pierce) to introduce sulfhydryl-reactive handles. Cysteine terminated peptides and 20 kDa polyethylene glycol-SH (Laysan Bio.) were then mixed with NWs (95:20:1 molar ratio) for one hour at room temperature (RT) and purified by fast protein liquid chromatography. Stock solutions were stored in PBS at 4° C. For pharmacokinetic studies, NWs were first reacted with VT750 (PerkinElmer) prior to PEGylation as above. For fluorogenic assays, peptides were synthesized with fluorescein in place of the ligand-encoded reporter. For monitoring protease activity in vivo, peptides were synthesized with VT750 in place of the N-terminal biotin.

Heterobifunctional ligand-encoded reporters R1-4 were synthesized by derivatizing Glutamate-Fibrinopeptide B with a capture ligand (fluorescein, dinitrophenyl, tetramethylrhodamine, or ALEXA FLUOR® 488) on the C-terminus and a detection ligand (biotin) on the opposing terminus. Nanoworms (NWs, ~60 nm) were synthesized from the reaction of Iron(III) chloride hexahydrate and Iron(II) chloride tetrahydrate with dextran (15-25 kDa) as previously described[28,29]. Aminated NWs were derivatized with N-succimidyl iodoacetate and reacted with sulfhydryl-terminated protease-sensitive reporters. Reporter valency was (~20-30) was quantified by absorbance or ELISA.

Heterobifunctional ligand-encoded reporters R1-4 were synthesized by derivatizing the N-terminus of Glutamate-Fibrinopeptide B-biotin (GluFib-biotin, sequence=eGvndneeGffsar-biotin, SEQ ID NO: 1, lower case=D-isomer, New England Peptide) with NHS-fluorescein (R1, Pierce), NHS-rhodamine (R3, Pierce), or NHS-ALEXA FLUOR® 488 (R4, Invitrogen), in a 1:10 peptide: dye ratio, or were synthesized (R2, New England Peptide). ALEXA FLUOR® 488-PEG-Biotin (R4, PEG) was synthesized by reaction of A488-maleimide (Invitrogen) with NHS-Biotin (Pierce) and $NH_2$—PEG-thiol (5 kDa, Laysan) in a 10:10:1 dye:biotin:PEG ratio and purified using illustra NAP-25 columns (GE Healthcare). The resultant conjugates were purified by HPLC (Gilson). Reporter concentration was quantified by absorbance according to dye-specific extinction coefficients in a 96-well plate by plate reader (Molecular Devices SpectraMax Plus).

Nanoworms (NWs) were formed by the reaction of Iron (III) chloride hexahydrate and Iron(II) chloride tetrahydrate (Sigma) with dextran ($M_r$ 15-25 kDa, Fluka) as previously described[28,29]. Mean hydrodynamic size by dynamic light scattering (DLS; Malvern Instruments Nano ZS90) was 60 nm.

Aminated NWs were reacted overnight with a 500-fold molar excess of N-succinimidyl iodoacetate (SIA, Pierce) overnight at 20° C. in 50 mM sodium borate, pH 8.3, 5 mM EDTA to facilitate linkage to sulfhydryl-terminated peptides. Following purification by fast-performing liquid chromatography (FPLC, GE Healthcare), SIA-derivatized NWs were reacted with substrate-conjugated reporters (MIT Swanson Biotechnology Center, Tufts University peptide synthesis core facility, New England Peptide) and mPEG-thiol (20 kDa; Laysan) in a 1:95:20 NW:peptide:PEG ratio overnight at 20° C. in the same borate buffer. Reporter-encoded substrate-functionalized NWs were again purified and exchanged into 1×PBS by FPLC and stored at 4° C. Substrate-reporter valency on NWs (typically 20-30) was quantified by absorbance or ELISA (described below).

In Vitro Protease Assays:

NWs (200 nM by peptide) were mixed with human thrombin (2 µM), FVIIa (10 nM), FIXa (90 nM), FXa (160 nM), FXIa (31 nM), and activated protein C (60 nM, Haematologic Technologies) in a 384-well plate at 37° C. in activity buffers according to the manufacturer's instructions and monitored with a microplate reader (SpectroMax Gemini EM). For plasma studies, NWs were mixed with 50 µL of control human plasma (Thermo Scientific™) and 50 µL of 80 mM $CaCl_2$ (Sigma) or PBS before monitoring fluorogenesis. For thrombin inhibition experiments, bivalirudin (Anaspec) was added to a final concentration of 5 mg/mL and pre-incubated for two minutes prior to addition of NWs. For ELISA analysis, NWs (100 nM by peptide) were incubated with thrombin for 10 min. at 37° C. and cleaved reporters ($R_1$) were purified from NWs by centrifugal size filtration.

Fluorescent reporter-bound thrombin- or MMP-sensitive NWs (substrates PLGLRSW, SEQ ID NO: 3, or PLGVRGK, SEQ ID NO: 4, respectively) were introduced to recombinant thrombin or MMP9 (respectively). Release of homoquenched fluorophores upon proteolysis was read as increased fluorescence by plate reader at 37° C. Inhibitors Argatroban or Marimastat were incubated with the protease-NW cocktail at 100 µM. To quantify reporter release by LFA, reporter-functionalized NWs were incubated with cognate proteases, passed through a 30 kDa MW cutoff filter, quantified by LFA, and analyzed by Mann-Whitney test.

Fluorescein-functionalized MMP- or thrombin-sensitive NWs (2.5 µM by peptide) were mixed in 1% w/v BSA (Sigma) with recombinant thrombin (15 nM; Haematologic Technologies) or MMP9 (15 nM; R&D Systems) in 100 µL final volume in a 384-well plate per manufacturer's instructions and fluorescent signal increase due to enzymatic release of homoquenched reporters was monitored at 37° C. (SpectroMax Gemini EM microplate reader). Argatroban (Sigma) or Marimastat (Tocris) were incubated with the NW-protease cocktail at 100 µM final concentration. To assay proteolytic reporter release by LFA, reporter-functionalized enzyme sensitive NWs were incubated with MMP9 or thrombin as above at 37° C. for four hours and passed through a 30 kDa MW cutoff centrifugal filter. The filtered reporters were diluted to within LFA dynamic range and assayed by LFA as described below. Reporter stability experiments were performed using reporter 3 (1 µM) mixed in 1% w/v BSA with recombinant thrombin or MMP9 (both 15 nM) as above to 100 µL final volume and were incubated at 37° C. for 1 h. Following this, the reporters were passed through a 30 kDa MW cutoff centrifugal filter as above and assayed by R3 ELISA.

ELISA Detection of Bifunctionalized Reporters:

96-well plates (Thermo Scientific) were incubated with either 0.8 µg/mL of anti-Flsc (GeneTex, GTX19224) or 0.4 µg/mL of anti-ALEXA FLUOR® 488 (Invitrogen™, A11094) diluted in PBS overnight at 4° C. Plates were blocked with 1% w/v bovine serum albumin (Sigma) in PBS for 1 hr before 100 µL of samples were added. Reporters captured on the plate were then detected by adding 100 µL of 0.2 µg/mL NeutrAvidin-HRP (Pierce), developed with 50 µL TMB solution (Thermo Scientific™) for 5-15 minutes and quenched with 50 µL of HCl before the absorbance of the wells was determined by microplate analysis (Spectra-Max Plus, Molecular Devices) at 450 nm. Plates were washed 3× with PBST between each steps and incubation occurred at RT unless otherwise stated.

Characterization of Thromboplastin-Induced Thrombosis:

Each vial of thromboplastin containing 3-4 mg (from rabbit brain, Sigma) was dissolved in 2 mL of PBS. To quantify fibrin deposition, bovine fibrinogen (Sigma) was reacted with 3-fold molar excess of VT750 for 1 hr at RT, and purified by centrifugal size filtration (size cutoff, Millipore). Swiss Webster mice (Taconic) were lightly anesthetized with isofluorane and administered mixtures of VT750-fibrinogen (1 nmol by VT750) with thromboplastin (n=3 mice per dose) via tail vein injections. After 30 minutes, mice were euthanized by $CO_2$ asphyxiation and organs were scanned on the LI-COR Odyssey Infrared Imaging System. Fibrin(ogen) fluorescence in each organ was quantified using ImageJ software (NIH). To test thrombin inhibition, mice were intravenously administered bivalirudin (10 mg/kg) five minutes prior to co-injection of thromboplastin. For histology, lungs were inflated with 4% paraformaldehyde while all other organs were incubated in 4% paraformaldehyde for 1-2 hours at RT. All organs were stored in 70% ethanol until paraffin-embedding, sectioning, and staining (Koch Institute Histology Core).

NW Pharmacokinetics.

To analyze NW and peptide pharmacokinetics, mice were given either VT750-labeled NWs or NWs conjugated with VT750-labeled peptides (600 nM by peptide) in conjuction with thromboplastin (dose) and excised organs were imaged on the IVIS imaging system (Xenogen). To analyze tissue sections by immunostaining, NWs (600 nM by peptide) and thromboplastin (2 µL/g b.w.) were administered to mice and major organs were harvested after 30 minutes. The lungs were inflated with 4% paraformaldehyde before freezing and sectioning in OCT. Representative sections were stained for NWs (anti-Flsc primary, Genetex GTX19224), fibrin (Nordic GAM/Fbg/Bio) and Hoechst (Invitrogen, H3569) before analysis by fluorescence microscopy (Nikon Eclipse Ti).

Effect of Hydration State on Urine Concentration.

The free reporter $R_2$ (biotin-eGvndneeGffsar(K-AF488), SEQ ID NO: 1) was synthesized by the Tufts University Core Facility peptide synthesis service. Mice (n=5 mice) were anesthetized and injected subcutaneously with a PBS bolus equivalent to 10% their body weights. After two hours, $R_2$ (125 nm) was administered to mice via a tail vein injection. Mice were placed over 96-well plates surrounded by cylindrical sleeves for 30 minutes post-NW injection to allow mice to void. Urine samples were stored at −80° C. until ELISA analysis.

Urinary Monitoring of Thrombosis.

Experiments were conducted in a paired setup. Thrombin-sensitive NWs (600 nM by peptide) and $R_2$ (125 nM) were co-injected into healthy mice (n=5-10 mice) to determine background levels protease activity (Day 0) and placed over 96-well plates to collect urine. Five days later, mice were again dosed with NWs, $R_2$ and thromboplastin before urine was collected from mice 30 minutes post-NW injection. For thrombin inhibition experiments, mice were intravenously administered bivalirudin (10 mg/kg) five minutes prior to NW/$R_2$ injections. Urine samples were stored at −80° C. until ELISA analysis.

Statistical Analyses.

ANOVA analyses and Student's t-test were calculated with GraphPad 5.0 (Prism). Pearson's r coefficient was calculated with Excel (Microsoft Office).

In Vivo Imaging.

All animal studies were approved by MIT's committee on animal care (protocol 0411-036-14). Thrombin- or MMP-sensitive NWs were functionalized with infrared fluorescent reporter VT-750. Bladder and/or lung localization of proteolytically released fluorescent reporter was imaged in control and diseased mice. Thrombosis was induced by coinjection of collagen and epinephrine with synthetic biomarkers in female Swiss Webster mice; colorectal flank tumors were induced by subcutaneous injection of human cell line LS 147T in female NCr nude mice.

Synthetic biomarkers for in vivo imaging were prepared by reacting free amine groups on MMP- or thrombin-sensitive NWs (both on substrate N-termini and on NWs) with VivoTag 750-NHS (Perkin Elmer) and purified by FPLC.

Human LS 174T colorectal cancer cells were grown in Dulbecco's Modified Eagle's Medium (ATCC) supplemented with 10% FBS (Gibco) and 1% Penicillin-Streptomycin (CELLGRO®). Female NCr Nude mice (4-6 wk; Taconic) were inoculated subcutaneously with $5 \times 10^6$ LS 174T cells/flank and allowed to grow to approximately 0.5 $cm^3$ total burden (volume=length*width*depth/2). Tumor-bearing and age-matched control mice were intravenously infused with 200 μL VivoTag- and FAM-labeled MMP-sensitive NWs (1.67 μM by substrate), allowing visualization by an in-vivo imaging system (IVIS, Xenogen) 5-60 m post-infusion. For histology, mice were sacrificed 1 h post-infusion. Tumors were removed, fixed in 4% paraformaldehyde, frozen in OCT (Tissue-Tek), sectioned, and stained with rat anti-CD31 (Santa Cruz), DAPI (Invitrogen™), and goat anti-FAM (GeneTex) prior to imaging by fluorescence microscopy (Nikon Eclipse Ti).

To model thrombosis, female Swiss Webster (4-6 wk; Taconic) mice were coinfused with 200 μL VivoTag- and FAM-labeled thrombin-sensitive NWs (0.84 μM by peptide), 10 μg/kg epinephrine (Sigma), and 280 μg/kg collagen (Chronolog). 15 minutes post-induction, mice were sacrificed and their lungs were inflated with PBS and excised. Infrared fluorescent imaging of lungs was taken using a LI-COR Odyssey infrared imager. Peptide substrates were PLGLRSW (SEQ ID NO: 3) for thrombin and PLGVRGK (SEQ ID NO: 4) for MMP[30].

ELISA Assay Characterization.

96-well plates were adsorbed with capture antibodies and blocked with 1% BSA in 1×PBS. Reporter standards were applied and detected by addition of neutravidin-horseradish peroxidase. Oxidation of chromogenic substrate TMB for 1-5 m allowed quantification of reporter concentration. All incubations were 1 h and plates were washed with 1×PBS with 0.5% w/v TWEEN® 20 (Polysorbate 20) between steps. Urine interference was assayed by spiking R1 in 1:100 control mouse urine. Assay specificity was measured by quantifying capture specificity of each antibody to all reporters and normalizing signal to a cognate reporter ladder.

Mouse anti-fluorescein (GeneTex), rabbit anti-DNP and rabbit anti-A488 (Invitrogen), and mouse anti-rhodamine (Rockland) antibodies were adsorbed to 96-well Bacti plates (Thermo) at concentrations 0.4-0.8 μg/mL for 1 h in 1×PBS. Plates were then blocked for 1 h with 1×PBS with 1% w/v BSA (Sigma). Reporter standards were applied to blocked plates in 2-fold serial dilutions in 100 μL volume for 1 h to characterize assay linearity. To detect reporters, 100 μL of 0.4 μg/mL NeutrAvidin™-HRP (Pierce) was applied for 1 h. Bound HRP was exposed with 50 μL Ultra-TMB (Pierce) for 1-5 m followed by quenching with 50 μL 1 N HCl. Between each step, plates were washed 3× with 1×PBS with 0.5% v/v TWEEN® 20 (Polysorbate 20) (Sigma). Absorbance at 450 nm was measured, plotted against known reporter concentration, and used to generate a linear fit over the assay's linear absorbance region. Assay limit of detection (LOD) was calculated as three standard deviations above mean background signal.

To test interference due to urine, urine from untreated mice was added to R1 standard at a 1:100 dilution. To quantify assay specificity, reporter concentrations at the peak of each reporter's linear region were applied to each of the four capture antibodies and the ELISA was completed as normal. Signal for each of the four capture antibody types was quantified by comparison to a standard ladder and normalized to the maximal signal from reporters captured by their cognate antibody.

Paper Lateral Flow Assay Characterization.

Capture (same as for ELISA) or control (α-streptavidin) antibodies were printed in 2 mm-spaced lines with 50 nL droplets at 0.5 mm pitch onto cellulose ester membrane. Membranes were laminated to a plastic backing with glass fiber conjugate and absorbent pads. The resultant construct was cut into 4 mm strips and stored at 4° C. Reporters diluted 1:1 in urine were applied to the conjugate pad and flushed with wash buffer (1×PBS with 1% w/v TWEEN® 80 (Polysorbate 80)). Reporters were detected using 40 nm streptavidin-gold nanoparticles. Dried strips were scanned and processed by a custom script that integrated and quantified band intensity.

Antibodies (same as above) were printed in lines spaced by 2 mm using 50 nL droplets at 0.5 mm pitch (Digilab MicroSys) onto HiFlow Plus cellulose ester membrane (240 s/4 cm flow rate, Millipore). Control lines were anti-streptavidin antibody (Abcam) at 0.5 mg/mL, while reporter capture antibodies were the same as for ELISA and were applied at 1 mg/ml (αR1, αR3, αR4) or 2 mg/mL (αR2). Cellulose membrane (Millipore) was laminated to a plastic backing. 10 mm glass fiber conjugate pad (Millipore) was laminated to the sample side of the cellulose membrane and 20 mm cellulose fiber pads were laminated to both the sample side of the conjugate pad and the run-off end of the cellulose membrane. The resultant construct was cut into 4 mm strips which were stored at 4° C.

Two-fold dilutions of marker standards in 1×PBS with 1% w/v BSA with 1:1 control urine spiked in were applied to the conjugate pad and washed with 200 μL of wash buffer (1×PBS with 1% w/v TWEEN® 80 (Polysorbate 80)) on the sample pad. To detect the markers, 5 μL of streptavidin-conjugated gold nanoparticles (40 nm; BBI International)

were applied to the conjugate pad and washed with an additional 200 µL of wash buffer. Test strips were allowed to dry and could be visualized by eye or applied to a scaling template and scanned (600 dpi; Epson V330 Photo) or imaged by cell phone (Samsung Galaxy Nexus). Resultant images were loaded into MATLAB® (MathWorks) and processed by a custom script that integrated signal over background across each antibody line. Marker orthogonality was characterized by comparing reporter capture by each antibody by applying a single reporter and quantifying signal over background noise across each antibody line. All strips were performed in at least triplicate.

Collection and Analysis of Urinary Peptides.

Urine was collected from mice intravenously infused with synthetic biomarker cocktails (free R4 plus either R3-functionalized thrombin-sensitive NWs to detect thrombosis or R2-functionalized MMP-sensitive NWs to detect CRC) for 30 or 60 m post-injection (to detect thrombosis or CRC, respectively). Urine collection times were optimized from previous studies using these disease models[30,31] and are dependent on site of disease and rate of enzymatic substrate cleavage. Reporter concentration in unprocessed urine was assayed by above protocols from urine diluted $1:10^2$-$10^4$ for ELISA or 1:4-5 for LFA. Data was analyzed using receiver-operator characteristic (ROC) curves (both) and Wilcoxon signed rank test (CRC) or Mann-Whitney test (thrombosis).

Mice were intravenously infused with 200 µL PBS with R4 (A488-PEG-Biotin, thrombosis model: 0.125 µM, CRC model: 1 µM) as an injection control and either R2-functionalized MMP-sensitive NWs (1.67 µM by peptide; tumor volume ~0.5 cm³) or R3-functionalized thrombin-sensitive NWs (0.84 µM by peptide; thrombosis model). Immediately following infusion, mice were placed over 96-well plates enclosed by a cylindrical tube to collect urine for 30 m (thrombosis model) or 1 h (tumor model). Urine collection times were optimized from previous studies using these disease models[30,31] and are dependent on site of disease and rate of enzymatic substrate cleavage. Urine was stored at −80° C. directly following collection.

Unprocessed urine was diluted (1:100-1:10,000) in 1×PBS with 1% w/v BSA and reporters were quantified by ELISA (at least 2 replicates) using standards as described above. Urine was applied to lateral flow test strips in 5 µL volume, at 1:4 (thrombosis model) or 1:5 (CRC model) dilution. Lateral flow tests were performed in triplicate as described above and test strips were allowed to dry and were quantified by automated script as described above. ELISA and LFA data was analyzed using a Wilcoxon signed rank test (CRC) and a Mann-Whitney test (thrombosis).

Injectable and Companion Diagnostics.

The exemplary synthetic biomarkers have been designed from widely used materials for a variety of commercial purposes. Many of these materials are widely used in drugs and medical products and are available easily and inexpensively (iron oxide, dextran, poly(ethylene glycol), fluorescein, biotin, and 25-mer peptides compatible with solid-phase synthesis). In the design of the synthetic biomarker platform, the standardized coupling strategies compatible with solid-phase synthesis (heterobifunctional crosslinker succinimidyl iodoacetate (SIA) to couple thiol-containing cysteine residues on the peptides to aminated dextran on the iron oxide nanoworms were used). Globalization and increased volume of synthesis due to commercially successful peptide drugs have resulted in a precipitous drop in peptide synthesis costs. Human dosages may be extrapolated from the mouse studies to be about ~0.16 mg/kg.

The exemplary synthetic biomarkers described herein are dosed at ~12 nmol/kg in mice (~1.5 µM in 200 µL in a 25 g mouse), as quantified by reporter valency (0.4 pmol/kg by iron oxide core). Each synthetic biomarker is approximated to have a peptide valency of 30 (3 kDa each) and a coating poly(ethylene glycol) (PEG) valency of 10 (20 kDa each) on each 115 kDa nanoworm. In the average 62 kg individual (Walpole et al. *BMC Public Health* 2012), this is a 10.0 mg total dose, of which 2.9 mg is nanoworms, 5.0 mg is PEG, and 2.2 mg is peptide.

Example 2: Biomarker Nanoparticles Specifically Sense the Proteolytic Activity of Thrombin within the Complex Milieu of Plasma Synthetic biomarkers designed to survey intravascular sites for acute thrombosis, the activation of a cascade of protease activity that orchestrates the formation of obstructive blood clots within vessels, were designed (FIG. 1A). Thrombi are a critical pathophysiological feature of numerous vascular diseases including acute coronary syndrome, stroke, and venous thromboembolism.[7] The most important serine protease in the coagulation cascade is thrombin, which not only catalyzes the conversion of fibrinogen to fibrin that serves as the structural scaffold of a clot, but also regulates haemostasis through positive and negative feedback circuits.[8] To date, a number of studies have described the use of near-infrared fluorogenic probes to detect thrombin activity in the setting of thrombus formation as well as other thrombin-dependent diseases such as atherosclerosis.[9] More recently, these probes have been modified to include cell penetrating mechanisms that are activated after cleavage to improve the retention of the imaging agent and maintenance of the detection signal.[9c,10] In the clinic, the blood biomarker D-dimer, a byproduct of fibrin degradation, is often used as an indicator of thrombosis; however, this test is highly susceptible to artifacts introduced by a blood draw, has poor specificity, and more accurately reflects plasmin (i.e. fibrinolysis) rather than thrombin activity.[11]

Nanoparticles that survey the host vasculature for thrombi have been developed. In response to thrombin activity, these nanoparticles of the invention release reporters into the urine as an integrated measure of the aggregate burden of systemic clots. Described herein is a method to encode these reporters with structurally-distinct ligands that allow antibody-based detection by enzyme-linked immunosorbent assay (ELISA) in standardized 96-well plates that makes this platform readily amenable for use in clinical laboratories.

Figure 13:
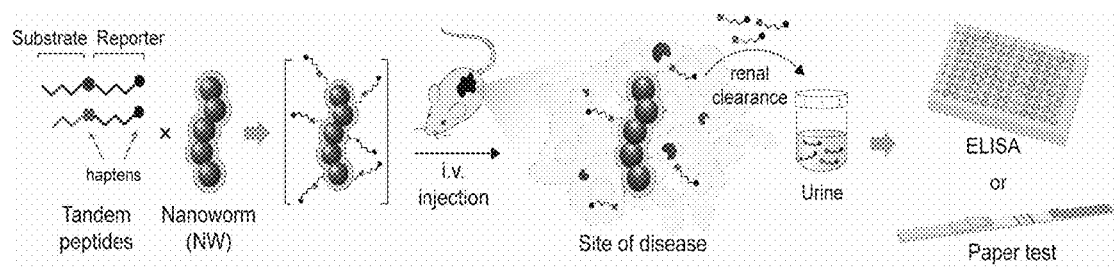
FIG. 13 shows the schematic of a biomarker nanoparticle and method of use of the invention. Hapten-encoded tandem peptides are conjugated to nanoworm (NW) nanoparticles. When administered intravenously, these agents accumulate at sites of disease and release reporters into the urine for detection by low-cost affinity assays such as ELISA or paper-based test strips.

The construction of synthetic biomarkers for thrombosis involves modifying the surface of iron oxide nanoworms (NW) with substrate-reporter tandem peptides that are cleavable by thrombin and detectable by ELISA (FIG. 1A).[6,12] A general schematic of the synthesis and use of the biomarker nanoparticles of the invention is shown in FIG. 13. To first develop a suitable substrate, the thrombin cleavable sequence fPR-x-S(x=site of cleavage, $k_{cat}/K_m$~9.33×10⁶)[13] was extended to include glycine spacers and a C-terminal cysteine to allow coupling to NWs via sulfyhydryl chemistry.[12] To test substrate specificity, fluorophore-labeled derivatives were conjugated onto NWs at a valency sufficient to produce homoquenched substrates (~40 peptides per NW) and then incubated the NWs with purified thrombin or a panel of blood clotting proteases (FXa, APC, FIXa, FVIIa, FXIa), each present at its maximal physiological concentration during thrombosis (FIG. 1B). Freely emitting peptide fragments that were released by thrombin activity increased sample fluorescence by more than 25-fold within ten minutes (red, FIG. 1C). By contrast, negligible proteolysis was observed from the panel of non-cognate proteases, as well as by thrombin in the presence of bivalirudin (Bival), a clinically-approved direct thrombin inhibitor.

To further investigate the ability to sense thrombin activity from blood, NWs were spiked into human plasma samples inactivated with sodium citrate (an anticoagulant that chelates the co-factor calcium) and monitored plasma fluorescence after the addition of excess calcium chloride ($CaCl_2$) to trigger coagulation or phosphate buffered saline (PBS) as a control. Plasma fluorescence markedly increased upon activation of the clotting cascade but not in control samples or in the presence of bivalirudin (FIG. 1D). Collectively, these results establish the ability of the NWs to specifically sense the proteolytic activity of thrombin within the complex milieu of plasma.

Figure 2:
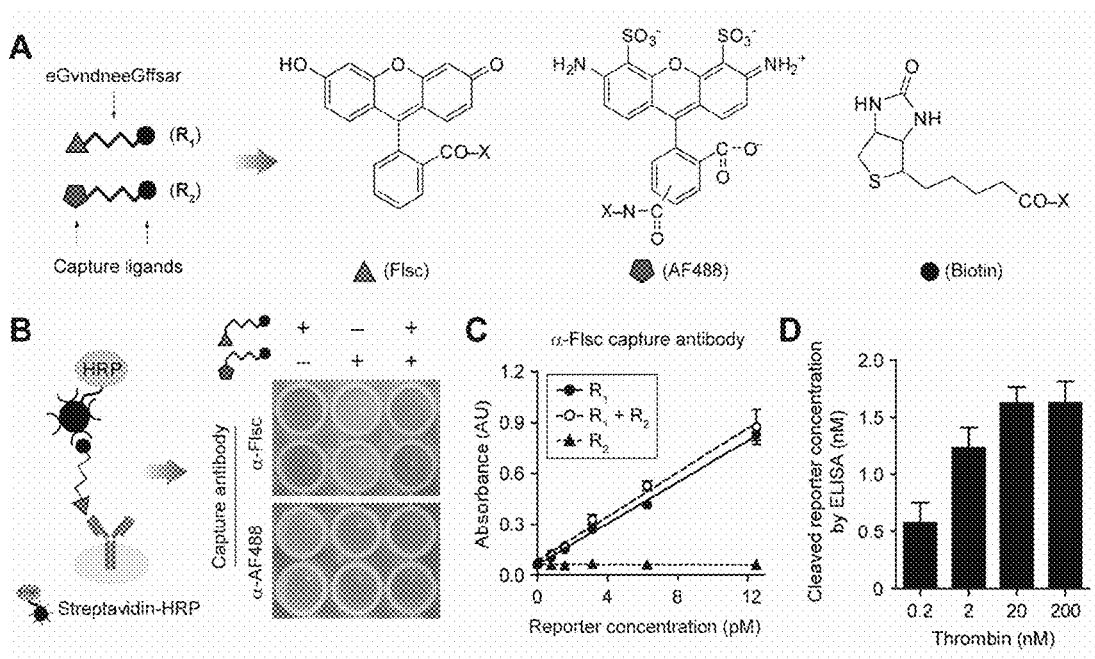
FIGS. 2A-D show the detection of ligand-encoded reporters by ELISA. (A) Design of ligand-encoded reporters $R_1$ and $R_2$ along with chemical structures of associated ligands. (B) Schematic of ELISA sandwich complex and photograph of developed 96-well plates showing specific detection of $R_1$ and $R_2$ spiked into control urine samples. (C) Absorbance values ($\lambda$=450 nm) of wells coated with anti-Flsc antibodies used to detect serial dilutions of $R_1$, $R_1$+$R_2$, and $R_2$ in urine (n=3 per condition, s.d.). (D) Quantification of the level of cleaved reporters ($R_1$) released from NWs after incubation with increasing concentrations of thrombin (n=3 per condition, s.d.).
Figure 5:
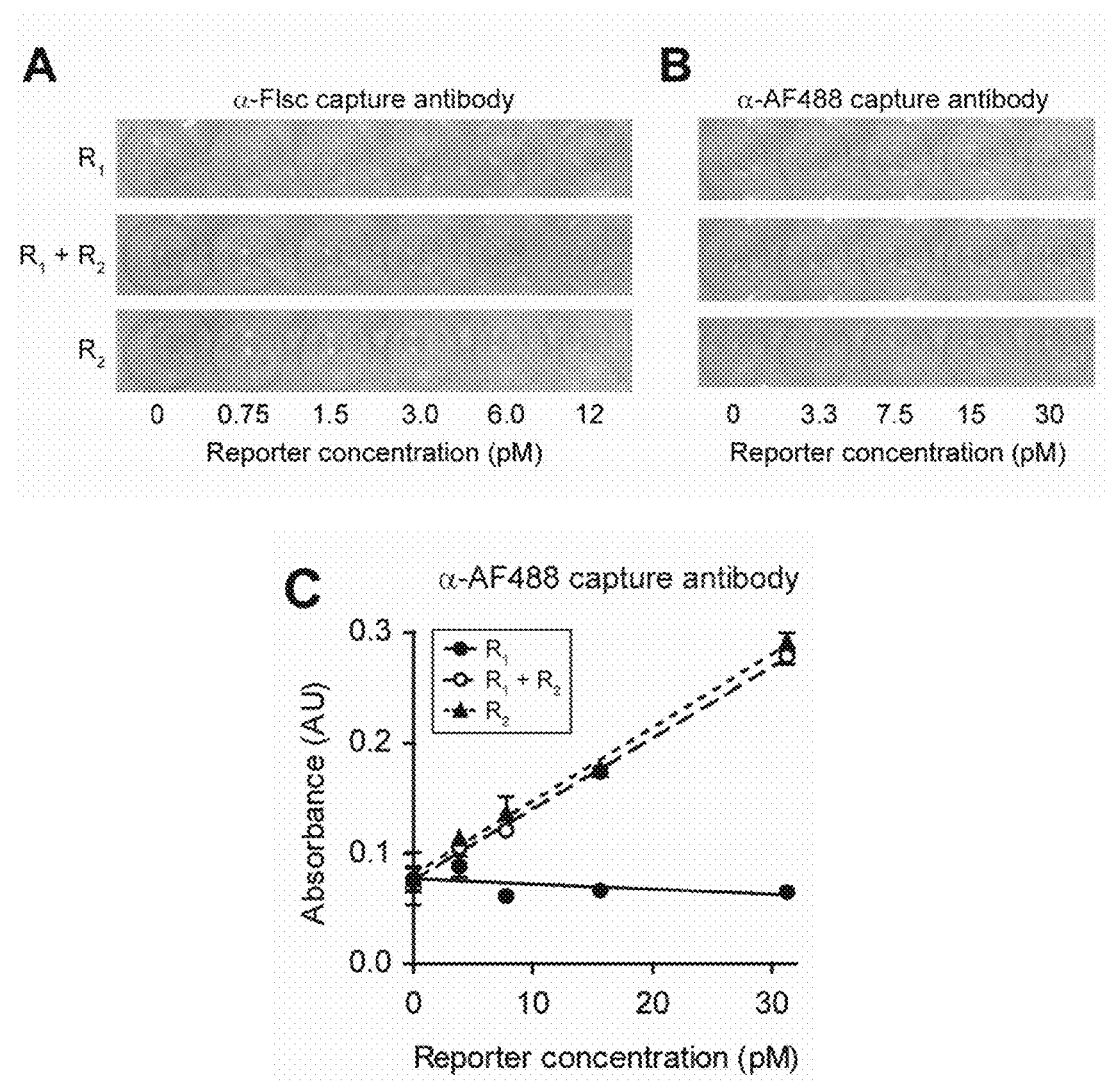
FIGS. 5A-C show photographs of the colorimetric detection of R1, R1+R2, and R2 spiked in urine using an (A) anti-Flsc or (B) anti-AF488 capture antibody. (C) Absorbance values of anti-AF488 ELISA plate from (B), measured at 450 nm (n=3 per condition, s.d.).
Figure 6:
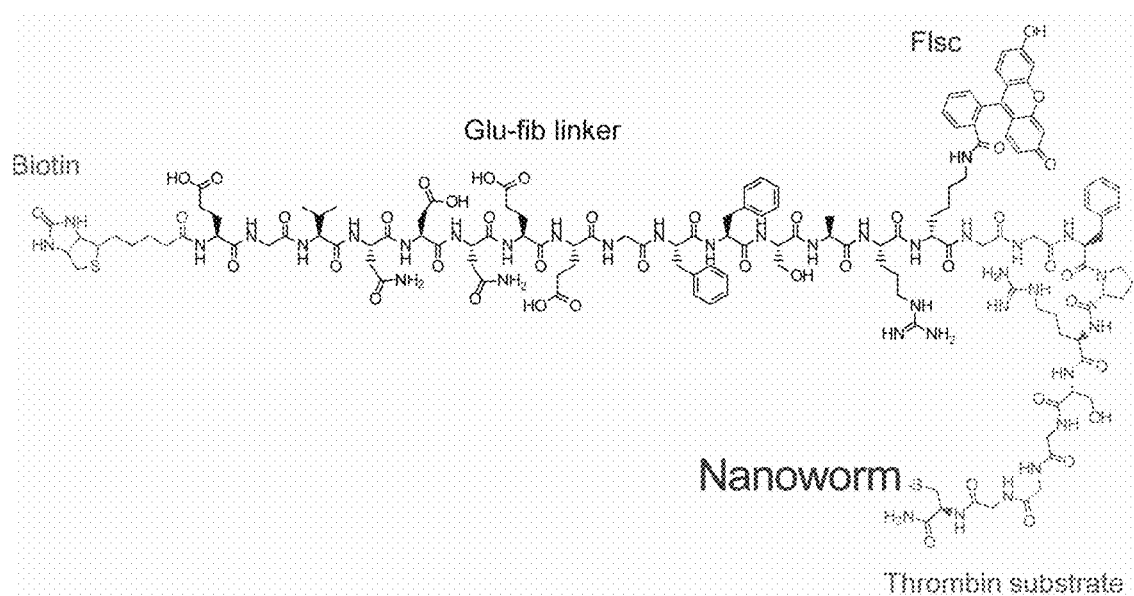
FIG. 6 shows the structure of biotin-eGvndneeGffsar(K-Flsc)GGfPRSGGGC (SEQ ID NO: 2) conjugated to NWs.

Example 3: Structures of the Invention are Capable of Monitoring Protease Activity We built a system of ligand-encoded reporters that would allow quantification of protease activity in a 96-well format by ELISA, the primary detection platform for many clinical tests. Conventional ELISAs detect a target analyte via a sandwich complex composed of two affinity agents that bind to distinct epitopes on the analyte (FIG. 2A). To build a synthetic reporter, the protease-resistant peptide Glutamate-Fibrinopeptide B (Glu-fib, sequence=eGvndneeGffsar (SEQ ID NO: 1), lower case=D-isomer)—which we selected for its high renal clearance efficiency[14]—was modified at the termini with structurally-distinct ligands (i.e. Flsc or AF488) and biotin (labeled $R_1$ and $R_2$ respectively; FIG. 2A). These reporters were then spiked into urine and applied to 96-well plates pre-coated with capture antibodies (α-Flsc or α-AF488) before the presence of $R_1$ or $R_2$ was detected by the addition of neutravidin-horseradish peroxidase (HRP) and its catalytic development of 3,3',5,5'-tetramethylbenzidine (TMB). As predicted from the specificities of the antibodies, a significant change in color appeared only in wells containing matched antibody-ligand pairs (+/− or −/+ wells, FIG. 2B) and was not affected by the presence of non-cognate reporters (+/+ wells). Identical trends were observed at the limits of detection for both capture antibodies (~3 pM, FIG. 2C, FIG. 5), indicating that the synthetic reporters were detected with high specificity and sensitivity comparable with protein-based ELISAs.[15] With an optimized thrombin substrate and a reporter system in place, NWs decorated with the final tandem peptide construct (sequence=biotin-eGvndneeGffsar(K-Flsc)GGfPRSGGGC, SEQ ID NO: 2, FIG. 6) were then incubated with increasing levels of thrombin and found that the amount of cleavage products released into solution (isolated by size filtration) was correspondingly dose dependent, establishing the ability to monitor thrombin activity by ELISA (FIG. 2D). Collectively these results indicate that the specificity of ligand-antibody interactions can be used to build panels of orthogonal reporters for monitoring protease activity by standardized 96-well assays.

Example 4: Biomarker Nanoparticles Detect Thrombosis In Vivo

Figure 3:
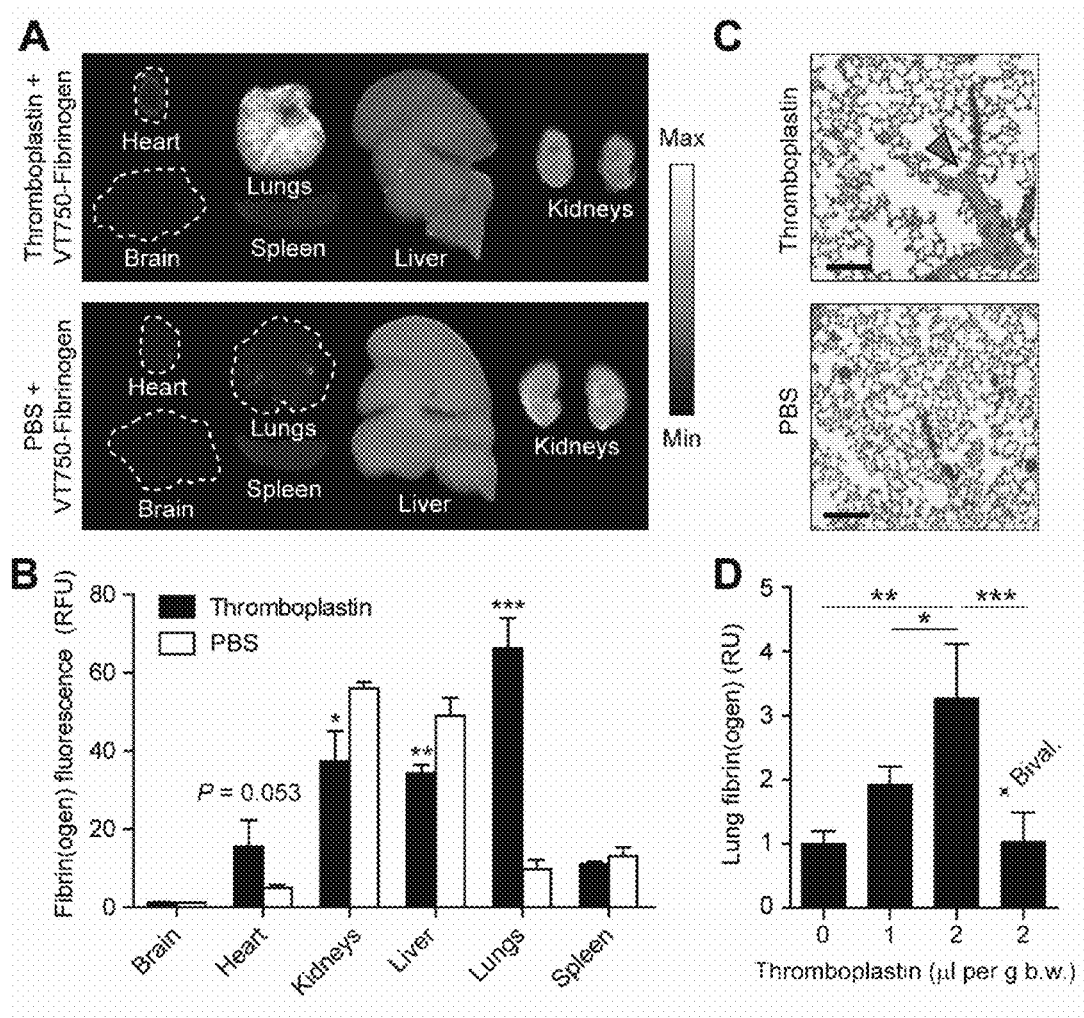
FIGS. 3A-D show the characterization of thromboplastin-induced thrombosis. (A) Near-infrared fluorescent scans of excised organs to monitor the deposition of VT750-labeled fibrinogen following intravenous injection of thromboplastin (2 µL/g b.w.) or PBS. (B) Quantification of the level of VT750-fibrin(ogen) deposited in organs harvested from thrombosis and control mice (*P<0.05, P<0.01, *P<0.005, Student's t-test; n=3 per group, s.d.). (C) Hematoxylin and eosin staining of lungs (scale bar=100 µm). Blue arrow denotes fibrin clot. (D) Quantification of fibrin deposited in the lungs in response to escalating doses of thromboplastin. Bival, bivalirudin (*P<0.05, P<0.01, *P<0.005, one-way ANOVA with Tukey post test; n=3-5 mice, s.e.).
Figure 7:
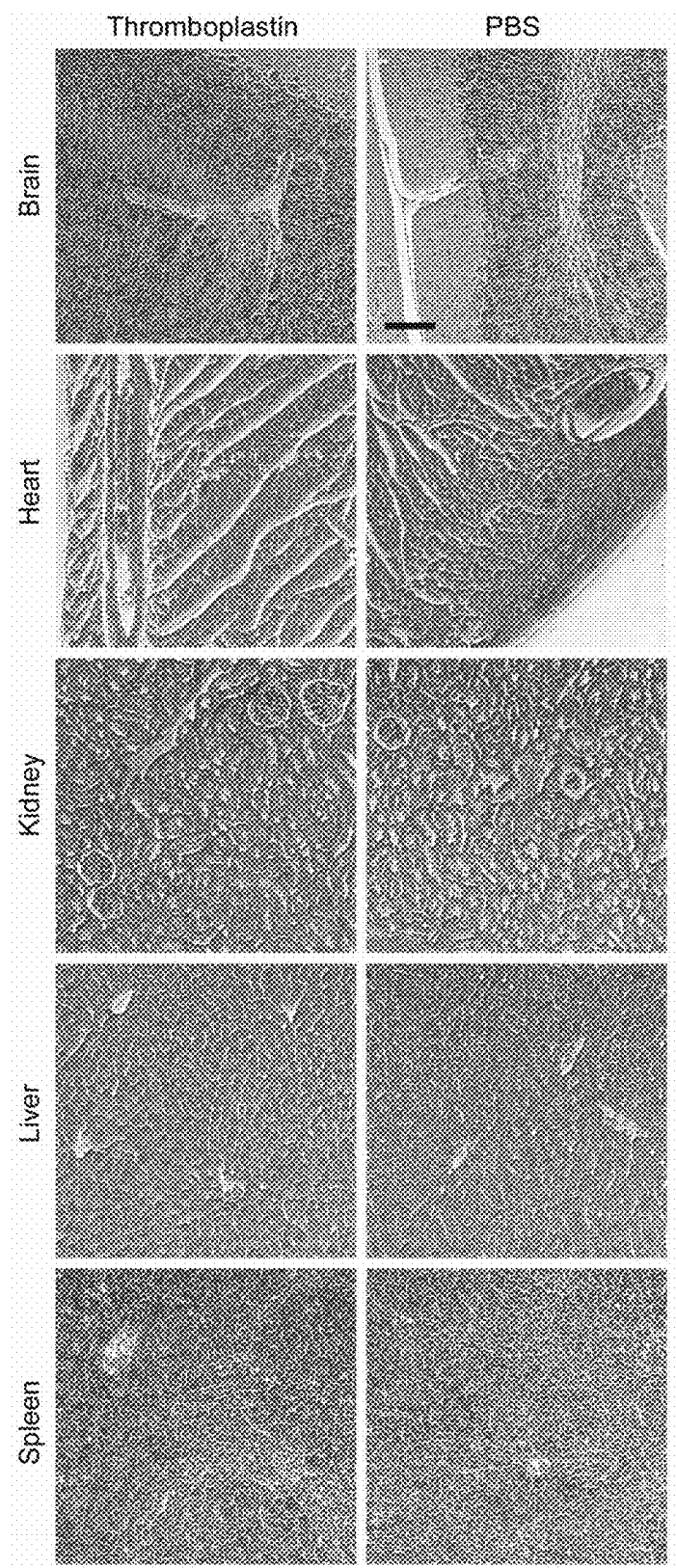
FIG. 7 shows hematoxylin and eosin staining of organ sections harvested from mice 30 minutes after administration of thromboplastin (scale bar=100 µm).
Figure 8:
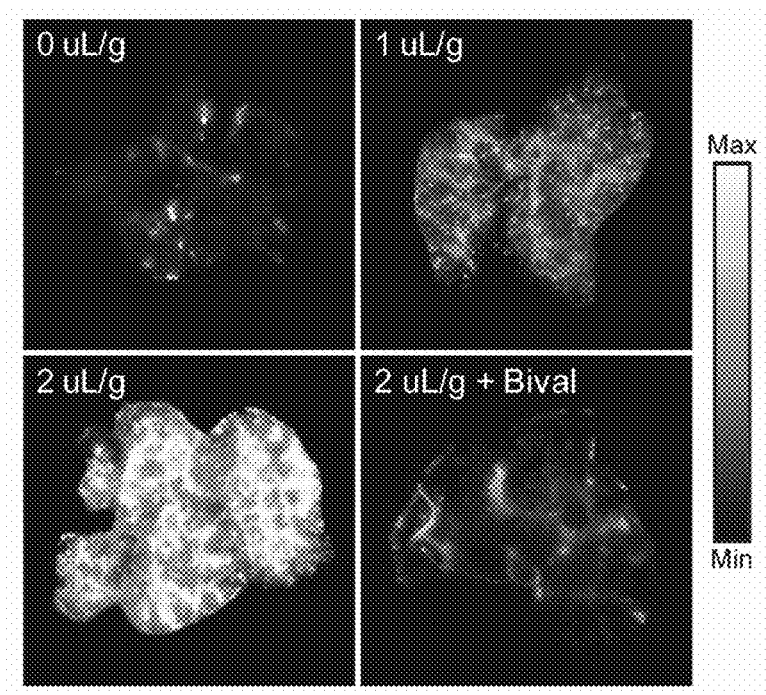
FIG. 8 shows near-infrared fluorescent scans of the level of VT750-fibrin(ogen) deposited in the lungs in response to increasing doses of thromboplastin and its inhibition by bivalirudin (Bival).

We next investigated the ability of the synthetic biomarkers to detect thrombosis in living mice induced via intravenous (i.v.) administration of thromboplastin. This model has been explored in the hematology literature to explore the role different vascular receptors play in host susceptibility to thrombosis and to probe the efficacy of new antithrombotic agents.[16] Thromboplastin triggers the clotting cascade through the extrinsic pathway via complexation of tissue factor and factor VII, and blood clots largely embolize to the lungs, recapitulating the life-threatening clinical condition of pulmonary embolism (PE). To quantify PE formation, mice were co-injected with thromboplastin and the clot precursor fibrinogen (labeled with the near-infrared fluorophore VT750) so that the formation of fibrin clots by thrombin-mediated proteolysis of fibrinogen could be quantified by fluorescence analysis of whole organs (FIG. 3A). Within 30 minutes of administration (dose=2 µl per g b.w.), a more than 6-fold increase was observed in the level of fibrin(ogen) deposited within the lungs and significant decreases in the kidneys and liver ($P<0.005$ by Student's t-test, n=3 mice; FIG. 3B), consistent with venous blood flow patterns that transport thrombi formed upon i.v. administration directly to the lungs from the heart. Histochemical analysis of tissue sections corroborated these findings by revealing the presence of blood clots in lung sections (arrow, FIG. 3C) that were absent in the other major organs (brain, heart, kidney, liver and spleen; FIG. 7) and in control animals. Animals given escalating but sublethal doses (observed LD50~3 µl per g b.w.) of thromboplastin accumulated fibrin(ogen) in the lungs in proportion to the dosage and PEs were readily prevented in animals pretreated with bivalirudin ($P<0.005$ by one-way ANOVA with Tukey post test, n=3-5 mice; FIG. 3D, FIG. 8), confirming that clot formation is largely driven by the activity of thrombin. Altogether, these results established the ability to precisely control total clot burden in a model that resembles the clinical pathology of venous thrombosis.[16b,17] In arterial thrombosis, activated platelets may play a larger role than thrombin in the recruitment of fibrinogen as evidenced by its treatment with antiplatelet therapies.[18] The applicability of this platform to platelet-driven thrombosis can be tested by employing models based on the systemic injection of platelet-aggregating agents such as collagen/epinephrine or ADP.[16b,19]

Figure 4:
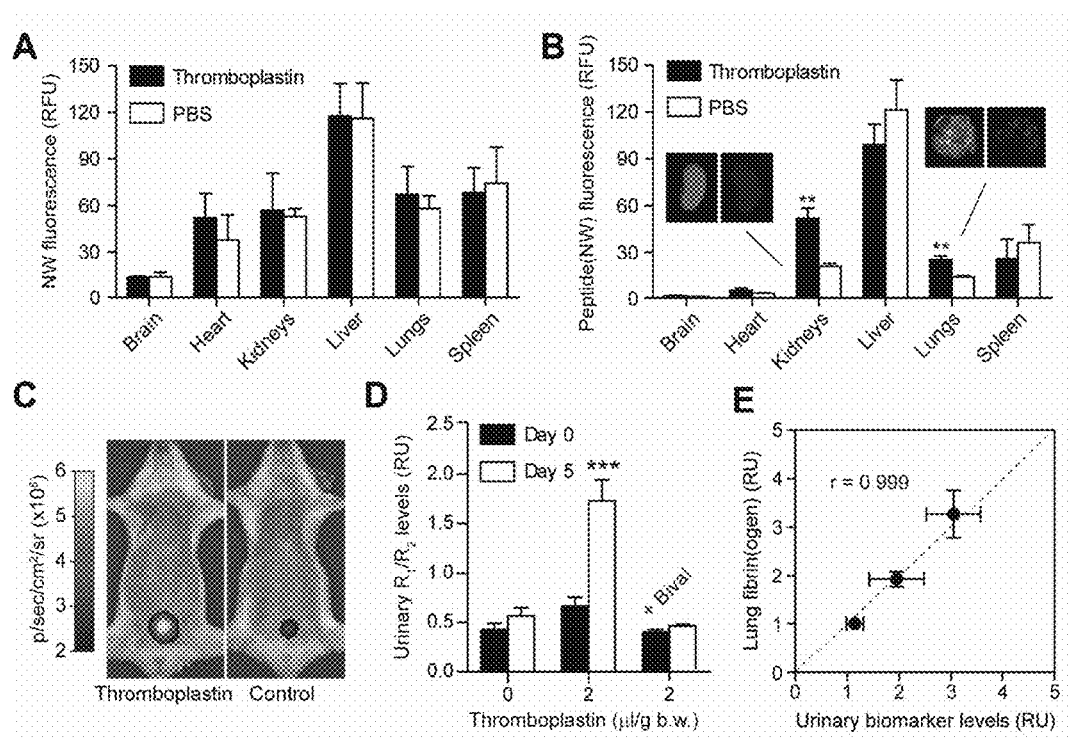
FIGS. 4A-E show noninvasive urinary detection of pulmonary embolism. (A) Quantification of the distribution of VT750-labeled NWs in organs excised from mice treated with thromboplastin or PBS (n=3 mice, s.d.). (B) Quantification of the fluorescent signal of organs after mice were infused mixtures of NWs conjugated with quenched substrates (labeled with VT750) and thromboplastin or PBS (P<0.01, Student's t-test; n=3 mice, s.d.). Inset shows representative fluorescent scans of the kidneys and the lungs. (C) In vivo fluorescent image after administration of NWs showing increased fluorescent signal localized to the bladders of mice challenged with thromboplastin. (D) Normalized urinary reporter levels ($R_1$/$R_2$) in response to thromboplastin. Bival, bivalirudin (*P<0.005, two-way ANOVA with Bonferroni post test; n=5 mice, s.e.). (E) Graph of VT750-fibrin(ogen) deposition in lungs versus normalized urinary biomarker levels.
Figure 9:
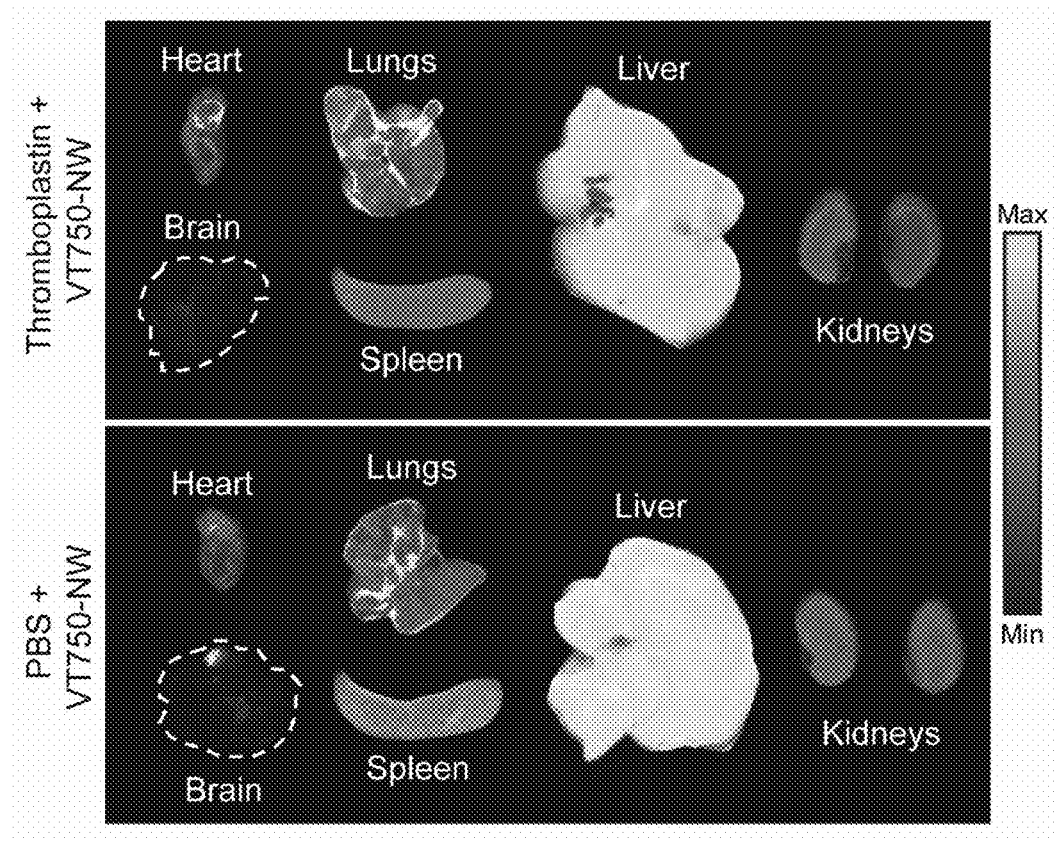
FIG. 9 shows near-infrared scan of VT750-NW distribution in organs following thromboplastin-induced thrombosis.
Figure 10:
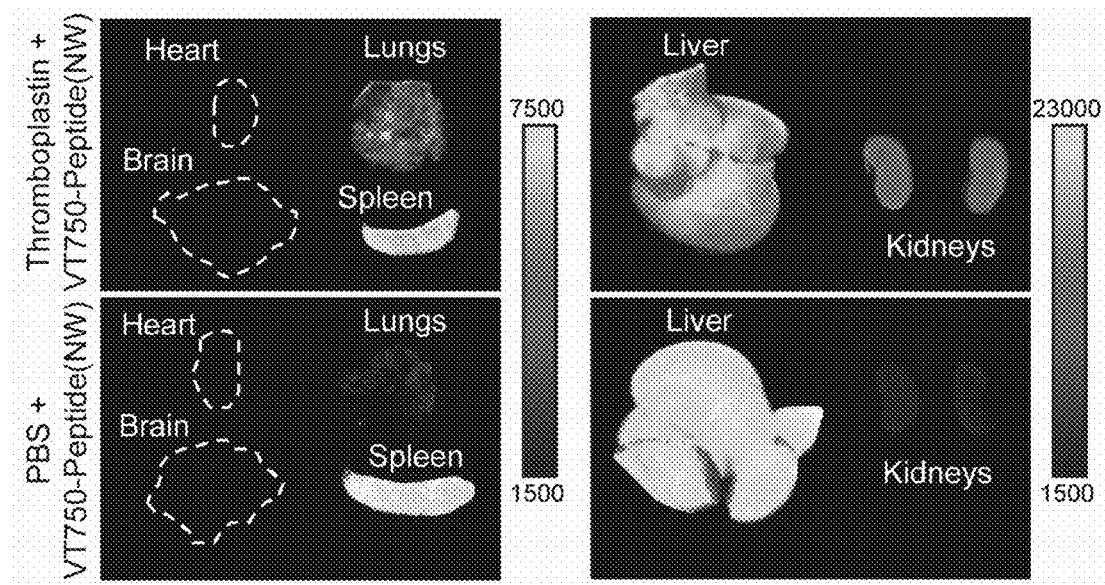
FIG. 10 shows near-infrared scan of VT750-substrate-reporter ($R_1$) distribution in organs following thromboplastin-induced thrombosis.
Figure 11:
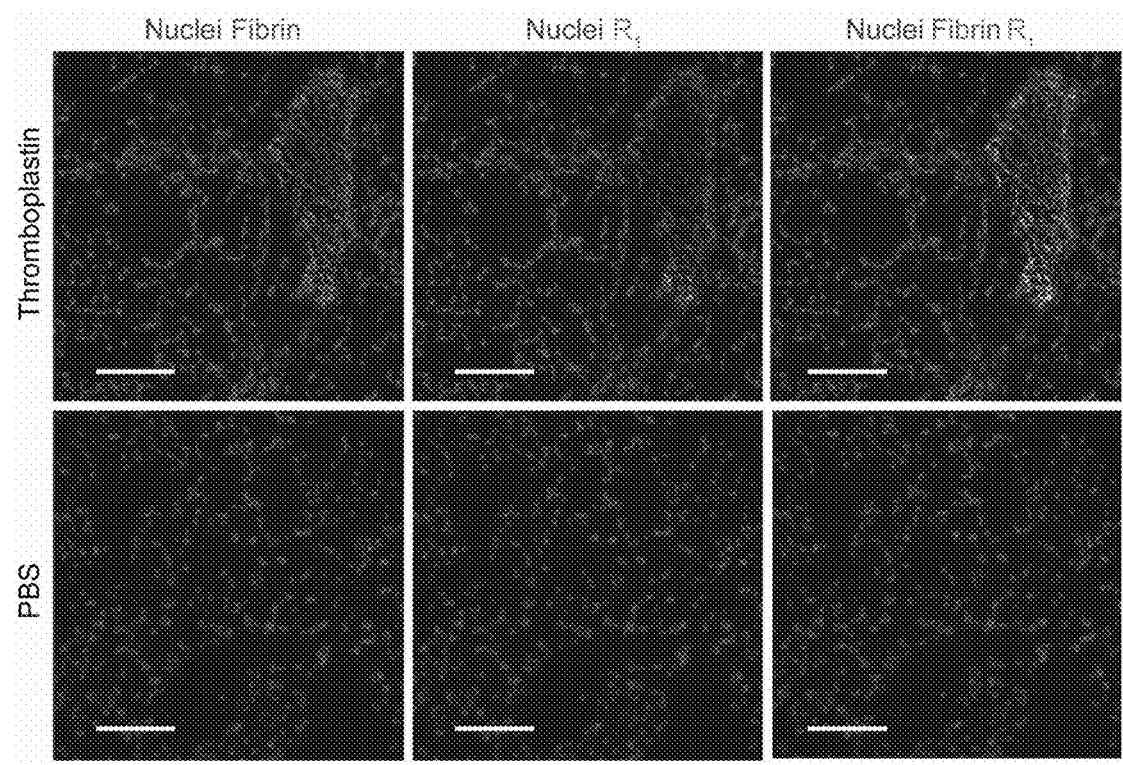
FIG. 11 shows immunofluorescent staining of lung sections following thromboplastin-induced thrombosis. Staining of fibrin deposition, $R_1$ accumulation, and nuclei in the lung is shown (scale bar=100 µm).

Example 5: Biomarker Nanoparticles can Systemically Survey the Vasculature for Thrombin Activity and Release Reporters at Sites of Thrombosis which are then Cleared Efficiently into the Host Urine Next, we characterized the pharmacokinetics of the synthetic biomarkers in the context of thrombosis. Mixtures of NWs were injected directly labeled with VT750 and thromboplastin into mice and observed no significant differences in NW distribution between the thromboplastin and control groups in all of the excised organs—including the lungs—indicating that thrombosis did not alter the biodistribution of the NW scaffold ($P>0.05$ by Student's t-test, n=3 mice; FIG. 4A, FIG. 9). To monitor peptide cleavage and trafficking of the cleaved fragments, we co-administered NWs conjugated with fluorescently-quenched substrates (labeled with VT750) and observed significant increases in fluorescence in the lungs and kidneys by ~1.8 and ~2.5 fold over healthy animals respectively ($P<0.01$ by Student's t-test, n=3 mice; FIG. 4B, FIG. 10). Paired with our earlier observations showing that thromboplastin did not alter the biodistribution of the NWs and induced blood clots that were localized to the lung (i.e. clots were not found in the kidneys), this finding provided evidence of peptide cleavage in the lungs (by their increased fluorescence) and kidney accumulation of freely-emitting fluorescent fragments. Immunofluorescent staining of lung sections further showed NW co-localization with fibrin, the sites of coagulation, that was absent in control sections (FIG. 11), supporting the hypothesis that circulating NWs can access local thrombi. To visualize the clearance efficiencies of the peptide fragments, mice were monitored by in vivo fluorescence imaging and observed a strong increase in fluorescent signal that was localized to the bladder of thrombotic mice relative to controls (FIG. 4C). Taken together, the data illustrate that the biomarker nanoparticles of the invention can systemically survey the vasculature for thrombin activity and release reporters at sites of thrombosis which are then cleared efficiently into the host urine.

Figure 12:
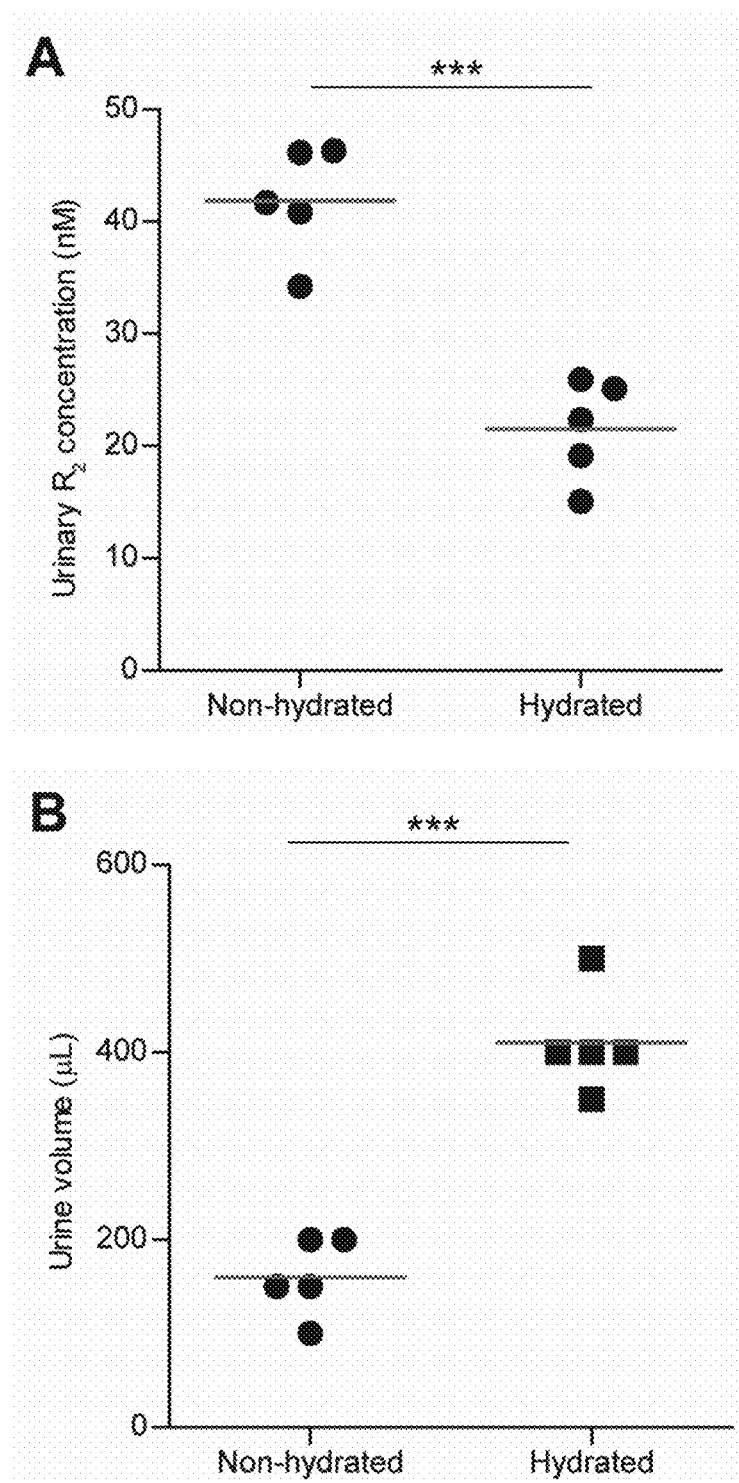
FIGS. 12A-B show the impact of hydration state on urinary reporter levels. (A) Quantification of $R_2$ in urine from non-hydrated versus hydrated mice via ELISA (*P<0.005, Student's t-test; n=5 mice.). (B) Urine volume collected from non-hydrated mice versus mice hydrated with 10% body weight equivalent of PBS injected subcutaneously, two hours after administration (*P<0.005, Student's t-test; n=5 mice).

Example 6: Biomarker Nanoparticles can Monitor Thrombin Activity in Living Mice and Quantitatively Measure the Aggregate Burden of Sublethal PEs from the Urine by ELISA The concentration of analytes in the urine is mainly dependent on the hydration state of the host (ranging from 50-1200 mOsm/kg $H_2O$ in humans)[20] and is affected by many external factors (e.g. circadian rhythm, diet, activity, and others). Approaches to determine the concentration of urine include measuring the level of creatinine,[21] a byproduct of muscle metabolism that filters into the urine at a steady state when at rest, or i.v. administration of inulin,[22] a polysaccharide that is not actively absorbed or secreted by the kidneys and whose appearance in urine is directly related to the rate of urine production. It is hypothesized that because the free reporters ($R_1$, $R_2$) are built from Glu-fib which is likewise biologically inert,[14] their filtration into urine following i.v. administration would be indicative of the concentration of urine. To test this, urinary levels were measured of $R_2$ in mice that received a subcutaneous bolus of saline equivalent to 10% of their body weight to create a state of over-hydration and found it was diluted by ~50% compared to non-hydrated mice allowed to drink ad libitum ($P<0.005$ by Student's t-test, FIG. 12A). The volume of urine collected during the experimental period (~2.5 hrs) also increased by over 2.5 fold ($P<0.005$ by Student's t-test, FIG. 12B), which together showed that the free reporters could be used to monitor the hydration state and urine concentration of the animals. We next sought to monitor thromboplastin-induced PEs by urine analysis of the response of the synthetic biomarkers to thrombin activity. To simulate serial monitoring that frequently occurs in inpatient settings, we first determined the basal activity in healthy cohorts of animals each receiving thrombin-sensitive NWs and a free reporter ($R_2$) for urine normalization (FIG. 4D). After five days to allow NWs to fully clear (half-life ~6 hours),[6] a mixture of thromboplastin, NWs, and $R_2$ were administered into the same mice and quantified reporter levels by ELISA. When compared to their healthy state (Day 0), the induction of PEs (Day 5) resulted in significant elevations of up to three fold in the level of urinary cleavage fragments ($P<0.005$ by two-way ANOVA with Bonferroni post test, n=5 mice; FIG. 4D). In mice treated with bivalirudin prior to thrombotic challenge (dose=2 µl per g b.w.), reporters levels were abrogated, consistent with earlier findings showing the ability of bivalirudin to inhibit thrombin activity and prevent the formation of PEs. When the urinary biomarker marker levels from thromboplastin-challenged mice were normalized to their healthy urine samples collected from day 0 (FIG. 13) and directly compared to the amount of fibrin(ogen) deposited at identical doses of thromboplastin (FIG. 3D), a striking correlation was found to the disease burden with a correlation coefficient of 0.99 (Pearson's r, FIG. 4E). Collectively, the findings showed that synthetic biomarkers can monitor thrombin activity in living mice and quantitatively measure the aggregate burden of sublethal PEs from the urine by ELISA.

Example 7: Demonstration of Specific Cleavage In Vivo Using ELISA

Figure 14:
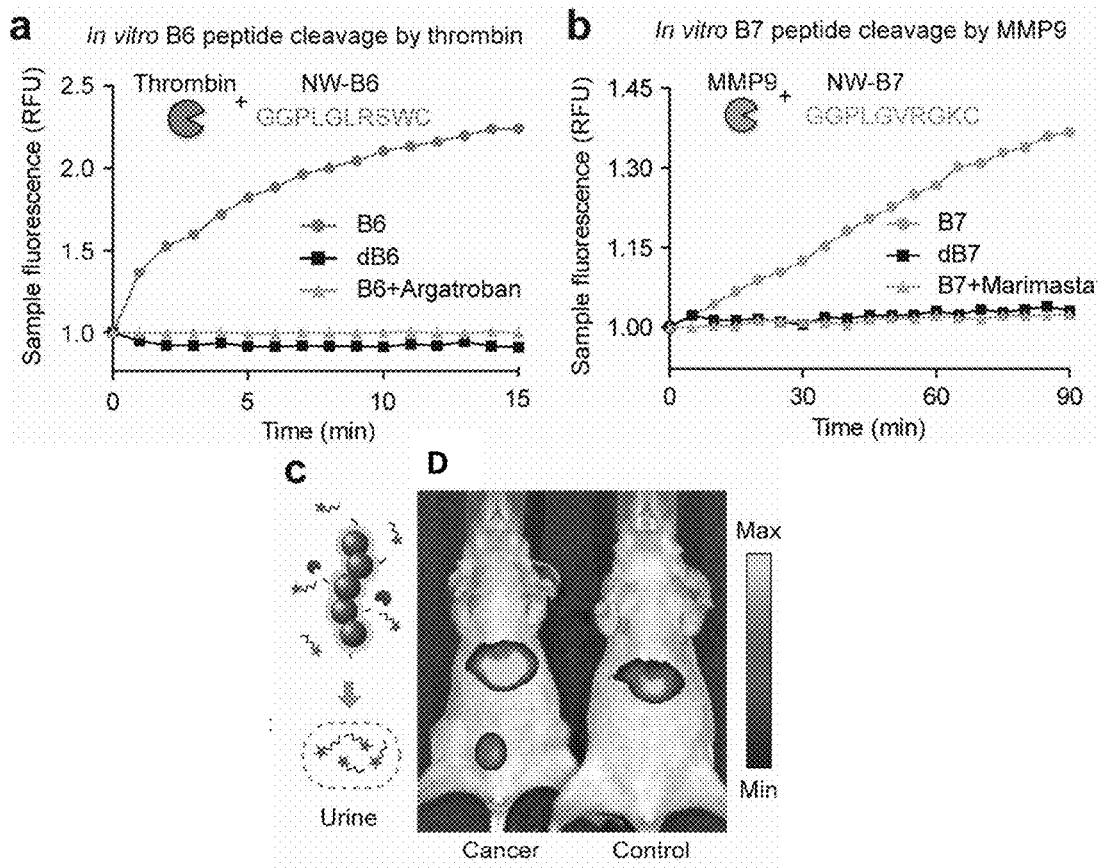
FIGS. 14 A-D show protease-sensitive nanoparticles detect disease from the urine. (A and B) is a set of graphs showing proteolysis of nanoparticles coated with fluorophore-labeled peptide substrate (A)(B6) specific for thrombin or MMP9 (B) (B7), their protease-resistant d-isomers (dB6, dB7), and in the presence of protease inhibitors (argatroban and Marimastat). (C) is a schematic showing the method. (D) Whole animal fluorescent imaging showing urinary accumulation of cleaved peptide in mice harboring flank tumors.

To develop protease-sensitive nanoparticles, we selected two peptide substrates (B6 and B7 respectively) previously reported to be specific for thrombin and MMP9 and demonstrated the respective capacity for cleavage by recombinant proteases (i.e. thrombin and MMP9) in a fluorogenic nanoparticle assay (FIG. 14a,b). Thrombin, a circulating protease involved in coagulation, is strongly activated during thrombosis while MMP9, a matrix degrading enzyme, is frequently dysregulated in many solid cancers. In mouse models of thrombosis or colorectal cancer, a significant accumulation of fluorescently-labeled cleavage fragments was observed in the host urine following intravenous infusion of thrombin- or MMP9-specific nanoparticles (FIG. 14c).

Figure 15:
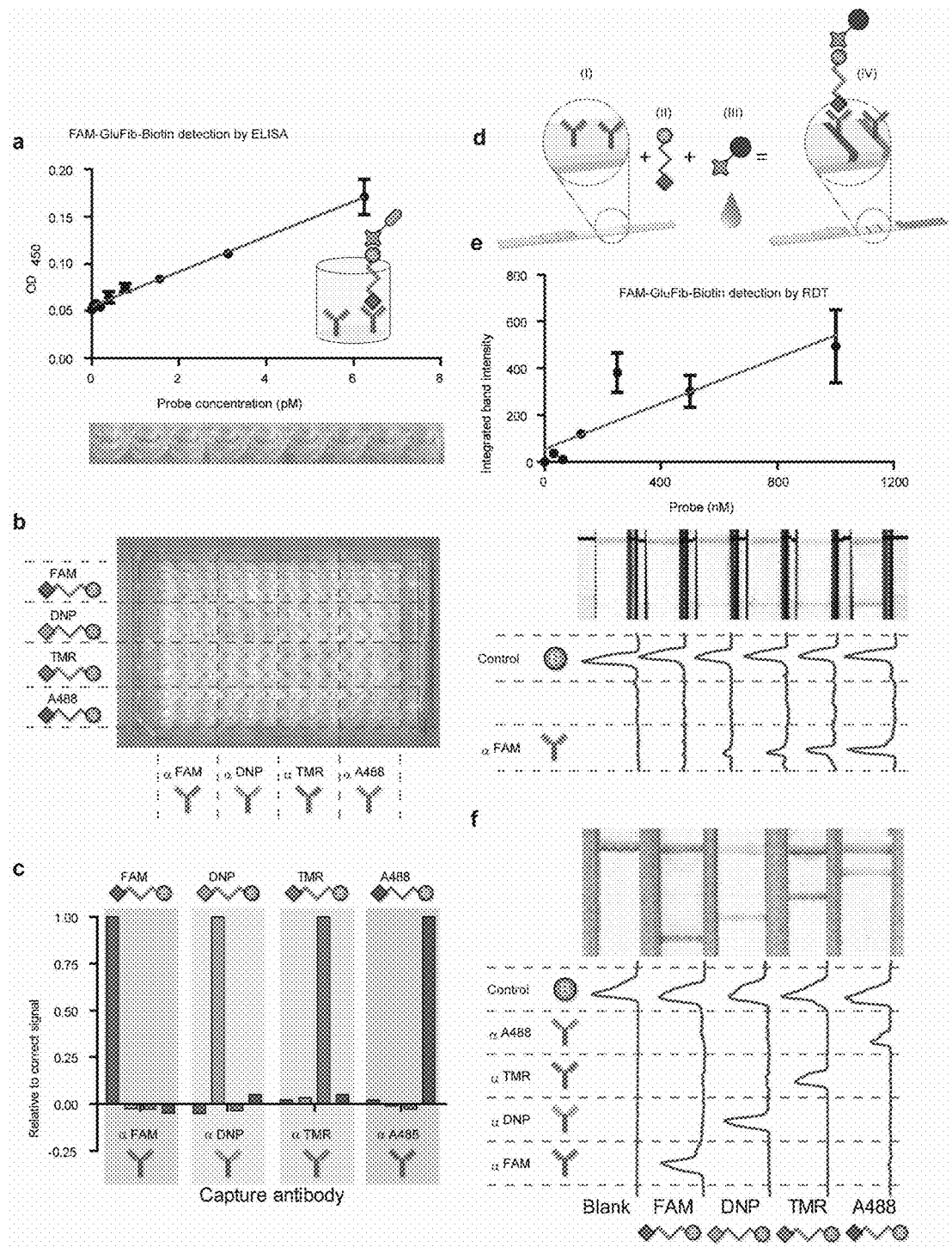
FIGS. 15A-F show affinity-based detection of synthetic urinary biomarkers. (A) Schematic of antibody and hapten-reporter sandwich complex and lower limit of detection showing pM sensitivity. (B) Picture of developed 96-well plate showing specificity of absorbed antibodies for four distinct hapten-encoded reporters. (C) Optical quantification of plate assay revealed negligible cross-reactivity between non-cognate antibody-hapten pairs. (D) Schematic of a paper-based lateral flow assay. (E) Quantification of the lower limit of detection of a single reporter on paper (top) and its intensity profiles (bottom). (F) Spatially-encoded paper test strip exposed to different urine samples spiked with a distinct reporter. Test lines appeared only in regions printed with the specific antibody.

To construct a ligand-based reporter, we first modified the prototypic peptide scaffold Glutamate-Fibrinopeptide B (GluFib, EGVNDNEEGFFSAR, SEQ ID NO. 1) at one terminus with the hapten Fluorescein (FAM) and at the opposing end with biotin to create reporter 1 (R1). Because haptens, such as FAM, can be readily captured by antibodies, we first tested the ability to detect the reporter by ELISA (FIG. 15a). Analogous to a conventional sandwich assay, a 96-well plate was coated with a-FAM antibodies, layered on R1 for capture by α-FAM, and completed the sandwich complex through the addition of streptavidin-HRP which binds to biotin. Following plate development with the chromogenic substrate TMB, the presence of R1 at sub-pM concentrations was detected (FIG. 15a), establishing the ability to construct affinity assays for ligand-modified reporters. To build a family of orthogonal reporters, four distinct agents were synthesized by creating derivatives of GluFib modified at opposite termini with a unique hapten (i.e., FAM, TAMRA, DNP, or Alexa488) and biotin (labeled R1-R4 respectively; FIG. 15b). To test cross-reactivity, solutions spiked with R1, R2, R3, or R4 was applied to a 96-well plate coated in distinct regions with α-FAM, α-DNP, α-TAMRA, or α-Alexa488 antibodies. Consistent with their specificities, the strongest signal intensities appeared only in wells containing matched antibody-hapten pairs while by contrast, signal intensities from non-matched combinations were negligible (FIG. 15b,c). Collectively, these studies showed that the specificity of hapten-antibody interactions can be exploited to build a family of orthogonal reporters.

Example 8: Demonstration of Specific Cleavage In Vivo Using a Paper Based Assay

A paper-based, lateral flow assay (LFA) was developed to detect the reporters according to methods of the invention. The biochemistry of the LFA is similar to that used in the ELISA assay, so no change in the reporter structure was required. For the LFA, the antibodies were bound to a nitrocellulose membrane instead of a plastic plate, and the streptavidin was bound to gold nanoparticles, which facilitated optical detection of the reporters (FIG. 15d). First, the sample, containing the reporters was applied to a cellulose pad that serves as a reservoir to deliver the sample to the rest of the strip. The sample passes through a "conjugate pad" containing gold nanoparticles (10-100 nm in diameter) that are coated with streptavidin. The biotin moiety on the reporters bound to the streptavidin on the nanoparticles. The sample containing the nanoparticle-reporter conjugates then wicked down a nitrocellulose membrane, onto which a stripe of α-FAM antibody has been deposited. The FAM moiety on the reporter binds to the α-FAM antibody as the sample passed over the stripe, and the nanoparticle-reporter conjugates accumulated on the stripe. If the reporter is present in sufficient concentration, the gold nanoparticles will be visible to the naked eye as a red line on the nitrocellulose membrane. Using this assay R1 was detected down to ~100 nM concentrations in spiked samples using the LFA (FIG. 15e). Additionally, we have successfully measured multiple orthogonal reporters on the same test strip (FIG. 15f) by using multiple stripes containing antibodies for the various haptens in the reporter library. No loss of specificity was observed relative to the ELISA format, indicating the LFA format is equally effective as a diagnostic tool with the benefit of being "labor-free."

Figure 16:
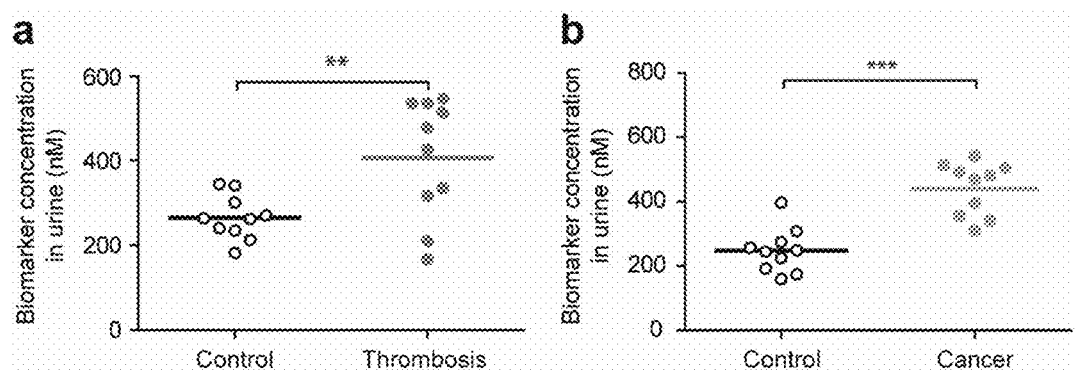
FIGS. 16A-B show synthetic urinary biomarkers discriminate disease. ELISA analysis of urine samples from mice that received NW injections showed elevated urinary biomarkers that detected thrombosis (A) or cancer (B) over healthy controls.

To demonstrate the ability to detect protease activity in living animals by affinity assays, substrates B6 and B7 were conjugated with hapten-encoded reporters to nanoparticles. Following nanoparticle administration, the urine was analyzed by ELISA or LFAs and detected a marked increase in the amount of cleaved reporters present in the diseased urine samples relative to the healthy animals, illustrating the ability to discriminate disease noninvasively from urine (FIG. 16a,b). Altogether, these studies demonstrate the utility of the claimed invention and highlight the ability of the compositions of the invention to be used as ligand-encoded 'synthetic biomarkers' that can be readily detected by established and low-cost affinity assays.

Example 9: Protease-Sensitive Nanoparticles for the Monitoring of Urinary Disease To develop synthetic biomarkers for thrombosis and cancer, nanoparticles were first designed for sensing the activity of the proteases thrombin and matrix metalloproteinase 9 (MMP9). Poly-(ethylene glycol)-coated iron oxide nanoworms (NWs)—a long-circulating nanoparticle formulation previously characterized by collaborators and the lab were functionalized[28,29]—with fluorescein-labeled derivatives of thrombin- and MMP9-cleavable substrates (PLGLRSW, SEQ ID NO: 3, and PLGVRGK, SEQ ID NO: 4, respectively[30]) at a surface valency of 20-30 peptides per NW to induce intermolecular quenching (FIG. 1A) Thrombin-sensitive NWs were incubated with thrombin and observed a rapid increase in sample fluorescence as cleaved peptide fragments released into solution fluoresced freely to test the efficiency of peptidolysis. No increase in fluorescence was observed in the presence of Argatroban, a direct thrombin inhibitor, or when the substrate was synthesized with protease-resistant D-stereoisomers, indicating that thrombin activity was required to activate the NWs. Similar increases in sample fluorescence were observed when MMP-sensitive NWs were incubated with MMP9 and no activity when the broad-spectrum MMP inhibitor Marimastat or D-isomer substrates were used. Together these findings showed that peptides on the surface of NWs can be efficiently cleaved by thrombin or MMP9.

NWs with substrates labeled with carrier peptide-linked near infrared fluorophores to monitor peptide traffic and cleavage by in vivo fluorescence imaging were synthesized. The near infrared fluorophore VT750 (N-terminal) was conjugated to the peptide Glutamate-Fibrinopeptide B (Glu-Fib, sequence eGvndneeGffsar, SEQ ID NO: 1), which were synthesized with D-amino acids (lower case) to confer stability against protease activity, to promote renal clearance and to enable in vivo fluorescent visualization of the peptide-fluorophore reporter released by substrate proteolysis[30,31,32].

A murine model of thrombosis was chosen in which the onset of clotting is controlled by the IV administration of collagen and epinephrine to activate platelets and thrombin, forming blood clots that embolize to the lungs[33]. Consistent with previous findings, co-administration of NWs to mice challenged with collagen and epinephrine resulted in a pronounced increase in their urinary and lung fluorescence relative to healthy controls, indicating in vivo cleavage and renal clearance of peptides. To apply to CRC, MMP9-sensitive NWs were infused into nude mice bearing subcutaneous human colorectal tumors (LS 174T), formed by a cell line that secretes MMP9[34], and observed similar increases in fluorescence localized to the bladder. Immunofluorescent staining of tumor sections confirmed NW extravasation from the vasculature into the tumor interstitium. These results verified the ability of thesynthetic biomarkers to probe disease sites and release cleaved peptide fragments into the host urine.

Example 10: Detecting Ligand-Encoded Reporters by Sandwich Complexes

We next sought to design a panel of ligand-encoded reporters that can be detected by protein-based sandwich complexes. The formation of a sandwich complex requires a target antigen to express two distinct epitopes that bind separately to a capture and detection agent; the ligands fluorescein (FAM; capture) and biotin (detection) were conjugated to the opposing termini of the same D-stereoisomer GluFib to construct the synthetic htertobifunctional reporter R1. GluFib functions as a molecular spacer, allowing FAM and biotin to bind freely to their cognate proteins a-FAM antibody (a-R1) and streptavidin respectively, and as before, promotes clearance of the reporter as GluFib is biologically inert and efficiently filtered by the kidneys[30,31,32]. It was first determined whether urine samples spiked with R1 could be detected by sandwich ELISA, a standard assay used in clinical laboratories. Serial dilutions of R1 were applied to a 96-well plate coated with a-R1 antibodies to immobilize R1 before neutravidin-horseradish peroxidase (NA-HRP) was added to catalyze the development of the chromogenic substrate 3,3',5,5'-tetramethylbenzidine (TMB), revealing a linear dose dependence from ~6 pM down to the limit of detection (LOD) of ~0.1 pM. This favorably compared LOD with the sensitivity at which naturally occurring biomarkers such as prostate specific antigen[35] can be detected by ELISA, establishing the ability to design synthetic sandwich assays by harnessing ligand-protein interactions. An analysis of linear regions of different reporters can be found in Table 3 below.

TABLE 3

| Reporter | Reporter structure | Linear range (pM) | Slope | Intercept | $R^2$ |
|---|---|---|---|---|---|
| 1 | FAM-GluFib-Biotin | 0.09-6.25 | 0.01832 +/- 0.001611 | 0.05723 +/- 0.003875 | 0.9486 |
| 2 | DNP-GluFib-Biotin | 7.35-87 | 0.001832 +/- 0.00007243 | 0.06115 +/- 0.002290 | 0.9877 |
| 3 | TMR-GluFib-Biotin | 54.5-700 | 0.001163 +/- 0.00003436 | 0.09762 +/- 0.008225 | 0.9922 |
| 4 | AF488-GluFib-Biotin | 23-200 | 0.001259 +/- 0.00003604 | 0.07760 +/- 0.002649 | 0.9911 |

To generalize the approach and construct a multiplexed library of reporters, additional heterobifunctional derivatives of GluFib were synthesized by pairing the capture ligands dinitrophenyl (DNP), tetramethylrhodamine (TMR) and ALEXA FLUOR® 488 (AF488) with biotin to create reporters R2-R4 respectively. Similar to fluorescein, these ligands were selected because they are well tolerated by living organisms, stable, and do not elicit immune responses unless coupled to a potent immunogen[36]. Independent sandwich ELISAs were developed by using the antibodies α-DNP (α-R2), α-TMR (α-R3), or α-AF488 (α-R4) to capture R2, R3, or R4, respectively, and identified the LOD and working linear ranges for each, which were also within the typical values expected for sandwich ELISAs. Assaying for specificity revealed an increase in sample intensity in wells that contained matched antibody-ligand pairs while cross-reactivity in non-matched wells was below the LOD of the cognate detection signal. The results showed that ligand-encoded reporters can be sensitively and specifically detected in urine by sandwich ELISA.

Similar performance metrics were observed for separate LFAs customized for the remaining reporters. Statistics for linear regions of R1-4 standard curves can be found in Table 4 below.

TABLE 4

| Reporter | Reporter structure | Linear range (pM) | Slope | Intercept | $R^2$ |
|---|---|---|---|---|---|
| 1 | FAM-GluFib-Biotin | 0.09-6.25 | 0.01832 +/- 0.001611 | 0.05723 +/- 0.003875 | 0.9486 |
| 2 | DNP-GluFib-Biotin | 7.35-87 | 0.001832 +/- 0.00007243 | 0.06115 +/- 0.002290 | 0.9877 |
| 3 | TMR-GluFib-Biotin | 54.5-700 | 0.001163 +/- 0.00003436 | 0.09762 +/- 0.008225 | 0.9922 |
| 4 | AF488-GluFib-Biotin | 23-200 | 0.001259 +/- 0.00003604 | 0.07760 +/- 0.002649 | 0.9911 |

Example 11: Detection of Protease Activity and Paper Assay Development

Paper-based LFAs, developed more than two decades ago to detect human chorionic gonadotropin as a home pregnancy test, have since been expanded for use in diverse settings to detect pathogens, drugs, hormones, and metabolites[37]. LFAs detect antigens by a sandwich complex in which capture antibodies are adsorbed onto a highly porous test strip, such as a nitrocellulose membrane, which serves to wick fluids and transport analytes from the sample pad to the capture regions. The immobilized analytes are then visualized by a detection agent coupled to nanoparticles (typically gold or latex nanospheres) that create a colored line detectable by eye without enzymatic amplification.

Here we sought to determine whether ligand-encoded reporters could be detected on paper. Using a low-volume robotic liquid handler, a-R1 and a-streptavidin antibodies were deposited to create test and control lines, respectively, on nitrocellulose paper strips. Unprocessed mouse urine samples spiked with R1 were then applied to the sample pads followed by a solution containing gold nanoparticle-conjugated streptavidin. Colored lines appeared where the test antibodies were printed, indicating R1 capture from urine and detection as a sandwich complex. Quantitative scans of LFAs used to analyze serial dilutions of R1 revealed a LOD of ~1 nM and a working linear range of ~1-7 nM.

Capture antibodies were printed into four parallel test lines relative to a control line and analyzed urine samples that contained one of the four reporters to enable multiplex reporter detection. Only the test lines printed with the cognate capture antibody developed a positive signal, highlighting the LFA's specificity and the capacity to detect distinct reporters with single spatially-encoded paper strips, similar to the results from the ELISA tests.

Thrombin-sensitive substrates were conjugated in tandem with R3 onto NWs to detect protease activity by LFAs. Following in vitro substrate cleavage by thrombin, the peptide fragments were collected by size-exclusion filtration. Cleaved R3 was readily detected from the filtrate by LFA, developing into significantly darker test lines when compared to control samples not exposed to thrombin (p=0.0022). Similar results were obtained when filtrate collected after incubation of R2-encoded MMP-sensitive NWs with MMP9 was analyzed by LFA (p=0.0022). These results demonstrated that the activity of distinct proteases can be detected by paper-based LFAs.

Example 12: Disease Detection on Paper with Synthetic Urinary Biomarkers

Urine concentration is dependent on many host and environmental factors (e.g. diet, activity level, medical history, circadian rhythm); therefore, we sought to develop a normalization strategy for the test. It was hypothesized that co-administered free reporters would pass into the urine independent of disease state and could be used to normalize the level of reporters released by protease activity. A mixture of free R4 and thrombin-sensitive NWs (labeled with R3) were infused into healthy or thrombotic cohorts of mice and collected all urine for 30 m post-injection to investigate this approach. Urinary concentrations of R4 were statistically equivalent between the two groups by ELISA, indicating unbiased clearance of the free reporter (p=0.25). By contrast, urinary levels of R3, the reporter of thrombin activity, significantly increased in mice harboring thrombi when quantified independently ($p<10^{-4}$) or when normalized against R4 ($p<10^{-4}$). Using a paper strip printed with multiple capture antibodies, the urinary levels of R3 and R4 were analyzed simultaneously and similarly observed a statistically significant increase in the ratio of R3/R4 in diseased urine samples compared to healthy controls (p=0.0015). The rate of true positives (sensitivity) and false positives (1-specificity) was analyzed by receiver-operating characteristic (ROC) curves and found that the multiplexed paper test discriminated urine from thrombotic versus control mice accurately, with an area under the curve (a.u.c) of 0.92 (p=0.0015).

The normalization strategy developed for thrombosis by infusing a solution containing free R4 and R2-encoded MMP-sensitive nanoparticles into nude mice bearing subcutaneous LS 174T colorectal tumors and collecting all urine up to 1 hour post-injection was adopted to establish the ability to detect solid cancers. Diseased mice cleared R4 with an efficiency statistically equivalent to healthy animals (p=0.92) while the urinary concentrations of R2, the reporter of in vivo MMP activity, or its normalized intensity (R2/R4) were both significantly elevated in tumor-bearing mouse urine by ELISA (p=0.0039, p=0.0098). By ROC analysis, this urine test was highly accurate and discriminated CRC with an a.u.c of 0.90 (p=0.0025). Analysis of the same urine samples by LFA demonstrated a significant increase in the ratio of R2/R4 in urine collected from tumor-bearing but not from control mice (p=0.002). These results showed that LFAs can both detect synthetic biomarkers directly from the urine and discriminate noncommunicable diseases with significant predictive power.

REFERENCES

[1] a) T. Pisitkun, R. Johnstone, M. A. Knepper, *Molecular & Cellular Proteomics* 2006, 5, 1760; b) J. Barratt, P. Topham, *Canadian Medical Association Journal* 2007, 177, 361; c) J. Adachi, C. Kumar, Y. Zhang, J. V. Olsen, M. Mann, *Genome Biol* 2006, 7, R80.

[2] a) L. Wide, C. A. Gemzell, *Acta Endocrinologica* 1960, XXXV, 261; b) L. A. Cole, A. Kardana, D. B. Seifer, H. C. Bohler, *Journal of Clinical Endocrinology & Metabolism* 1994, 78, 497.

[3] a) Y. Hinokio, S. Suzuki, M. Hirai, M. Chiba, A. Hirai, T. Toyota, *Diabetologia* 1999, 42, 995; b) T. Nishikawa, T. Sasahara, S. Kiritoshi, K. Sonoda, T. Senokuchi, T. Matsuo, D. Kukidome, N. Wake, T. Matsumura, N. Miyamura, M. Sakakida, H. Kishikawa, E. Araki, *Diabetes Care* 2003, 26, 1507; c) L. L. Wu, C. C. Chiou, P. Y. Chang, J. T. Wu, *Clinica Chimica Acta* 2004, 339, 1; d) K. Rossing, H. Mischak, M. Dakna, P. Zürbig, J. Novak, B. A. Julian, D. M. Good, J. J. Coon, L. Tarnow, P. Rossing, o. b. o. t. P. Network, *Journal of the American Society of Nephrology* 2008, 19, 1283.

[4] a) G. H. Tesch, *Nephrology* 2010, 15, 609; b) R. G. Fassett, S. K. Venuthurupalli, G. C. Gobe, J. S. Coombes, M. A. Cooper, W. E. Hoy, *Kidney Int* 2011, 80, 806; c) J. Mishra, Q. Ma, A. Prada, M. Mitsnefes, K. Zahedi, J. Yang, J. Barasch, P. Devarajan, *Journal of the American Society of Nephrology* 2003, 14, 2534.

[5] a) M. A. Moses, D. Wiederschain, K. R. Loughlin, D. Zurakowski, C. C. Lamb, M. R. Freeman, *Cancer Research* 1998, 58, 1395; b) R. Roy, J. Yang, M. A. Moses, *Journal of Clinical Oncology* 2009, 27, 5287.

[6] G. A. Kwong, G. von Maltzahn, G. Murugappan, O. Abudayyeh, S. Mo, I. A. Papayannopoulos, D. Y. Sverdlov, S. B. Liu, A. D. Warren, Y. Popov, D. Schuppan, S. N. Bhatia, *Nature Biotechnology* 2013, 31, 63.

[7] S. L. Robbins, V. Kumar, R. S. Cotran, *Robbins and Cotran pathologic basis of disease*, Saunders/Elsevier, Philadelphia, Pa., 2010.

[8] a) E. W. Davie, J. D. Kulman, *Semin Thromb Hemost* 2006, 32, 003; b) J. A. Huntington, *Journal of Thrombosis and Haemostasis* 2005, 3, 1861.

[9] a) F. A. Jaffer, C.-H. Tung, R. E. Gerszten, R. Weissleder, *Arteriosclerosis, Thrombosis, and Vascular Biology* 2002, 22, 1929; b) C.-H. Tung, R. E. Gerszten, F. A. Jaffer, R. Weissleder, *ChemBioChem* 2002, 3, 207; c) E. S. Olson, M. A. Whitney, B. Friedman, T. A. Aguilera, J. L. Crisp, F. M. Baik, T. Jiang, S. M. Baird, S. Tsimikas, R. Y. Tsien, Q. T. Nguyen, *Integrative Biology* 2012, 4, 595.

[10] M. Whitney, E. N. Savariar, B. Friedman, R. A. Levin, J. L. Crisp, H. L. Glasgow, R. Lefkowitz, S. R. Adams, P. Steinbach, N. Nashi, Q. T. Nguyen, R. Y. Tsien, *Angewandte Chemie International Edition* 2013, 52, 325.

[11] a) H. Bounameaux, P. de Moerloose, A. Perrier, G. Reber, *Thromb Haemost* 1994, 71, 1; b) J. S. Ginsberg, P. S. Wells, C. Kearon, D. Anderson, M. Crowther, J. I. Weitz, J. Bormanis, P. Brill-Edwards, A. G. Turpie, B. MacKinnon, M. Gent, J. Hirsh, *Annals of Internal Medicine* 1998, 129, 1006; c) R. Becker, F. Spencer, *J Thromb Thrombolysis* 1998, 5, 215.

[12] J.-H. Park, G. von Maltzahn, L. Zhang, A. M. Derfus, D. Simberg, T. J. Harris, E. Ruoslahti, S. N. Bhatia, M. J. Sailor, *Small* 2009, 5, 694.

[13] a) G. A. Mitchell, R. J. Gargiulo, R. M. Huseby, D. E. Lawson, S. P. Pochron, J. A. Sehuanes, *Thrombosis Research* 1978, 13, 47; b) K. Asai, M. Asai, *Clin Chim Acta* 1984, 144, 163; c) M. L. Larsen, U. Abildgaard, A. N. Teien, K. Gjesdal, *Thrombosis Research* 1978, 13, 285; d) D. S. Rijkers, S. J. H. Wielders, G. I. Tesser, H. C. Hemker, *Thrombosis Research* 1995, 79, 491.

[14] T. A. Morris, J. J. Marsh, C. M. Burrows, P. G. Chiles, R. G. Konopka, C. A. Pedersen, *Thrombosis Research* 2003, 110, 159.

[15] N. L. Rosi, C. A. Mirkin, *Chemical Reviews* 2005, 105, 1547.

[16] a) E. J. Weiss, J. R. Hamilton, K. E. Lease, S. R. Coughlin, *Blood* 2002, 100, 3240; b) N. Lenain, M. Freund, C. Léon, J. P. Cazenave, C. Gachet, *Journal of Thrombosis and Haemostasis* 2003, 1, 1144; c) S. S. Smyth, E. D. Reis, H. Vaaninen, W. Zhang, B. S. Coller, *Blood* 2001, 98, 1055.

[17] N. Mackman, *Nature* 2008, 451, 914.

[18] S. P. Jackson, *Nat Med* 2011, 17, 1423.

[19] a) G. DiMinno, M. J. Silver, *Journal of Pharmacology and Experimental Therapeutics* 1983, 225, 57; b) A. Angelillo-Scherrer, P. G. de Frutos, C. Aparicio, E. Melis, P. Savi, F. Lupu, J. Arnout, M. Dewerchin, M. F. Hoylaerts, J.-M. Herbert, D. Collen, B. Dahlback, P. Carmeliet, *Nat Med* 2001, 7, 215; c) A. D. Warren, G. A. Kwong, D. K. Wood, S. N. Bhatia, Manuscript in preparation.

[20] B. M. Koeppen, B. A. Stanton, *Renal physiology*, Mosby Elsevier, Philadelphia, 2007.

[21] a) P. Vestergaard, R. Leverett, *J Lab Clin Med* 1958, 51, 211; b) M. Wyss, R. Kaddurah-Daouk, *Physiol Rev* 2000, 80, 1107.

[22] a) J. H. Roe, J. H. Epstein, N. P. Goldstein, *Journal of Biological Chemistry* 1949, 178, 839; b) F. Gaspari, N. Perico, G. Remuzzi, *Kidney Int Suppl* 1997, 63, S151; c) Z. Qi, I. Whitt, A. Mehta, J. Jin, M. Zhao, R. C. Harris, A. B. Fogo, M. D. Breyer, *American Journal of Physiology— Renal Physiology* 2004, 286, F590.

[23] a) J. E. Ghadiali, M. M. Stevens, *Advanced Materials* 2008, 20, 4359; b) K. Welser, R. Adsley, B. M. Moore, W. C. Chan, J. W. Aylott, *Analyst* 2011, 136, 29; c) R. de la Rica, D. Aili, M. M. Stevens, *Advanced Drug Delivery Reviews* 2012, 64, 967.

[24] a) P. Yager, G. J. Domingo, J. Gerdes, *Annu Rev Biomed Eng* 2008, 10, 107; b) A. W. Martinez, S. T. Phillips, G. M. Whitesides, E. Carrilho, *Analytical Chemistry* 2009, 82, 3.

[25] B. J. Backes, J. L. Harris, F. Leonetti, C. S. Craik, J. A. Ellman, *Nat Biotechnol* 2000, 18, 187.

[26] a) R. M. Botnar, A. S. Perez, S. Witte, A. J. Wiethoff, J. Laredo, J. Hamilton, W. Quist, E. C. Parsons, A. Vaidya, A. Kolodziej, J. A. Barrett, P. B. Graham, R. M. Weisskoff, W. J. Manning, M. T. Johnstone, *Circulation* 2004, 109, 2023; b) D. Simberg, T. Duza, J. H. Park, M. Essler, J. Pilch, L. Zhang, A. M. Derfus, M. Yang, R. M. Hoffman, S. Bhatia, M. J. Sailor, E. Ruoslahti, *Proceedings of the National Academy of Sciences* 2007, 104, 932; c) T. Hara, B. Bhayana, B. Thompson, C. W. Kessinger, A. Khatri, J. R. McCarthy, R. Weissleder, C. P. Lin, G. J. Tearney, F. A. Jaffer, *JACC Cardiovasc Imaging* 2012, 5, 607.

[27] a) J. Hirsh, A. Y. Y. Lee, *Blood* 2002, 99, 3102; b) B. R. Robinson, A. K. Houng, G. L. Reed, *Circulation* 2000, 102, 1151.

[28] Park J-H et al. (2008) Magnetic Iron Oxide Nanoworms for Tumor Targeting and Imaging. *Adv Mater* 20:1630-1635.

[29] Park J-H et al. (2009) Systematic Surface Engineering of Magnetic Nanoworms for In vivo Tumor Targeting. *Small* 5:694-700.

[30] Kwong G A et al. (2013) Mass-encoded synthetic biomarkers for multiplexed urinary monitoring of disease. *Nature Biotechnology* 31:63-70.

[31] Lin K Y, Kwong G A, Warren A D, Wood D K, Bhatia S N (2013) Nanoparticles that sense thrombin activity as synthetic urinary biomarkers of thrombosis. *ACS Nano* 7:9001-9009.

[32] Morris T A et al. (2003) Urine and plasma levels of fibrinopeptide B in patients with deep vein thrombosis and pulmonary embolism. *Thrombosis Research* 110:159-165.

[33] Smyth S S, Reis E D, Vaananen H, Zhang W, Coller B S (2001) Variable protection of beta3-integrin-deficient mice from thrombosis initiated by different mechanisms. *Blood* 98:1055-1062.

[34] Brand K et al. (2000) Treatment of colorectal liver metastases by adenoviral transfer of tissue inhibitor of metalloproteinases-2 into the liver tissue. *Cancer Research* 60:5723-5730.

[35] Giljohann D A, Mirkin C A (2009) Drivers of biodiagnostic development. *Nature* 462:461-464.

[36] Hermanson G T (2008) *Bioconjugate Techniques* (Academic Press, New York). 2nd Ed.

[37] Posthuma-Trumpie G A, Korf J, Amerongen A (2008) Lateral flow (immuno)assay: its strengths, weaknesses, opportunities and threats. A literature survey. *Analytical and Bioanalytical Chemistry* 393:569-582.

The foregoing written specification is considered to be sufficient to enable one skilled in the art to practice the invention. The present invention is not limited in scope by the examples provided, since the examples are intended as illustrations of various aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A method comprising
administering to a subject a synthetic particle comprising a carrier domain linked by an enzyme susceptible substrate to a detectable marker that comprises a capture ligand that is a hapten connected through a GluFib peptide to a detection ligand,
wherein, when the synthetic particle encounters an enzyme within the subject resulting in in vivo cleavage of the enzyme susceptible substrate, the detectable marker is released from the carrier domain to renal clearance into urine;
obtaining a sample from the subject; and
performing a capture assay on the sample to detect the detectable marker, wherein the presence of the detectable marker in the sample is indicative of the enzyme being present in an active form within the subject.

2. The method of claim 1, wherein the synthetic particle has a plurality of detectable markers.

3. The method of claim 1, wherein the capture assay comprises an ELISA assay or a lateral-flow assay (LFA).

4. The method of claim 3, wherein the enzyme comprises thrombin or matrix-metalloprotease 9 (MMP9).

5. The method of claim 4, wherein the detectable marker comprises the capture ligand at a C-terminus of the GluFib peptide and the detection ligand at an N-terminus of the GluFib peptide.

6. The method of claim 5, wherein when the synthetic particle does not encounter an enzyme resulting in in vivo cleavage of the enzyme susceptible substrate, the synthetic particle is cleared from the subject via organs of the reticuloendothelial system (RES).

7. The method of claim 5, the carrier domain is a protein, a peptide, a polysaccharide, or a synthetic polymer.

8. The method of claim 7, wherein the synthetic particle has a size such that it may only be cleared from the subject by organs of the RES, and the detectable marker has a size such that it is cleared from the subject into urine by renal clearance.

9. The method of claim 1, wherein the synthetic particle has a size such that it may only be cleared from the subject by organs of the RES, and the detectable marker has a size such that it is cleared from the subject into urine by renal clearance.

10. The method of claim 1, wherein the capture assay comprises an affinity agent linked to a solid support wherein the affinity agent binds to the capture ligand on the detectable marker in the urine sample.

11. The method of claim 10, wherein the affinity agent comprises an antibody.

12. The method of claim 10, wherein the affinity agent is selected from the group consisting of antibodies, antibody fragments, aptamers, magnetic beads conjugated with Abs, proteins or peptides on an affinity column.

13. The method of claim 1, wherein the synthetic particle is administered intravenously, orally, or transdermally.

14. The method of claim 1, wherein a plurality of synthetic particles having a plurality of detectable markers are administered to the subject.

15. The method of claim 1, wherein the synthetic particle has a plurality of detectable markers.

16. The method of claim 15, wherein the plurality of enzyme susceptible detectable markers comprise a plurality of capture ligands and a single type of detection ligand.

17. A method comprising:
administering to a subject a particle comprising a carrier domain linked via an enzyme cleavable linker to a detectable marker that includes a hapten, a GluFib peptide, and a detection ligand, wherein a size of the particle inhibits renal clearance and wherein the particle is cleaved in vivo by an enzyme to release the detectable marker, which admits of renal clearance and is excreted in urine;
obtaining a sample from the subject; and
assaying the sample for the detectable marker via a capture assay in which an antibody on a substrate binds to the hapten and a detectable reporter binds to the detection ligand to provide a signal indicative of the enzyme being active within the subject.

18. The method of claim 17, wherein:
the hapten includes one selected from the group consisting of fluorescein, dinitrophenyl, tetra-methylrhodamine, and Alexa Fluor 488;
the capture assay includes an ELISA assay;
the substrate includes a multi-well plate; and
the detectable reporter includes horseradish peroxidase.

19. The method of claim 17, wherein:
the hapten includes one selected from the group consisting of fluorescein, dinitrophenyl, tetra-methylrhodamine, and Alexa Fluor 488;
the capture assay includes lateral flow assay;
the substrate includes a paper strip; and
the detectable reporter includes a gold particle.

20. The method of claim 1, wherein the hapten is selected from the group consisting of fluorescein (FAM), dinitrophenyl (DNP), tetramethylrhodamine (TMR), and Alexa Fluor 488 (AF488).

21. The method of claim 1, wherein the detection ligand is biotin.

22. The method of claim 17, wherein the detection ligand is biotin.

* * * * *

SEQUENCE LISTING

```
<160> NUMBER OF SEQ ID NOS: 4

<210> SEQ ID NO 1
<211> LENGTH: 14
<212> TYPE: PRT
<213> ORGANISM: Artificial Sequence
<220> FEATURE:
<223> OTHER INFORMATION: Synthetic Polypeptide
<220> FEATURE:
<221> NAME/KEY: MISC_FEATURE
<222> LOCATION: (1)..(1)
<223> OTHER INFORMATION: D-isomer
<220> FEATURE:
<221> NAME/KEY: MISC_FEATURE
<222> LOCATION: (3)..(8)
<223> OTHER INFORMATION: D-isomer
<220> FEATURE:
<221> NAME/KEY: MISC_FEATURE
<222> LOCATION: (10)..(14)
<223> OTHER INFORMATION: D-isomer

<400> SEQUENCE: 1

Glu Gly Val Asn Asp Asn Glu Glu Gly Phe Phe Ser Ala Arg
1               5                   10

<210> SEQ ID NO 2
<211> LENGTH: 25
<212> TYPE: PRT
<213> ORGANISM: Artificial Sequence
<220> FEATURE:
<223> OTHER INFORMATION: Synthetic Polypeptide
<220> FEATURE:
```

```
-continued

<221> NAME/KEY: MISC_FEATURE
<222> LOCATION: (1)..(1)
<223> OTHER INFORMATION: D-isomer
<220> FEATURE:
<221> NAME/KEY: MISC_FEATURE
<222> LOCATION: (3)..(8)
<223> OTHER INFORMATION: D-isomer
<220> FEATURE:
<221> NAME/KEY: MISC_FEATURE
<222> LOCATION: (10)..(14)
<223> OTHER INFORMATION: D-isomer
<220> FEATURE:
<221> NAME/KEY: MISC_FEATURE
<222> LOCATION: (15)..(15)
<223> OTHER INFORMATION: Modified with Flsc
<220> FEATURE:
<221> NAME/KEY: MISC_FEATURE
<222> LOCATION: (18)..(18)
<223> OTHER INFORMATION: D-isomer

<400> SEQUENCE: 2

Glu Gly Val Asn Asp Asn Glu Glu Gly Phe Phe Ser Ala Arg Lys Gly
1               5                   10                  15

Gly Phe Pro Arg Ser Gly Gly Gly Cys
            20                  25

<210> SEQ ID NO 3
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 3

Pro Leu Gly Leu Arg Ser Trp
1               5

<210> SEQ ID NO 4
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 4

Pro Leu Gly Val Arg Gly Lys
1               5
```